United States Patent
Johansen et al.

(10) Patent No.: US 12,161,848 B2
(45) Date of Patent: Dec. 10, 2024

(54) AUTO INJECTOR WITH EFFECTIVE INSERTION SYSTEM

(71) Applicant: Phillips-Medisize A/S, Struer (DK)

(72) Inventors: Esben Weldingh Johansen, Struer (DK); Jan Olesen, Holstebro (DK); Jørgen Funder Rasmussen, Holstebro (DK); Emil Wegger Jensen, Viby (DK); Søren Koch Bechmann, Holstebro (DK); Lucile Daul, Struer (DK); Bjarne Sørensen, Aalborg (DK)

(73) Assignee: Phillips-Medisize A/S, Struer (DK)

( * ) Notice: Subject to any disclaimer, the term of this patent is extended or adjusted under 35 U.S.C. 154(b) by 868 days.

(21) Appl. No.: 17/282,007

(22) PCT Filed: Oct. 7, 2019

(86) PCT No.: PCT/EP2019/077068
§ 371 (c)(1),
(2) Date: Apr. 1, 2021

(87) PCT Pub. No.: WO2020/070328
PCT Pub. Date: Apr. 9, 2020

(65) Prior Publication Data
US 2021/0402096 A1 Dec. 30, 2021

(30) Foreign Application Priority Data

Oct. 5, 2018 (DK) .................................. 201870662
Oct. 5, 2018 (DK) .................................. 201870663
Oct. 5, 2018 (EP) ..................................... 18198936

(51) Int. Cl.
*A61M 5/32* (2006.01)
*A61M 5/20* (2006.01)
(Continued)

(52) U.S. Cl.
CPC ............ *A61M 5/3204* (2013.01); *A61M 5/20* (2013.01); *A61M 5/2053* (2013.01); *A61M 5/24* (2013.01);
(Continued)

(58) Field of Classification Search
CPC .... A61M 5/3204; A61M 5/20; A61M 5/2053; A61M 5/24; A61M 5/28; A61M 5/31505;
(Continued)

(56) References Cited

U.S. PATENT DOCUMENTS 3,702,608 A 11/1972 Tibbs
9,592,340 B2 3/2017 Hourmand
(Continued)

FOREIGN PATENT DOCUMENTS

CN 103025373 A 4/2013
CN 103328024 A 9/2013
(Continued)

OTHER PUBLICATIONS

International Preliminary Report on Patentability for PCT Application No. PCT/EP2019/077065, mailed on Mar. 23, 2021, 7 pages.
(Continued)

*Primary Examiner* — Tasnim Mehjabin Ahmed

(57) ABSTRACT

An auto injector for delivery of administering a medicament comprising: a housing; an electrical motor adapted to move a piston between proximal and distal positions in a longitudinal direction of the auto injector; a syringe holder extending from a proximal to a distal end and configured to receive a syringe, a first spring adapted for moving the syringe holder with the syringe proximally for insertion of the needle; wherein the electrical motor is the only motor in the auto injector.

20 Claims, 39 Drawing Sheets

(51) Int. Cl.
*A61M 5/24* (2006.01)
*A61M 5/28* (2006.01)
*A61M 5/315* (2006.01)

(52) U.S. Cl.
CPC .......... *A61M 5/28* (2013.01); *A61M 5/31505* (2013.01); *A61M 5/31576* (2013.01); *A61M 5/31578* (2013.01); *A61M 5/3158* (2013.01); *A61M 5/3202* (2013.01); *A61M 5/3216* (2013.01); *A61M 2005/2013* (2013.01); *A61M 5/2033* (2013.01); *A61M 2005/206* (2013.01); *A61M 2005/2073* (2013.01); *A61M 2005/208* (2013.01); *A61M 2005/2411* (2013.01); *A61M 5/2422* (2013.01); *A61M 2005/2433* (2013.01); *A61M 2005/2492* (2013.01); *A61M 2005/31588* (2013.01); *A61M 2205/12* (2013.01); *A61M 2205/121* (2013.01); *A61M 2205/13* (2013.01); *A61M 2205/14* (2013.01); *A61M 2205/3327* (2013.01); *A61M 2205/42* (2013.01)

(58) Field of Classification Search
CPC .......... A61M 5/31576; A61M 5/31578; A61M 5/3158; A61M 5/3202; A61M 5/3216; A61M 5/2033; A61M 5/2422
See application file for complete search history.

(56) References Cited

U.S. PATENT DOCUMENTS

| | | | |
|---|---|---|---|
| 2003/0105430 | A1 | 6/2003 | Lavi et al. |
| 2005/0049561 | A1 | 3/2005 | Hommann et al. |
| 2011/0004165 | A1 | 1/2011 | Iio |
| 2011/0022461 | A1 | 1/2011 | Simeonov |
| 2011/0301566 | A1 | 12/2011 | Schaefer |
| 2012/0191047 | A1 | 7/2012 | Raday |
| 2013/0150801 | A1 | 6/2013 | Ekman |
| 2013/0172819 | A1 | 7/2013 | Iio et al. |
| 2013/0274677 | A1 | 10/2013 | Ekman |
| 2013/0310746 | A1 | 11/2013 | Wozencroft |
| 2014/0309591 | A1 | 10/2014 | Holmqvist |
| 2015/0202367 | A1* | 7/2015 | Plaschkes ............ A61M 5/2033 604/154 |
| 2015/0265765 | A1* | 9/2015 | Yavorsky ............... A61M 5/142 604/152 |
| 2016/0095983 | A1 | 4/2016 | Lewkonya et al. |
| 2017/0000955 | A1 | 1/2017 | Mcloughlin et al. |
| 2017/0173269 | A1 | 6/2017 | Wozencroft |
| 2018/0104413 | A1 | 4/2018 | Mcloughlin |
| 2018/0361078 | A1 | 12/2018 | Young |
| 2019/0001060 | A1 | 1/2019 | Gylleby et al. |
| 2023/0016544 | A1 | 1/2023 | Hutt |

FOREIGN PATENT DOCUMENTS

| | | |
|---|---|---|
| CN | 103458945 A | 12/2013 |
| CN | 105025954 A | 11/2015 |
| CN | 105451792 A | 3/2016 |
| CN | 105636623 A | 6/2016 |
| CN | 105792866 A | 7/2016 |
| CN | 108136119 A | 6/2018 |
| CN | 109789263 A | 5/2019 |
| EP | 2489380 A1 | 8/2012 |
| GB | 2471473 A | 1/2011 |
| JP | S60179068 A | 9/1985 |
| JP | 2001090638 A | 4/2001 |
| JP | 2005074224 A | 3/2005 |
| JP | 2007111518 A | 5/2007 |
| JP | 2008504934 A | 2/2008 |
| JP | 2015523131 A | 8/2015 |
| JP | 2016112305 A | 6/2016 |
| JP | 2017526490 A | 9/2017 |
| JP | 2017531459 A | 10/2017 |
| WO | 0024441 A1 | 5/2000 |
| WO | 2006007556 A2 | 1/2006 |
| WO | 2009143255 A1 | 11/2009 |
| WO | 2010076569 A2 | 7/2010 |
| WO | 2012066767 A1 | 5/2012 |
| WO | 2013141351 A1 | 9/2013 |
| WO | 2013186619 A1 | 12/2013 |
| WO | 2014037946 A1 | 3/2014 |
| WO | 2014066256 A1 | 5/2014 |
| WO | 2014143815 A2 | 9/2014 |
| WO | 2015118550 A2 | 8/2015 |
| WO | 2017089265 A1 | 6/2017 |

OTHER PUBLICATIONS

International Preliminary Report on Patentability for PCT Application No. PCT/EP2019/077068, mailed on Mar. 23, 2021, 7 pages.
International Preliminary Report on Patentability received for PCT Application No. PCT/EP2019/077061, mailed as on Apr. 15, 2021, 9 Pages.
International Search Report and Written Opinion for PCT Application No. PCT/EP2019/077065, mailed on Feb. 6, 2020, 10 pages.
International Search Report and Written Opinion for PCT Application No. PCT/EP2019/077068, mailed on Dec. 6, 2019, 9 pages.
International Search Report and Written Opinion for PCT Application No. PCT/EP2020/059737, mailed on Jul. 27, 2020, 16 pages.
International Search Report and Written Opinion received for PCT Application No. PCT/EP2019/077061, mailed on Nov. 27, 2019, 10 Pages.
Notification of Reasons for Refusal received for JP application No. 2021-518687, mailed on May 10, 2022, 14 pages. (7 pages of english translation and 7 pages of official copy).
Notification of Reasons for Refusal received for JP application No. 2021-518734, mailed on Apr. 26, 2022, 5 pages. (3 pages of english translation and 2 pages of official copy).
Ex-Parte Quayle office action received for U.S. Appl. No. 17/282,005, mailed on Feb. 14, 2024, 6 pages.
Office Action received for JP Application No. 2021-518766, mailed on Mar. 1, 2022, 12 Pages (06 Pages of English Translation and 06 Pages of Official notification).
Non-Final office action received for U.S. Appl. No. 17/636,027, mailed on Sep. 18, 2024, 22 pages.

* cited by examiner

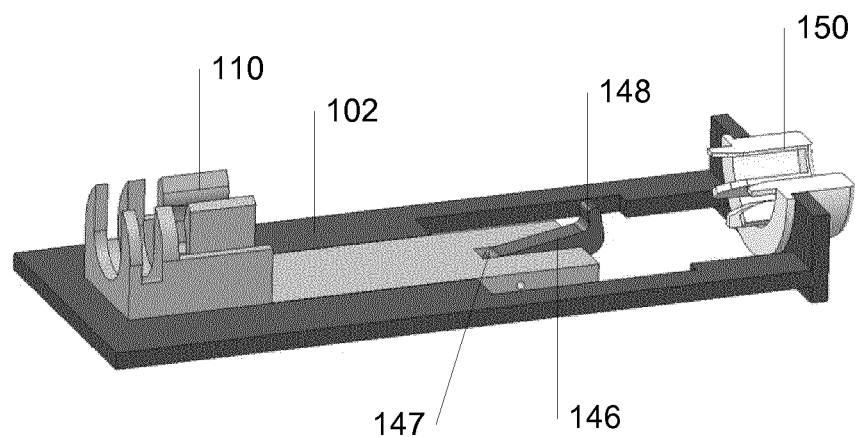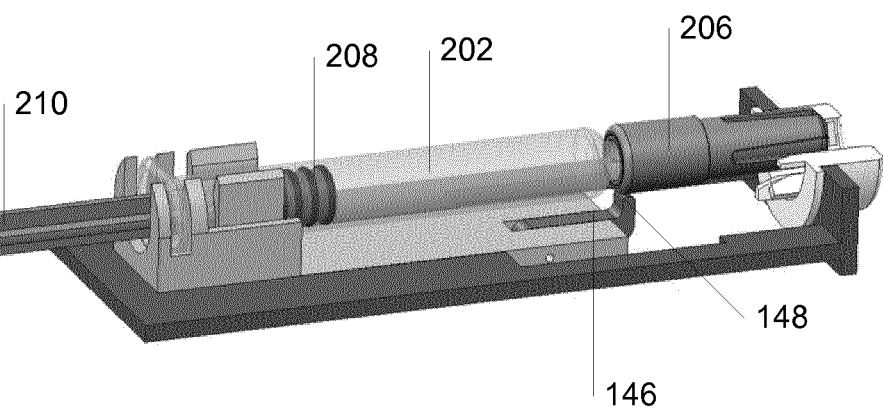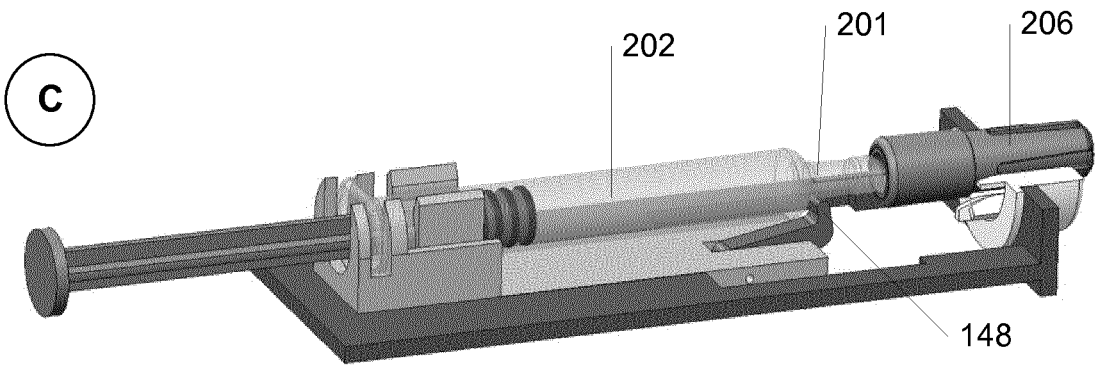
Fig. 5

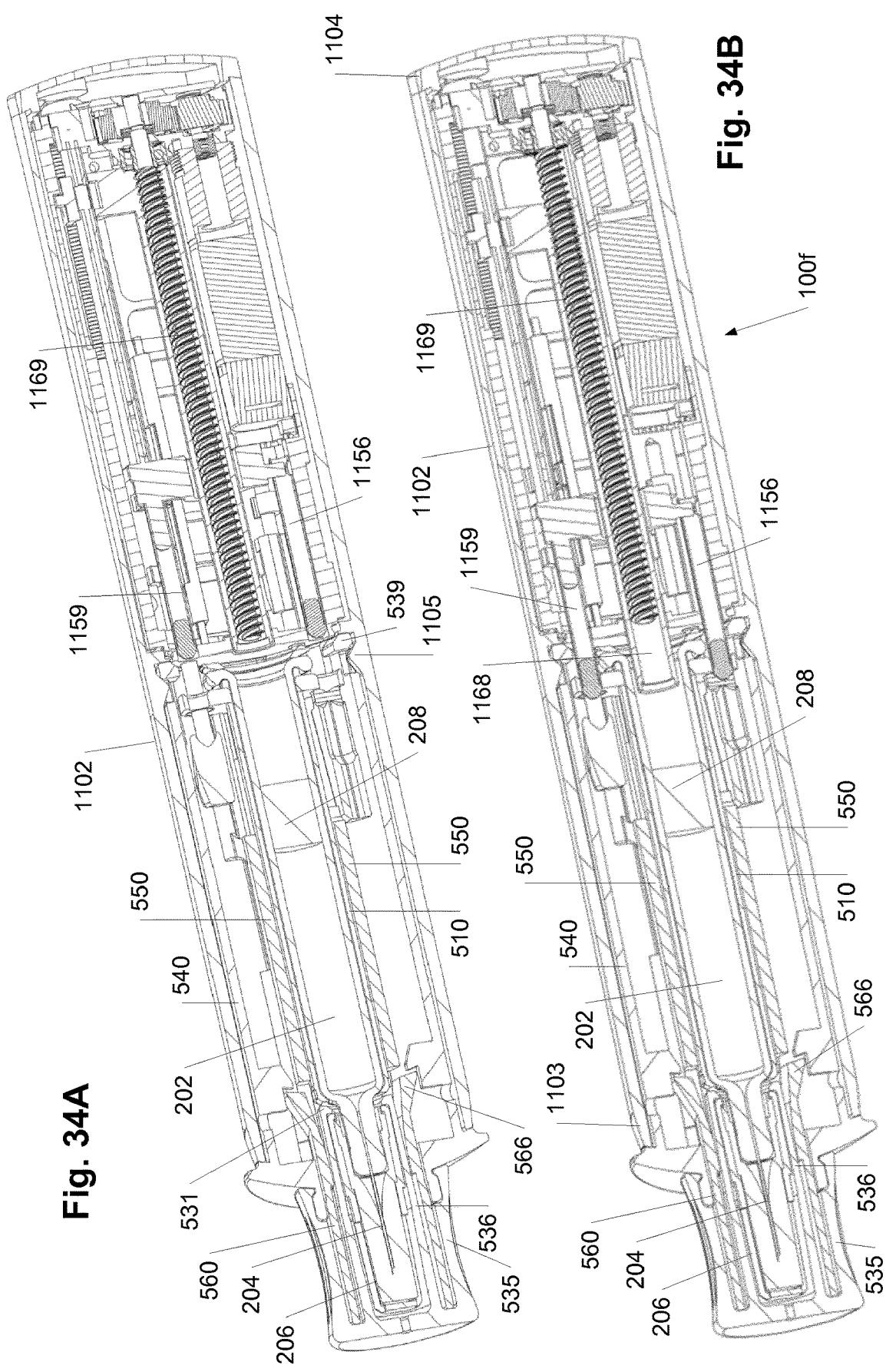

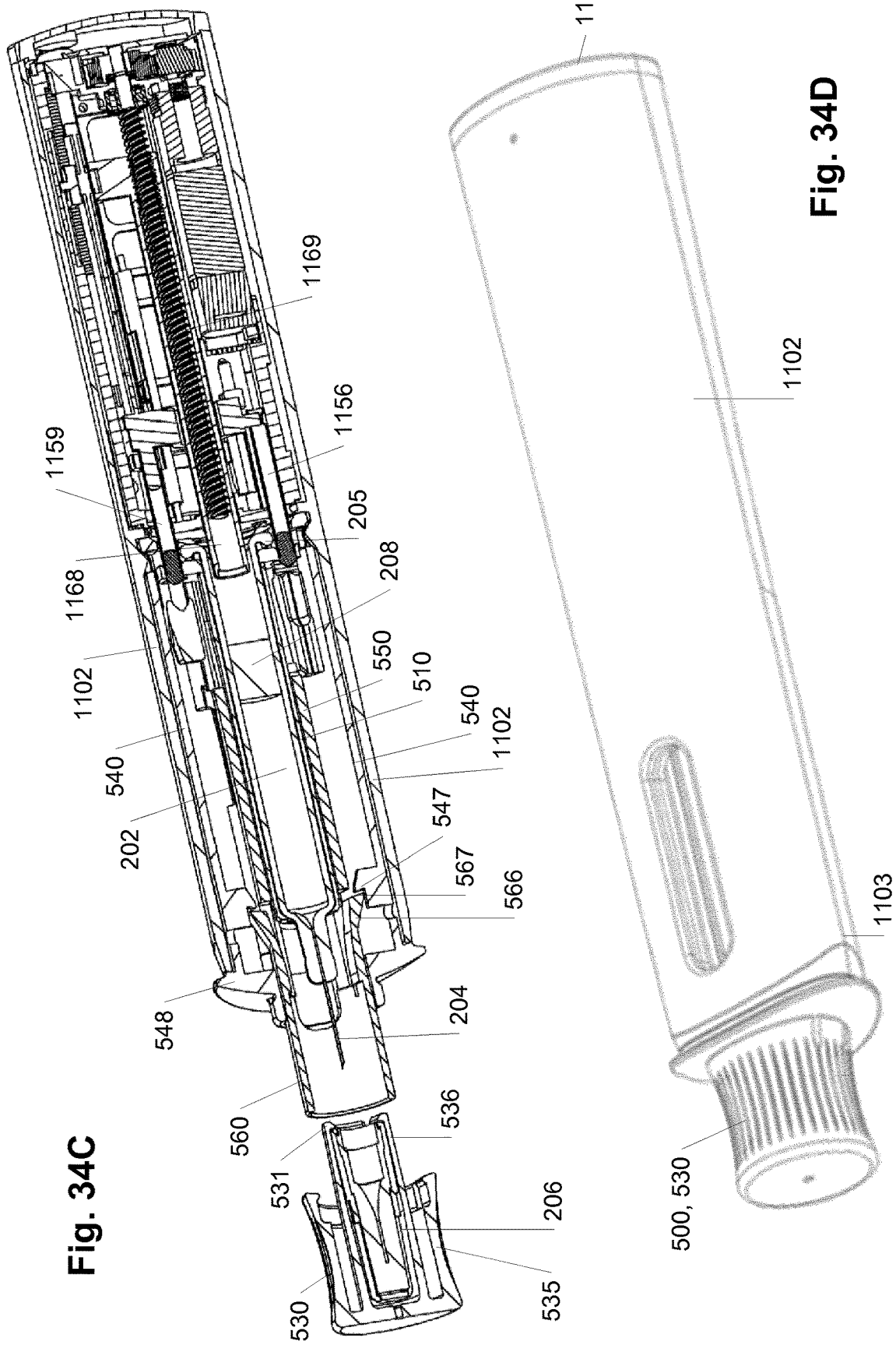

AUTO INJECTOR WITH EFFECTIVE INSERTION SYSTEM

This patent application is a national phase of International Application No. PCT/EP2019/077068, filed Oct. 7, 2019, which claims the benefit of European Patent Application No. 18198936.9 filed Oct. 5, 2018, and Denmark Patent Application No. PA201870663 filed on Oct. 5, 2018 and Denmark Patent Application No. PA201870662 filed on Oct. 5, 2018 all of which are incorporated by reference in their entireties.

The invention relates to an auto injector with an improved rigid needle shield removing mechanism. The invention also relates to an improved cassette and auto injector system.

BACKGROUND

Auto injectors for the delivery of medicament to a patient comes in many varieties depending on the type of medicament, which is to be delivered to the patient. The insertion needle through which the medicament is delivered to the patient is normally protected by a rigid needle shield. Removal of the rigid needle shield is normally done manually and may therefore introduce a risk that the user accidentally comes in contact with the insertion needle prior to insertion.

SUMMARY

Disclosed herein in a first aspect is an auto injector for delivery of a medicament, the auto injector extending from a proximal end to a distal end. The auto injector comprises a housing and a syringe holder configured to receive a syringe comprising:
  a syringe compartment extending from a proximal end to a distal end, the syringe compartment containing the medicament;
  a hollow needle in fluid connection with the proximal end of the syringe compartment;
  a rigid needle shield connected to the proximal end of the syringe compartment and covering the hollow needle;
  a stopper movable from a distal position to a proximal position inside the syringe compartment by means of a plunger rod moving the stopper proximally.

The auto injector further comprises a first drive module adapted to move the syringe holder relatively to the housing, and a rigid needle shield remover comprising a first part adapted for being positioned between the rigid needle shield and the proximal end of the syringe compartment, wherein when the first part is positioned between the rigid needle shield and the proximal end of the syringe compartment, the rigid needle shield can be separated from the proximal end of the syringe compartment upon relative movement between the syringe holder and the rigid needle shield remover, wherein the syringe holder, the first drive module, and the a rigid needle shield remover are comprised inside the housing of the auto injector.

The rigid needle shield remover normally comprises at least two arms extending from a distal end to a proximal end, the at least two arms each pivotally attached to the auto injector or the rigid needle shield remover holder.

The auto injector will normally be reusable, whereas the syringe is a one-time use item.

By the above described auto injector is obtained an improved removal of the rigid needle shield without risking that the user accidentally gets in contact with the insertion needle prior to use. Thus, needle stick injury from manually pulling off rigid needle shield outside of the auto injector is also avoided along with damage to the needle, e.g. bending of the needle if the rigid needle shield is pulled off before inserting the syringe in device.

In general, it requires a high force for pulling off the rigid needle shield manually. This may be difficult for patients with reduced dexterity or similar. By the above auto injector, this problem is avoided.

An alternative solution for a non-manual removal of the rigid needle shield has previously been to use a separate rigid needle shield remover tool dedicated for pulling off the rigid needle shield. Such a rigid needle shield remover tool adds to the cost of the syringe. It may further conflict with inserting the syringe with when the rigid needle shield remover tool is sticking out the front for manual pulling off the rigid needle shield after placing the syringe in auto injector. The need for such a rigid needle shield remover tool is, however, avoided by the above auto injector.

The auto injector is further compact and as the rigid needle shield remover is positioned inside the housing, a more robust solution is obtained compared to previously known auto injectors.

Disclosed herein in a second aspect is a cassette for use in an auto injector for administering a medicament. The auto injector is extending from a proximal end to a distal end and comprises:
  a housing extending from a proximal end to a distal end;
  a piston;
  a cassette receiver configured to receive the cassette;
  a drive module adapted to move the piston and the cassette receiver, wherein the piston and the cassette receiver can be moved together or separately.

The cassette receiver, the piston, and the drive module are comprised inside the housing of the auto injector. The cassette is removable received in the auto injector.

The cassette normally comprises:
  a syringe compartment containing the medicament and extending from a proximal end to a distal end;
  a hollow needle in fluid connection with the proximal end of the syringe compartment;
  a rigid needle shield connected to the proximal end of the syringe compartment and covering the hollow needle;
  a stopper movable from a distal position to a proximal position inside the syringe compartment by means of the piston moving the stopper proximally for emptying the syringe compartment;
  a syringe holder extending around at least part of the syringe compartment;
  a rigid needle shield holder having a first part positioned between the rigid needle shield and the proximal end of the syringe compartment, and
  a cassette skin sensor positioned at the proximal end of the cassette.

By this cassette is obtained an all in one improved cassette with an integrated mechanism for the removal of the rigid needle shield without risking that the user accidentally gets in contact with the insertion needle prior to use. The cassette is compact and robust, which may be used in a simple manner in a front loaded auto injector. The cassette is further operational without spring drivers, which reduces cost. It is a simpler function, as all movement is handled by a reusable auto injector.

Disclose herein in a third aspect is an auto injector for administering a medicament, the auto injector extending from a proximal end to a distal end, the auto injector comprising a housing. Inside the housing is comprised;
  a cassette receiver configured to receive a cassette;

a piston configured for moving the stopper inside the syringe of the cassette proximally thereby emptying the syringe of medicament;

a drive module adapted to move the piston and the cassette receiver, wherein the piston and the cassette receiver can be moved together or separately by the drive module;

a first spring adapted for moving the syringe holder with the syringe compartment connected to the needle proximally for insertion of the needle.

Disclosed herein in a fourth aspect is a cassette for use in an auto injector for administering a medicament. The auto injector is extending from a proximal end to a distal end and comprises:

a housing extending from a proximal end to a distal end;
a piston;
a cassette receiver configured to receive the cassette;
a drive module adapted to move the piston.

The cassette receiver, the piston, and the drive module are comprised inside the housing of the auto injector. The cassette is removable received in the auto injector.

The cassette normally comprises:

a syringe compartment containing the medicament and extending from a proximal end to a distal end;

a hollow needle in fluid connection with the proximal end of the syringe compartment;

a rigid needle shield connected to the proximal end of the syringe compartment and covering the hollow needle;

a stopper movable from a distal position to a proximal position inside the syringe compartment by means of the piston moving the stopper proximally for emptying the syringe compartment;

a syringe holder extending around at least part of the syringe compartment;

a rigid needle shield holder having a first part positioned between the rigid needle shield and the proximal end of the syringe compartment, and a cassette skin sensor.

Disclose herein in a fifth aspect is an auto injector for administering a medicament, the auto injector extending from a proximal end to a distal end, the auto injector comprising a housing. Inside the housing is comprised;

a cassette receiver configured to receive a cassette according to the fourth aspect;

a piston configured for moving the stopper inside the syringe of the cassette proximally thereby emptying the syringe of medicament, and;

a drive module adapted to move the piston.

Disclosed herein in a sixth aspect is an auto injector for delivery of administering a medicament, the auto injector extending from a proximal end to a distal end. The auto injector comprises:

a housing;

an electrical motor adapted to move a piston between proximal and distal positions in a longitudinal direction of the auto injector;

a syringe holder extending from a proximal to a distal end and configured to receive a syringe.

The syringe comprises:

a syringe compartment containing the medicament and extending from a proximal end to a distal end;

a hollow needle in fluid connection with the proximal end of the syringe compartment;

a stopper position inside the syringe compartment, wherein the piston is configured to move the stopper proximally thereby emptying the syringe compartment.

The auto injector further comprises a first spring adapted for moving the syringe holder with the syringe proximally for insertion of the needle. The electrical motor is the only motor in the auto injector.

The auto injector further comprises an activation button adapted for activating the electrical motor for moving the piston proximally, wherein the movement of the piston proximally releases the first spring.

By the above is obtained a robust auto injector with is simpler and more compact than normal due to the use of only one electrical motor in the auto injector.

DETAILED DESCRIPTION

In a first aspect is disclosed an auto injector for delivery of a medicament, the auto injector extending from a proximal end to a distal end. The auto injector comprises a housing and a syringe holder configured to receive a syringe comprising:

a syringe compartment extending from a proximal end to a distal end, the syringe compartment containing the medicament;

a hollow needle in fluid connection with the proximal end of the syringe compartment;

a rigid needle shield connected to the proximal end of the syringe compartment and covering the hollow needle;

a stopper movable from a distal position to a proximal position inside the syringe compartment by means of a plunger rod moving the stopper proximally.

The auto injector further comprises a first drive module adapted to move the syringe holder relatively to the housing, and a rigid needle shield remover comprising a first part adapted for being positioned between the rigid needle shield and the proximal end of the syringe compartment, wherein when the first part is positioned between the rigid needle shield and the proximal end of the syringe compartment, the rigid needle shield can be separated from the proximal end of the syringe compartment upon relative movement between the syringe holder and the rigid needle shield remover, wherein the syringe holder, the first drive module, and the a rigid needle shield remover are comprised inside the housing of the auto injector. The rigid needle shield remover normally comprises at least two arms extending from a distal end to a proximal end, the at least two arms each pivotally attached to the auto injector or the rigid needle shield remover holder.

In one or more examples, the syringe further comprises the plunger rod connected to a distal end of the syringe compartment. The plunger rod may be moved in the proximal direction by a piston being part of the auto injector. Alternative, the user may move the plunger rod proximally for injection of the medicament. Thus, in one or more examples, the syringe further comprises the plunger rod connected to a distal end of the syringe compartment, and the auto injector comprises a piston moving the plunger rod distally for delivery of medicament.

In one or more examples, the auto injector comprises a piston acting as the plunger rod, the piston being positioned inside the housing. The piston may possibly extend outside the housing at a distal end of the piston.

In one or more examples, the auto injector further comprising a first spring adapted for moving the syringe holder proximally for insertion of the needle. A spring is often the preferred choice as it ensures a fast insertion and creates a robust solution.

In one or more examples, the auto injector further comprising an activation button adapted for releasing the first spring such that the syringe holder containing the syringe is moved proximally for insertion of the needle. The activation button may alternatively activate the movement of e.g. the drive module, which in turn releases the first spring during its movement.

In one or more examples, the activation button is positioned outside the housing. This provides the user an easy access to the button.

In one or more examples, the activation button is positioned inside the housing.

In one or more examples, the auto injector further comprising a second drive module adapted for moving the plunger rod distally for the delivery of the medicament. Alternatively, in one or more examples, the first drive module is further adapted for moving the plunger rod distally for the delivery of the medicament. In this manner, the first drive module is adapted for moving multiple parts. This may be obtained if different parts lock together, whereby the movement of one part result in a movement of other parts as well.

In one or more examples, the first drive module is configured for moving the syringe holder distally from a primary position to a secondary position, wherein in the secondary position the first part of the rigid needle shield remover is positioned between the rigid needle shield and the proximal end of the syringe compartment. This ensures that the rigid needle shield remover is positioned correctly by the auto injector instead of requiring the user to do it with the same precision.

In one or more examples, the first drive module is configured for moving the syringe holder further distally from the secondary position to a tertiary position, wherein in the tertiary position the rigid needle shield is loosened from the syringe compartment. Thereby the auto injector loosens the rigid needle shield without the requiring user assistance. This prevents the user from accidentally touching the needle during the process of removing the rigid needle shield.

In one or more examples, wherein during the movement of the syringe holder from the secondary position to the tertiary position, the rigid needle shield remover is not moving.

Alternative, the rigid needle shield remover holding the rigid needle shield may move proximally while the syringe holder is not moving.

In one or more examples, the rigid needle shield remover supports the rigid needle shield in the tertiary position thereby preventing it from being separated from the syringe before the user manually removes it. Thereby the user determines when to remove the rigid needle shield, which is normally not done until immediately before the injection process is initiated.

In one or more examples, wherein the rigid needle shield in the tertiary position is sticking 5-15 mm out of the housing for easy manually removal by the user. This gives the user enough material to be able to easily remove the rigid needle shield at the same time as ensuring that the needle is still positioned inside the auto injector in a position, which the user cannot easily get in touch with as he/she removes the rigid needle shield.

In one or more examples, wherein the auto injector further comprises a rigid needle shield sensor adapted for detecting if the rigid needle shield is attached to the syringe. This ensures that the auto injector will not start the process of inserting the needle until the rigid needle shield has been removed.

In one or more examples, the rigid needle shield sensor is connected to the rigid needle shield remover, the syringe holder, or the syringe. Depending on the design of the syringe, the rigid needle shield sensor may be located in different positions.

In one or more examples, a distal end of the rigid needle shield sensor is connected to the syringe holder and a proximal end of the rigid needle shield sensor is in contact with the rigid needle shield when the rigid needle shield is connected to the syringe.

In one or more examples, the rigid needle shield sensor comprises a spring loaded rotatable arm and an electronic switch, wherein the rotatable arm is in a depressed position when the rigid needle shield is connected to the syringe, and wherein the rotatable arm is in the depressed position interacts with the electronic switch thereby allowing electronics to detect the presence of the rigid needle shield. This provides a simple yet robust detection of the presence of a rigid needle shield.

In one or more examples, the auto injector further comprises one or more additional rigid needle shield sensors adapted for detecting if the rigid needle shield is attached to the syringe at one or more different locations along the length of the rigid needle shield compared to the first mentioned rigid needle shield sensor. This improves the robustness in the detection of the presence of a rigid needle shield.

In one or more examples, the first spring is adapted for moving the syringe holder proximally from the tertiary position to a quaternary position for insertion of the needle.

In one or more examples, the first drive module or the second drive module is moving the plunger rod distally for the delivery of the medicament when the syringe holder is in the quaternary position. Thereby the medicament if delivered to the patient.

In one or more examples, the first drive module is further configured for moving the syringe holder distally from the quaternary position to a quinary position after delivery of the medicament. This brings the auto injection into a configuration from where the syringe can be removed, i.e. the syringe is removable from the auto injector in the quinary position.

In one or more examples, the quinary position and the first position are the same.

In one or more examples, the quinary position and the tertiary position are the same.

In one or more examples, the auto injector further comprises a syringe sensor adapted for detecting when a syringe is positioned in the syringe holder.

In one or more examples, the syringe sensor is positioned inside the housing of the auto injector.

In one or more examples, the auto injector further comprising a rigid needle shield remover holder positioned inside the housing, wherein the distal end of the needle shield remover is pivotally attached to the rigid needle shield remover holder. The rigid needle shield remover holder may be movable in a longitudinal direction relatively to the housing of the auto injector.

In one or more examples, the rigid needle shield remover holder is an integrated part of the housing of the auto injector.

In one or more examples, the rigid needle shield remover comprises at least two arms extending from a distal end to a proximal end. The at least two arms may each be pivotally attached to the auto injector or the rigid needle shield remover holder.

In one or more examples, the distal ends of the at least two arms of the needle shield remover are pivotally attached to the auto injector or the rigid needle shield remover holder.

In one or more examples, a middle position between the distal ends and the proximal ends of each of the at least two arms of the needle shield remover is pivotally attached to the auto injector or the rigid needle shield remover holder.

In one or more examples, the rigid needle shield remover comprises a second part adapted for supporting the rigid needle shield when it has been loosened from the syringe compartment. The second part is preventing the rigid needle shield from accidentally falling off the syringe without manual influence.

In one or more examples, the auto injector further comprises one or more arms springs and wherein the rigid needle shield remover comprises at least two arms, wherein the one or more arms springs pushes the at least two arms centrally at the proximal end of the at least two arms.

In one or more examples, the rigid needle shield sensor is adapted for detecting the angular rotation of the at least two arms towards each other.

In one or more examples, the one or more arms are substantially linear.

In one or more examples, the one or more arms are L-shaped.

In one or more examples, the auto injector further comprising a skin sensor at the proximal end of the auto injector, the skin sensor being longitudinally displaceable relatively to the housing. The skin sensor will normally be depressed when the user places the auto injector on the skin for insertion of the needle and subsequent injection of the medicament.

In one or more examples, the skin sensor covers the insertion needle after insertion. The skin sensor may lock in a proximal position for preventing the user from getting in contact with the needle after injection of medicament.

In one or more examples, the first drive module is an electrical motor.

In one or more examples, the electrical motor of the first drive module is the only motor in the auto injector.

In one or more examples, the second drive module is an electrical motor.

In one or more examples, the auto injector further comprises a syringe comprising:
 a syringe compartment extending from a proximal to a distal end, the syringe compartment containing the medicament;
 a hollow needle in fluid connection with the proximal end of the syringe compartment;
 a rigid needle shield connected to the proximal end of the syringe compartment and covering the hollow needle;
 a stopper movable from a distal position to a proximal position inside the syringe compartment.

Disclosed herein in a second aspect is a cassette for use in an auto injector for administering a medicament. The auto injector is extending from a proximal end to a distal end and is comprising:
 a housing extending from a proximal end to a distal end;
 a piston;
 a cassette receiver configured to receive the cassette;
 a drive module adapted to move the piston and the cassette receiver, wherein the piston and the cassette receiver can be moved together or separately.

The cassette receiver, the piston, and the drive module are comprised inside the housing of the auto injector. The cassette is removable received in the auto injector.

The cassette normally comprises:
 a syringe compartment containing the medicament and extending from a proximal end to a distal end;
 a hollow needle in fluid connection with the proximal end of the syringe compartment;
 a rigid needle shield connected to the proximal end of the syringe compartment and covering the hollow needle;
 a stopper movable from a distal position to a proximal position inside the syringe compartment by means of the piston moving the stopper proximally for emptying the syringe compartment;
 a syringe holder extending around at least part of the syringe compartment;
 a rigid needle shield holder having a first part positioned between the rigid needle shield and the proximal end of the syringe compartment, and
 a cassette skin sensor positioned at the proximal end of the cassette.

In one or more examples, the rigid needle shield holder is contained partly inside the syringe holder.

In one or more examples, the cassette skin sensor is extending partly around the syringe holder and the rigid needle shield holder.

In one or more examples, the syringe compartment, the syringe holder and the cassette skin sensor are moveable in the distal direction relative to the rigid needle shield holder and the needle shield. This allows for a separation of the rigid needle shield from the syringe preparing the cassette for delivery of the medicament to a patient.

In one or more examples, the cassette skin sensor in a first position covers the rigid needle shield and in a second position exposes at least a proximal part of the rigid needle shield allowing the rigid needle shield to be removed.

In one or more examples, the drive module is adapted for moving the cassette skin sensor distally relative to the rigid needle shield thereby exposing the rigid needle shield.

In one or more examples, a distal end of the syringe holder is adapted for locking to the cassette receiver in the auto injector when the cassette is placed inside the auto injector.

In one or more examples, the distal end of the syringe holder is locked to the cassette receiver by a first snap joint, wherein the first snap joint: allows for release of the cassette from the cassette receiver when the piston is in a first position, and locks the cassette to the cassette receiver when the piston is in a second position.

In one or more examples, the distal end of the syringe holder comprises an inner recess, wherein one or more locking arms on the cassette receiver snaps into the inner recess of the syringe holder thereby forming the first snap fit joint.

In one or more examples, rigid needle shield holder is attached to the syringe holder by a second snap joint.

In one or more examples, the syringe holder comprises one or more proximally extending arms and the rigid needle shield holder comprises one or more distally extending protrusions, wherein the one or more proximally extending arms of the syringe holder locks to the one or more distally extending protrusions of the rigid needle shield holder thereby forming the second snap joint.

In one or more examples, upon movement of the syringe holder distally relative to the rigid needle shield holder, the second snap joint is released.

In one or more examples, the auto injector further comprises a chassis adapted for retaining the rigid needle shield holder while the syringe holder is moved distally thereby releasing the second snap fit.

In one or more examples, the cassette skin sensor is locked to the syringe holder by a third snap joint.

In one or more examples, the syringe holder comprises a first support surface and the cassette skin sensor comprises an arm, wherein the arm of the cassette skin sensor rests against the first support surface of the syringe holder thereby forming the third snap joint.

In one or more examples, the third snap joint is released by movement of the cassette skin sensor distally relative to the rigid needle shield holder.

In one or more examples, the rigid needle shield holder comprises an inclining surface adapted for releasing the arm of the cassette skin sensor from the first support surface of the syringe holder when moving the cassette skin sensor distally relative to the rigid needle shield holder.

In one or more examples, after the stopper has been moved proximally for emptying the syringe compartment, a second spring in the auto injector exerts a pressure on the cassette skin sensor in the proximal direction, whereby the cassette skin sensor, the rigid needle shield holder, and the syringe holder locks to each other positioning the cassette skin sensor in a proximal position covering the needle.

In one or more examples, the arm of the cassette skin sensor comprises a first proximal surface; and the rigid needle shield holder comprises a first distal surface, wherein after delivery of the medicament, the first proximal surface of the cassette skin sensor arm and the first distal surface of the rigid needle shield holder abuts thereby preventing the cassette skin sensor from moving proximally in relation to the rigid needle shield holder.

In one or more examples, the cassette skin sensor comprises a first distal surface; and the rigid needle shield holder comprises a first proximal surface, wherein after delivery of the medicament, the first distal surface of the cassette skin sensor and the first proximal surface of the rigid needle shield holder abuts thereby preventing the rigid needle shield holder from moving proximally in relation to the cassette skin sensor.

In one or more examples, the cassette skin sensor comprises a second proximal surface; and the rigid needle shield holder comprises a second distal surface, wherein after delivery of the medicament, the second proximal surface of the cassette skin sensor and the second distal surface of the rigid needle shield holder abuts thereby preventing the rigid needle shield holder from moving distally in relation to the cassette skin sensor.

In one or more examples, the cassette skin sensor comprises a second distal surface; and the syringe holder comprises a first proximal surface, wherein after delivery of the medicament, the second distal surface of the cassette skin sensor and the first proximal surface of the syringe holder abuts thereby preventing the cassette skin sensor from moving distally in relation to the syringe holder.

In one or more examples, the arm of the cassette skin sensor comprises a first proximal surface; and the syringe holder comprises a first distal surface, wherein after delivery of the medicament, the first proximal surface of the cassette skin sensor arm and the first distal surface of the syringe holder abuts thereby preventing the syringe holder from moving distally in relation to the cassette skin sensor.

In one or more examples, the cassette is absent of springs.

In one or more examples, the cassette further comprises a rigid needle shield sensor adapted for detecting if the rigid needle shield is attached to the syringe compartment.

In one or more examples, the rigid needle shield sensor is connected to the rigid needle shield holder.

In one or more examples, a distal end of the rigid needle shield sensor is connected to the rigid needle shield holder and a proximal end of the rigid needle shield sensor is in contact with the rigid needle shield when the rigid needle shield is connected to the syringe compartment.

In one or more examples, the rigid needle shield sensor comprises a spring loaded rotatable arm and an electronic switch, wherein the rotatable arm is in a depressed position when the rigid needle shield is connected to the syringe compartment, and wherein the rotatable arm is in the depressed position interacts with the electronic switch thereby allowing electronics to detect the presence of the rigid needle shield.

In one or more examples, the auto injector further comprises one or more additional rigid needle shield sensors adapted for detecting if the rigid needle shield is attached to the syringe at one or more different locations along the length of the rigid needle shield compared to the first mentioned rigid needle shield sensor.

Disclose herein in a third aspect is further an auto injector for administering a medicament, the auto injector extending from a proximal end to a distal end, the auto injector comprising a housing. Inside the housing is comprised;
- a cassette receiver configured to receive a cassette as described above;
- a piston configured for moving the stopper inside the syringe of the cassette proximally thereby emptying the syringe of medicament;
- a drive module adapted to move the piston and the cassette receiver, wherein the piston and the cassette receiver can be moved together or separately by the drive module;
- a first spring adapted for moving the syringe holder with the syringe compartment connected to the needle proximally for insertion of the needle.

In one or more examples, the drive module is further configured for moving the syringe compartment, the syringe holder and the cassette skin sensor in the distal direction relative to the rigid needle shield holder and the rigid needle shield thereby allowing for removal of the rigid needle shield.

In one or more examples, the auto injector further comprising an actuation button, wherein upon activation of the actuation button, the drive module moves the piston from a distal position in the proximal direction, and wherein the first spring is released during the movement of the piston in the proximal direction.

In one or more examples, the first spring is adapted for moving the syringe holder for insertion of the needle at a needle insertion speed, and the drive module is adapted for moving the piston at a medicament delivery speed, wherein the needle insertion speed is larger than the medicament delivery speed, whereby the piston and the stopper is separated in the longitudinal direction during and for a time period after insertion of the needle before the piston catches up with the syringe compartment.

In one or more examples, further movement of the piston in the proximal direction after the piston catches up with the syringe compartment, moves the stopper in the proximal direction thereby delivering the medicament.

In one or more examples, the auto injector further comprises a syringe sensor adapted for detecting when a syringe is positioned in the syringe holder.

In one or more examples, further comprising a second spring exerting a pressure on the cassette skin sensor in the proximal direction.

Disclosed herein in a fourth aspect is a cassette for use in an auto injector for administering a medicament. The auto injector is extending from a proximal end to a distal end and comprises:
- a housing extending from a proximal end to a distal end;
- a piston;

a cassette receiver configured to receive the cassette;
a drive module adapted to move the piston.

The cassette receiver, the piston, and the drive module are comprised inside the housing of the auto injector. The cassette is removable received in the auto injector.

The cassette normally comprises:
a syringe compartment containing the medicament and extending from a proximal end to a distal end;
a hollow needle in fluid connection with the proximal end of the syringe compartment;
a rigid needle shield connected to the proximal end of the syringe compartment and covering the hollow needle;
a stopper movable from a distal position to a proximal position inside the syringe compartment by means of the piston moving the stopper proximally for emptying the syringe compartment;
a syringe holder extending around at least part of the syringe compartment;
a rigid needle shield holder having a first part positioned between the rigid needle shield and the proximal end of the syringe compartment, and
a cassette skin sensor.

In one or more examples, the syringe compartment, the hollow needle and the stopper is part of a syringe, wherein the syringe is fixed inside the syringe holder, at a distal end of the syringe.

In one or more examples, the cassette is interfacing with the auto injector at the distal end of the cassette sharing the same longitudinal axis. This mitigates risk of the cassette getting stuck inside in the injector and also help to make the connection as slim as possible.

In one or more examples, the syringe holder comprises a syringe holder support tube, which supports the syringe compartment.

In one or more examples, the cassette skin sensor covers at least part of the syringe holder, such as the majority of the syringe holder.

In one or more examples, the cassette skin sensor comprises at least a first skin sensor pin and/or a second skin sensor pin extending from the distal end of the cassette skin sensor.

In one or more examples, the syringe holder comprises one or more openings selected from the group of:
a first pin opening for allowing passage of a first skin sensor release pin of the auto injector there through;
a second pin opening for allowing passage of the first cassette skin sensor pin;
a third pin opening for allowing passage of a skin sensor forward pin of the auto injector, and/or the second cassette skin sensor pin there through;
a fourth pin opening for allowing passage of a second skin sensor release pin of the auto injector there through;
a piston opening for allowing passage of the auto injector piston there through.

In one or more examples, the syringe holder comprises a ring-shaped syringe holder part, wherein the piston opening and/or one or more of the pin openings are positioned in the ring-shaped syringe holder part.

In one or more examples, the syringe holder comprises a first syringe holder arm extending in a proximal direction from the ring-shaped syringe holder part.

In one or more examples, the first syringe holder arm comprises a proximal surface, and wherein the cassette skin sensor comprises a first locking protrusion engaging with the proximal surface, wherein the engagement of the first locking protrusion and the proximal surface prevents movement of the cassette skin sensor towards the syringe holder.

In one or more examples, the first syringe holder arm is flexibly connected to the ring-shaped syringe holder part.

In one or more examples, the first syringe holder arm is deflectable by proximal movement of the first skin sensor release pin of the auto injector through the first pin opening in the syringe holder, wherein the deflection of the first syringe holder arm releases the cassette skin sensor allowing it to move towards the syringe holder.

In one or more examples, upon movement of the cassette skin sensor towards the syringe holder:
the first cassette skin sensor pin is brought into/extends through the second pin opening in the syringe holder, and
the second cassette skin sensor pin is brought into/extends through the third pin opening in the syringe holder.

In one or more examples, the syringe holder comprises a second syringe holder arm extending in a proximal direction from the ring-shaped syringe holder part.

In one or more examples, the second syringe holder arm comprises a distal surface, and wherein the cassette skin sensor comprises a second locking protrusion against which the distal surface is resting, wherein the engagement of the second locking protrusion and the distal surface prevents movement of the cassette skin sensor away from the syringe holder.

In one or more examples, the second syringe holder arm is flexibly connected to the ring-shaped syringe holder part.

In one or more examples, the second syringe holder arm is deflectable by proximal movement of the second skin sensor release pin of the auto injector through the fourth pin opening in the syringe holder, wherein the deflection of the second syringe holder arm allows the cassette skin sensor it to move away from the syringe holder.

In one or more examples, the syringe holder further comprises one or more cassette locking protrusions locking the syringe in the cassette.

In one or more examples, the syringe holder and thereby the cassette is locked to the auto injector housing when the cassette is positioned in the auto injector.

In one or more examples, the syringe holder and the skin sensor are longitudinally movable relative to each other upon release of the skin sensor from the syringe holder.

In one or more examples, the cassette further comprises a cassette housing extending from a proximal to a distal end, the cassette housing enclosing at least the syringe holder and the cassette skin sensor.

In one or more examples, the cassette housing comprises one or more locking openings at the distal end into which the one or more syringe holder locking protrusions on the syringe holder locks syringe holder to the cassette housing.

In one or more examples, the cassette housing comprises one or more internal protruding rails inside the cassette housing for guiding the skin sensor inside the cassette housing.

In one or more examples, the cassette housing comprises a distal end surface with a skin sensor housing opening through which the cassette skin sensor extends.

In one or more examples, the cassette housing is oval.

In one or more examples, the rigid needle shield holder comprises an inner rigid needle shield tube with the first part and an outer an outer rigid needle shield tube, wherein:
the outer rigid needle shield tube surrounds the inner rigid needle shield tube, and
the inner rigid needle shield tube surrounds the rigid needle shield.

In one or more examples, the outer rigid needle shield tube abuts the distal end surface of the cassette housing, and wherein the proximal end of the cassette skin sensor is positioned between the inner rigid needle shield tube and the outer rigid needle shield tube.

In one or more examples, the rigid needle shield holder is removable from the syringe compartment, and wherein when the rigid needle shield holder is removed, the rigid needle shield follows with it, whereby the hollow needle is exposed.

In one or more examples, the rigid needle shield holder is an elongated tube positioned between the syringe and the cassette skin sensor.

In one or more examples, the rigid needle shield holder comprises at least one holder pin extending from a distal end of the rigid needle shield holder.

In one or more examples upon proximal movement of a rigid needle shield holder pin in the auto injector abutting the at least one holder pin, the rigid needle shield holder and thereby also the rigid needle shield is pushed proximally for release of the rigid needle shield.

Disclose herein in a fifth aspect is an auto injector for administering a medicament, the auto injector extending from a proximal end to a distal end, the auto injector comprising a housing. Inside the housing is comprised;
  a cassette receiver configured to receive a cassette according to the fourth aspect;
  a piston configured for moving the stopper inside the syringe of the cassette proximally thereby emptying the syringe of medicament, and;
  a drive module adapted to move the piston.

In one or more examples, the auto injector further comprising one or more pins selected from the group of:
  a first skin sensor release pin;
  a skin sensor forward pin;
  a second skin sensor release pin;
  a cassette detection pin.

In one or more examples, the cassette receiver is a cassette receiving chassis extending from a proximal end to a distal end, wherein the proximal end of the chassis comprises a ring-shaped chassis part with one or more openings selected from the group of:
  a piston opening for allowing passage of the auto injector piston there through;
  a first pin opening for allowing passage of the first skin sensor release pin there through;
  a second pin opening for allowing passage of the first cassette skin sensor pin;
  a third pin opening for allowing passage of:
    the skin sensor forward pin of the auto injector, and/or
    the second cassette skin sensor pin
  there through;
  a fourth pin opening for allowing passage of the second skin sensor release pin there through;
  a fifth opening for allowing passage of the cassette detection pin there through.

In one or more examples, the second pin opening is a well-shaped opening with an end surface limiting the distal movement of the first cassette sensor pin and thereby the cassette skin sensor inside the auto injector.

In one or more examples, drive module is further configured for moving the first skin sensor release pin, the skin sensor forward pin, the second skin sensor release pin, and the cassette detection pin proximally.

In one or more examples, when the drive module moves the first skin sensor release pin proximally, the cassette skin sensor is distally unlocked from the syringe holder allowing for distal movement of the cassette skin sensor, wherein the unlocking of the cassette skin sensor locks the cassette in the auto injector.

In one or more examples, when the drive module moves the piston proximally for delivery of medicament, the second skin sensor release pin is also unlocked for movement of the cassette skin sensor proximally after delivery of medicament and/or removal of the auto injector from the patients skin.

In one or more examples, the auto injector further comprising a skin sensor spring system pushing the skin sensor forward pin of the auto injector against the second cassette skin sensor pin at least after release of the cassette skin sensor from the syringe holder by proximal movement of the first skin sensor release pin and the a second skin sensor release pin.

In one or more examples, the skin sensor spring system pushes the cassette skin sensor proximally in a locked position preventing distal movement of the cassette skin sensor.

In one or more examples, the housing is in one piece with a proximal opening for receiving the cassette.

Disclosed herein in a sixth aspect is an auto injector for delivery of administering a medicament, the auto injector extending from a proximal end to a distal end. The auto injector comprises:
  a housing;
  an electrical motor adapted to move a piston between proximal and distal positions in a longitudinal direction of the auto injector;
  a syringe holder extending from a proximal to a distal end and configured to receive a syringe.
The syringe comprises:
  a syringe compartment containing the medicament and extending from a proximal end to a distal end;
  a hollow needle in fluid connection with the proximal end of the syringe compartment;
  a stopper position inside the syringe compartment, wherein the piston is configured to move the stopper proximally thereby emptying the syringe compartment;
The auto injector further comprises a first spring adapted for moving the syringe holder with the syringe proximally for insertion of the needle. The electrical motor is the only motor in the auto injector.

The auto injector further comprises an activation button adapted for activating the electrical motor for moving the piston proximally, wherein the movement of the piston proximally releases the first spring.

By the above is obtained a robust auto injector with is simpler and more compact than normal due to the use of only one electrical motor in the auto injector.

In one or more examples, the piston presses on a plunger rod in the syringe. In an alternative example, the piston presses directly on a stopper inside the syringe.

The hollow needle may be releasable attached to the syringe.

In one or more examples, the electrical motor is adapted for moving the piston proximally for injection of medicament concurrently with the release of the first spring.

In one or more examples, the auto injector comprises a release arm, wherein when the piston passes the release arm, a release finger on the piston releases the first spring.

In one or more examples, the first spring is adapted for moving the syringe holder for insertion of the needle at a needle insertion speed, and the electrical motor is adapted for moving the piston at a medicament delivery speed, wherein the needle insertion speed is larger than the medicament delivery speed, whereby the piston and the stopper is separated in the longitudinal direction during and for a time period after insertion of the needle before the piston catches up with the syringe compartment.

In one or more examples, further movement of the piston in the proximal direction after the piston catches up with the syringe compartment, moves the stopper in the proximal direction thereby delivering the medicament.

In one or more examples, the auto injector further comprises a syringe sensor adapted for detecting when a syringe is positioned in the syringe holder.

In one or more examples, the syringe further comprises a rigid needle shield connected to the proximal end of the syringe compartment and covering the hollow needle, and wherein the auto injector further comprises a rigid needle shield remover adapted for separating the proximal end of the syringe compartment and the rigid needle shield.

In one or more examples, the electrical motor is further adapted for moving the syringe holder in a distal direction for separating the proximal end of the syringe compartment and the rigid needle shield.

The auto injector according to the sixth aspect may also comprise a rigid needle shield remover as described above for the first aspect of the auto injector when receiving a syringe.

The auto injector according to the sixth aspect may also be adapted for receiving a cassette as described above in the second aspect or the fourth aspect.

Any of the above features described in conjunction with a particular aspect/example is not limited to that aspect/example and can be practiced in any other examples even if not so illustrated, or if not so explicitly described.

BRIEF DESCRIPTION OF THE DRAWINGS

Various examples are described hereinafter with reference to the figures. Like reference numerals refer to like elements throughout. Like elements will, thus, not be described in detail with respect to the description of each figure. It should also be noted that the figures are only intended to facilitate the description of the examples. They are not intended as an exhaustive description of the claimed invention or as a limitation on the scope of the claimed invention. In addition, an illustrated example needs not have all the aspects or advantages shown. An aspect or an advantage described in conjunction with a particular example is not necessarily limited to that example and can be practiced in any other examples even if not so illustrated, or if not so explicitly described.

FIGS. 1A-K show cut-through views of a first embodiment of the auto injector before loading of a syringe in the auto injection, during removal of a rigid needle shield, and before, during and after injection of medicament in the syringe.

FIGS. 5A-C show the rigid needle shield sensor for detecting the presence of the rigid needle shield.

FIGS. 25A-B show interior parts of the auto injector according to the fifth embodiment.

FIGS. 34A-C show cut-through views of the auto injector with a cassette in different positions during loading and locking of the cassette in the auto injector, and FIG. 34D show the auto injector with the cassette in a perspective view.

DESCRIPTION OF DRAWINGS

Figure 1:
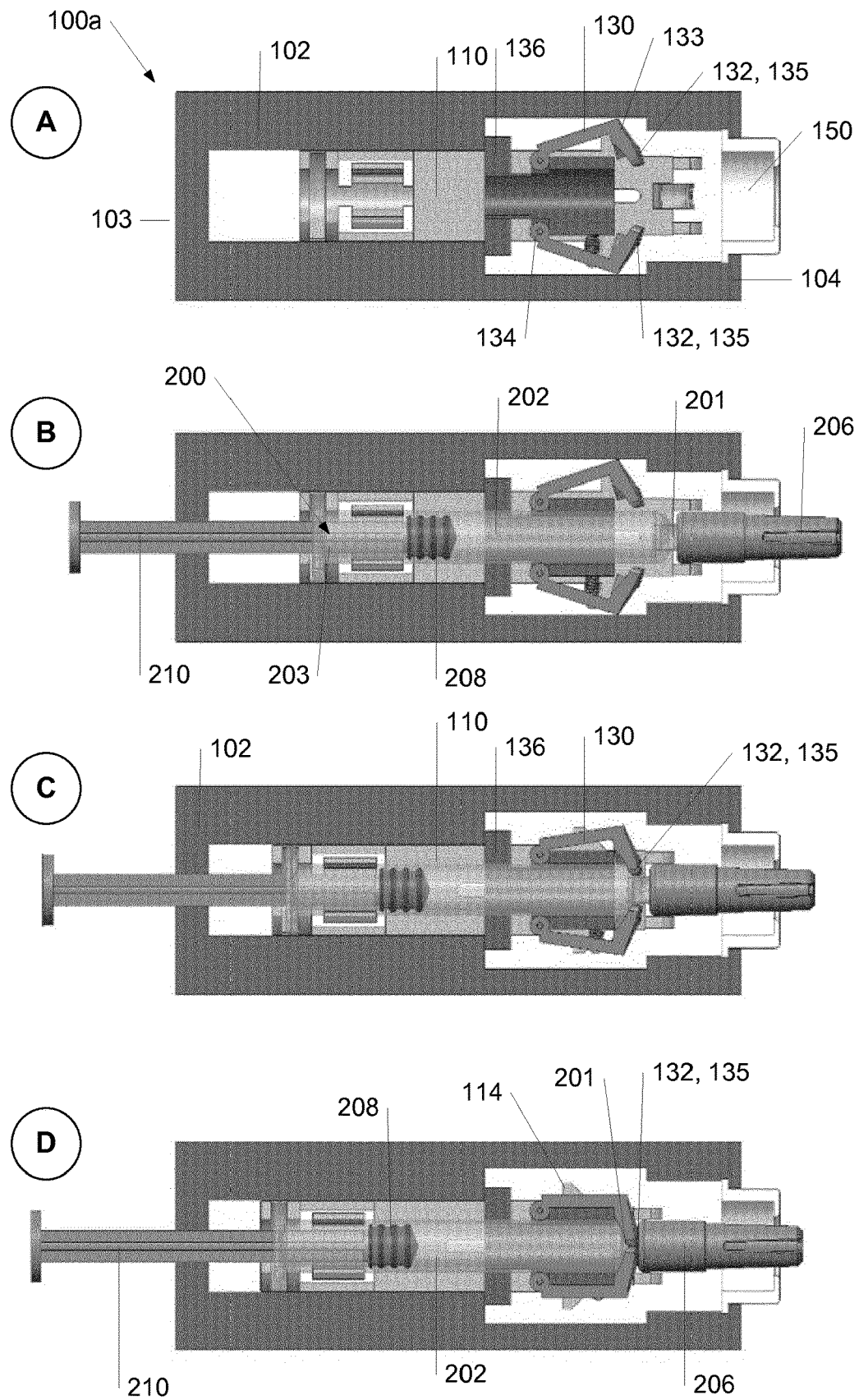
FIGS. 3A1-E2 show cut-through view of a second embodiment of the auto injector during removal of a rigid needle shield. The illustrations in the figures "1" and "2" figures are pairwise the same shown at different cut-through levels.
Figure 1:
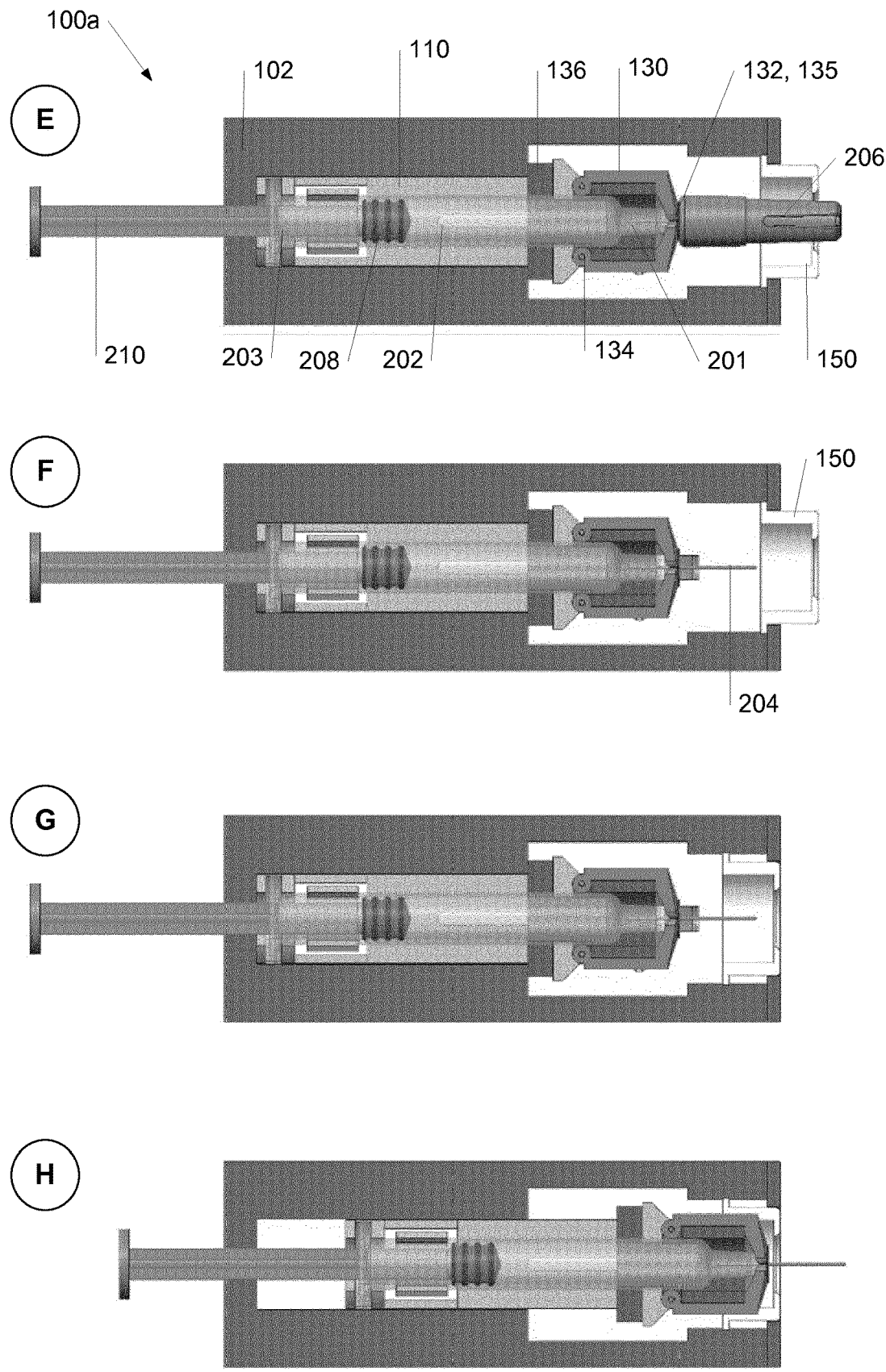
Figure 1:
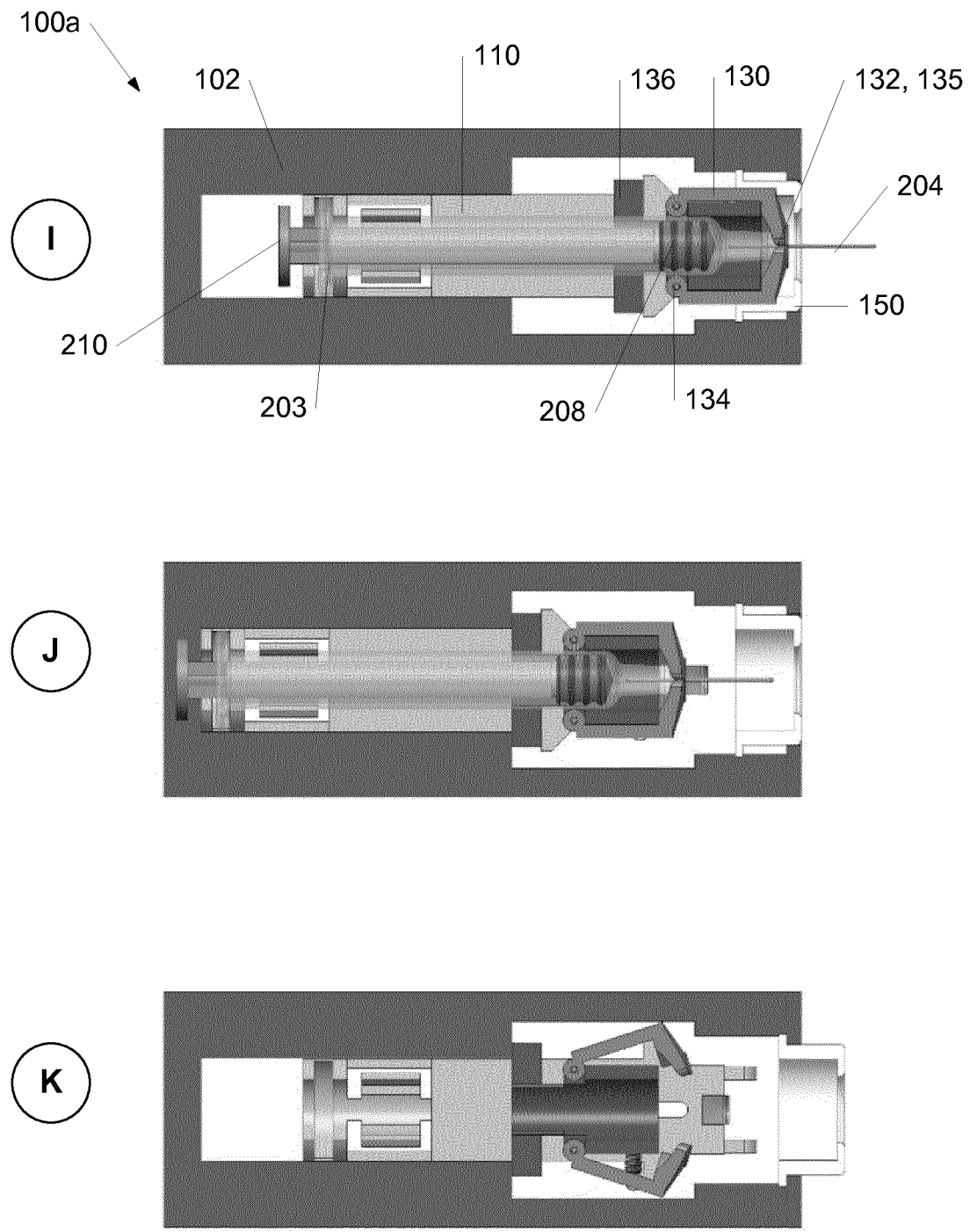

Exemplary examples will now be described more fully hereinafter with reference to the accompanying drawings. In this regard, the present examples may have different forms and should not be construed as being limited to the descriptions set forth herein. Accordingly, the examples are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

In the drawings, thicknesses of a plurality of layers and areas are illustrated in an enlarged manner for clarity and ease of description thereof. When a layer, area, element, or plate is referred to as being "on" another layer, area, element, or plate, it may be directly on the other layer, area, element, or plate, or intervening layers, areas, elements, or plates may be present therebetween. Conversely, when a layer, area, element, or plate is referred to as being "directly on" another layer, area, element, or plate, there are no intervening layers, areas, elements, or plates therebetween. Further when a layer, area, element, or plate is referred to as being "below" another layer, area, element, or plate, it may be directly below the other layer, area, element, or plate, or intervening layers, areas, elements, or plates may be present therebetween. Conversely, when a layer, area, element, or plate is referred to as being "directly below" another layer, area, element, or plate, there are no intervening layers, areas, elements, or plates therebetween.

The spatially relative terms "lower" or "bottom" and "upper" or "top", "below", "beneath", "less", "above", and the like, may be used herein for ease of description to describe the relationship between one element or component and another element or component as illustrated in the drawings. It will be understood that the spatially relative terms are intended to encompass different orientations of the device in use or operation, in addition to the orientation depicted in the drawings. For example, in the case where a device illustrated in the drawings is turned over, elements described as being on the "lower" side of other elements, or "below" or "beneath" another element would then be oriented on "upper" sides of the other elements, or "above" another element. Accordingly, the illustrative term "below" or "beneath" may include both the "lower" and "upper" orientation positions, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below, and thus the spatially relative terms may be interpreted differently depending on the orientations described.

Throughout the specification, when an element is referred to as being "connected" to another element, the element is "directly connected" to the other element, or "electrically connected" to the other element with one or more intervening elements interposed therebetween.

The terminology used herein is for the purpose of describing particular examples only and is not intended to be limiting. As used herein, the singular forms "a," "an," and "the" are intended to include the plural forms, including "at least one," unless the content clearly indicates otherwise. "At least one" is not to be construed as limiting "a" or "an." It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," and the like may be used herein to describe various elements, these elements should not be limited by these terms. These terms are only used to distinguish one element from another element. Thus, "a first element" discussed below could be termed "a second element" or "a third element," and "a second element" and "a third element" may be termed likewise without departing from the teachings herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined in the present specification.

Exemplary examples are described herein with reference to cross section illustrations that are schematic illustrations of idealized examples, wherein like reference numerals refer to like elements throughout the specification. As such, variations from the shapes of the illustrations as a result, for example, of manufacturing techniques and/or tolerances, are to be expected. Thus, examples described herein should not be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. Some of the parts which are not associated with the description may not be provided in order to specifically describe exemplary examples of the present disclosure.

All references to the proximal direction or proximal surfaces refer to parts, surfaces and similar oriented in the direction of insertion, i.e. in the direction of the insertion needle and the outer part of the auto injector touching the skin during injection of the medicament.

Likewise, all references to the distal direction or distal surfaces refer to parts, surfaces and similar oriented in the direction away from the direction of the insertion needle, i.e. in the direction of the user.

FIGS. 1A-K show cut-through views of a first embodiment of the auto injector 100a. FIG. 1A shows the auto injector 100a without a syringe 200 inserted. The auto injector comprises a housing 102 extending from a distal end 103 to a proximal end, where the proximal end 104 is against the patients skin during injection of medicament.

Inside the housing 102 is a syringe holder 110 and a first drive module 120 (not shown in the drawing) adapted to move the syringe holder 110 relatively to the housing 102. The first drive module can e.g. be an electrical motor and may be the only motor in the auto injector 100a.

Inside the housing 102, the auto injector further comprises a rigid needle shield remover 130 extending from a distal end 134 to a proximal end 135. The rigid needle shield remover holder 136 is movable in the longitudinal direction relatively to the housing 102 as seen when comparing e.g. FIGS. 1G, 1H, and 1G. The rigid needle shield remover 130 shown in FIGS. 1A-K comprises two arms 133 each pivotally attached to needle shield remover holder 136 at the distal end of the arms 135.

FIGS. 1B-J show the auto injector 100a with a syringe positioned inside the syringe holder 110. The syringe 200 comprises a syringe compartment 202 extending from a proximal end 201 to a distal end 203. Inside the syringe compartment 202 is the medicament, which is to be administrated to the patient. Also inside the syringe compartment 202 is a stopper 208 movable from a distal position to a proximal position inside the syringe compartment for emptying of the syringe compartment 202. The stopper 208 is moved by a plunger rod 210, which is moving the stopper 208 proximally when emptying the syringe compartment 202.

At the proximal end 201 of the syringe compartment 202 is a hollow needle 204, which is in fluid connection with the syringe compartment and thereby the medicament inside the syringe compartment 202. Connected to the proximal end 201 of the syringe compartment and covering the hollow needle 204 is a rigid needle shield 206.

FIGS. 1B-F shows how the rigid needle shield 206 is automatically removed when the syringe 200 is positioned inside the auto injector 100a. In FIG. 1B, the syringe 200 has just been inserted into the syringe holder 110 and the rigid needle shield remover 130 is in an open position, where the arms 133 are not touching the syringe 200. When the syringe 200 is placed inside the syringe holder 110, the drive module can move the syringe holder 110 with the syringe 200 in the distal direction at the same time as the rigid needle shield remover 130 moves the proximal ends 135 of the arms 133 towards the syringe 200. This brings a first end of the rigid needle shield remover 130 to a position between the rigid needle shield 206 and the proximal end 201 of the syringe compartment. This movement is shown in FIGS. 1B-1D.

When the proximal end 135 of the rigid needle shield is positioned between the rigid needle shield 206 and the proximal end 201 of the syringe compartment 202, the rigid needle shield remover 130 prevent the rigid needle shield 206 from moving with the syringe compartment 202 further in the distal direction as shown in FIG. 1E. By the further movement of the syringe holder 110, when the rigid needle shield is separated from the proximal end of the syringe compartment 202, which enable the user to easily remove the rigid needle shield manually from the syringe 200 inside the auto injector 100a.

Figure 9:
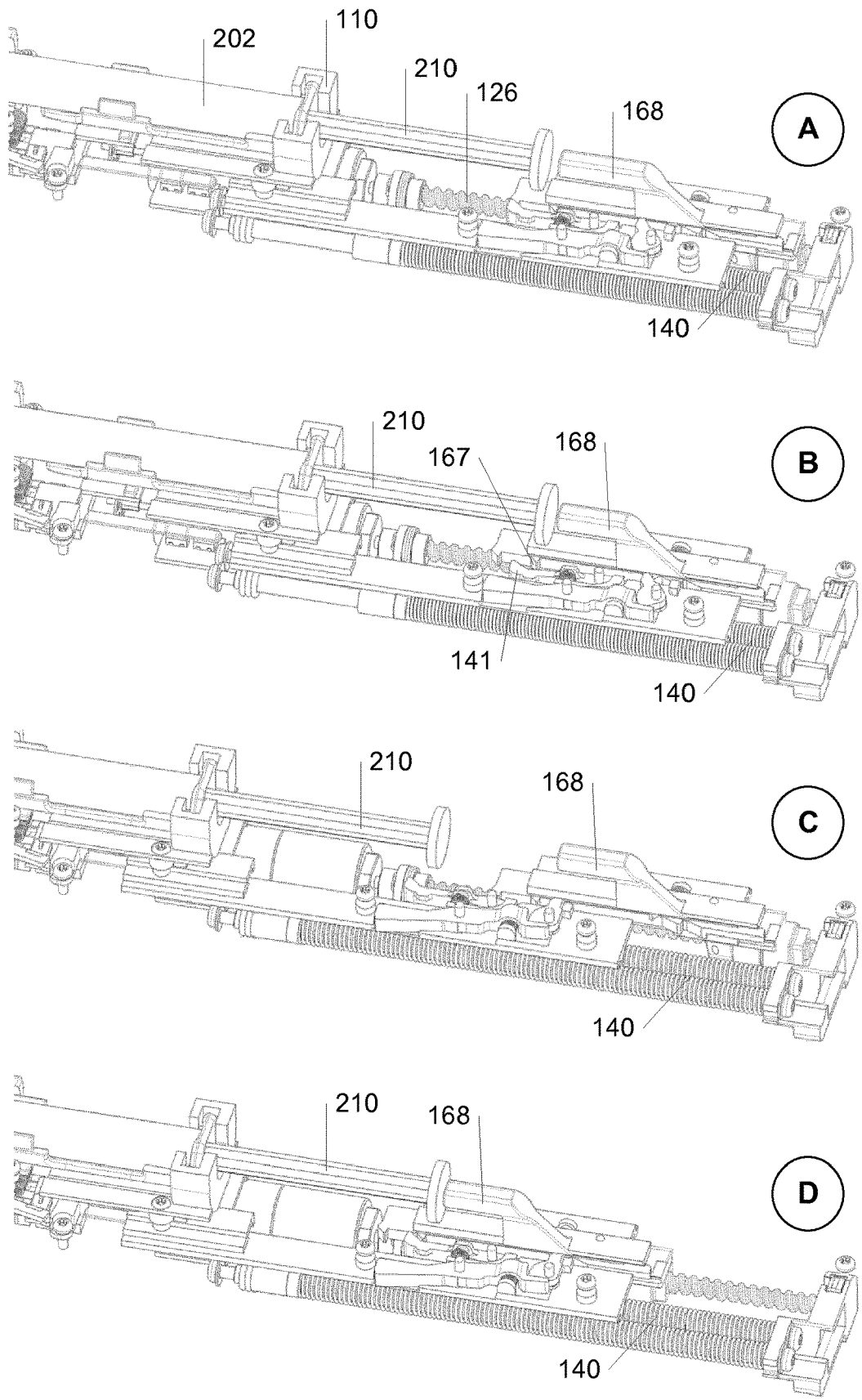
FIGS. 9A-D show the mechanism resulting in the insertion of the needle and the delivery of the medicament in the fourth embodiment of the auto injector in a cut-through view.

In order to avoid that the rigid needle shield 206 is separated from the syringe 200 before the user manually removes the rigid needle shield 206, the rigid needle shield remover 130 may have a second part 138 adapted for supporting the rigid needle shield 206 when it has been separated from the syringe compartment 202. The second part is shown in more detail in the description of the fifth embodiment of the auto injector in FIG. 9.

FIG. 1F show the auto injector with the syringe after the rigid needle shield has been removed therefore exposing the needle 204. In front of the needle at the proximal end of the auto injector 100a is a skin sensor 150. The skin sensor 150 is moveable relatively to the housing 102 such that when the user presses the skin sensor against the skin for insertion of the needle 204 and the subsequent injection of the medicament, the skin sensor 150 is moved in the distal direction. This brings the skin sensor 150 to a position primarily inside the housing 102 as shown in FIG. 1G. The skin sensor 150 comprises an opening at the proximal end allowing at least the insertion needle 204 to pass through.

The auto injector 100a as shown in FIG. 1G is now ready for insertion of the needle 204 and the subsequent injection of the medicament inside the syringe compartment 202. The injection of the needle 204 is done by suppressing an activation button 142 (not shown in the FIGS. 1A-K), which releases a first spring 140 (not shown in the FIGS. 1A-K) whereby the syringe holder 110 containing the syringe 200 is moved proximally for insertion of the needle 204. The activation button may be positioned either outside the housing 102 or inside the housing 102.

FIG. 1H shows the position where the needle 204 has been injected into a patient. In this position, the rigid needle shield remover 130 and its holder 136 has been moved with the syringe 200 in the proximal direction due to the rigid needle shield remover 130 still having its arms closed in around the needle preventing the syringe compartment 202 from bypassing the rigid needle shield remover 130 in the proximal direction. The rigid needle shield remover holder 136 is positioned in contact with a distal surface 114 on the syringe holder 110.

In FIG. 1I, the plunger rod 210 has been moved in the proximal direction. The plunger rod 210 has thereby moved the stopper 208 to its most proximal position whereby the medicament in the syringe compartment 202 has been delivered to the patient. The plunger rod 210 may be moved by means of another plunger rod inside the auto injector pressing on the distal end of the syringe plunger rod 210. The first drive module may control this movement or it may be controlled by a second drive module.

After injection of the medicament, the syringe holder 110 is moved distally bringing the empty syringe 200 with the insertion needle 204 to a position inside the housing 102 where contact with needle 204 is prevented. This is seen in FIG. 1J. The auto injector is now ready for being removed from the skin of the patient. When removing the auto injector from the patient, the skin sensor 150 moves in the proximal direction further protecting the user from the needle 204. Thus, the skin sensor 150 covers the insertion needle 204 after insertion.

After the syringe holder 110 with the empty syringe 200 has been retracted inside the housing 102, the rigid needles shield remover 130 opens up its arms 133 again allowing for an easy removal of the empty syringe 200 from the auto injector 100a. FIG. 1K shows the auto injector 100a after the removal of the syringe 200. The syringe holder 110 and the rigid needles shield remover 130 is now back in its original position as shown in FIG. 1A ready for a new syringe 200 to be positioned inside the auto injector 100a.

FIGS. 2A-E illustrate the longitudinal position of the housing 102, syringe holder 110, and a syringe 200 during the removal of the rigid needle shield 206, and before, during and after injection of medicament in the syringe 200.

In FIG. 2A, the auto injector is in a primary position L1, which correspond to the position shown in FIG. 1B or C. The drive module then moves the auto injector into a secondary position L2 as shown in FIG. 2B corresponding to the position of FIG. 1D, wherein in the secondary position the first part 132 of the rigid needle shield remover 130 is positioned between the rigid needle shield 206 and the proximal end 201 of the syringe compartment 202.

In FIG. 2C, the auto injector has been moved to a tertiary position L3 by the first drive module, wherein in the tertiary position L3 the rigid needle shield is loosened from the syringe compartment. This corresponds to the position shown in FIG. 1E and in FIG. 1F, where the rigid needle shield 206 has been removed. The rigid needle shield 206 in the tertiary position L3 may be sticking 5-15 mm out of the housing 102 for easy manually removal by the user.

In FIG. 2D, the rigid needle shield 206 has been removed and the needle 204 inserted into the patient by the first spring 140. The auto injector is now in a quaternary position L4 corresponding to the position shown in FIGS. 1H and 1I.

After delivery of the medicament, first drive module moved the auto injector to a quinary position L5 as shown in FIG. 2E corresponding to the position shown in FIG. 1J. This also corresponds to the tertiary position as show in FIG. 2C. The empty syringe 200 may be removable from the auto injector 100a in this position. Alternatively, the syringe holder 110 is moved proximally to the primary position L1 for removal of the empty syringe 200.

Figure 3:
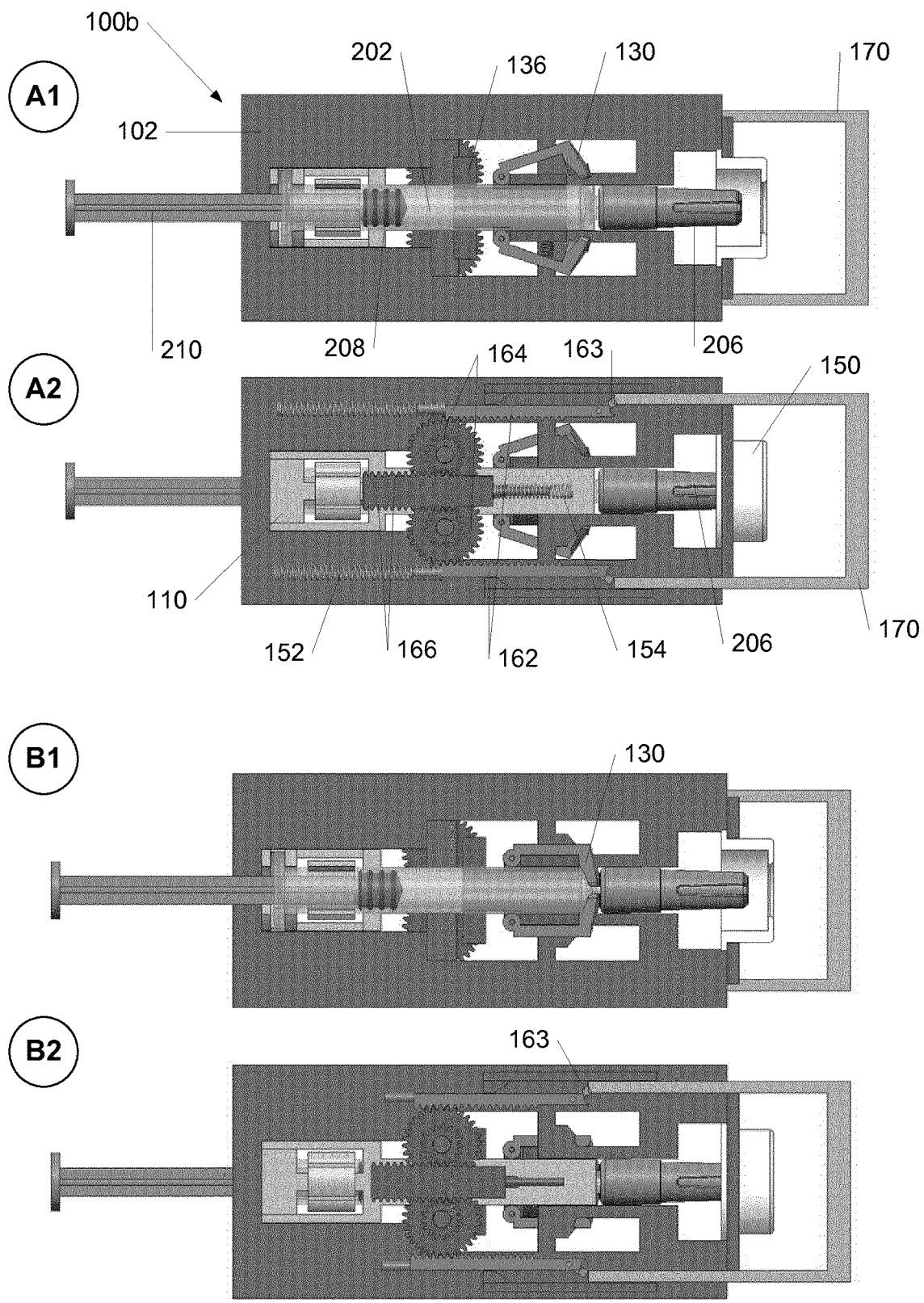
Figure 3:
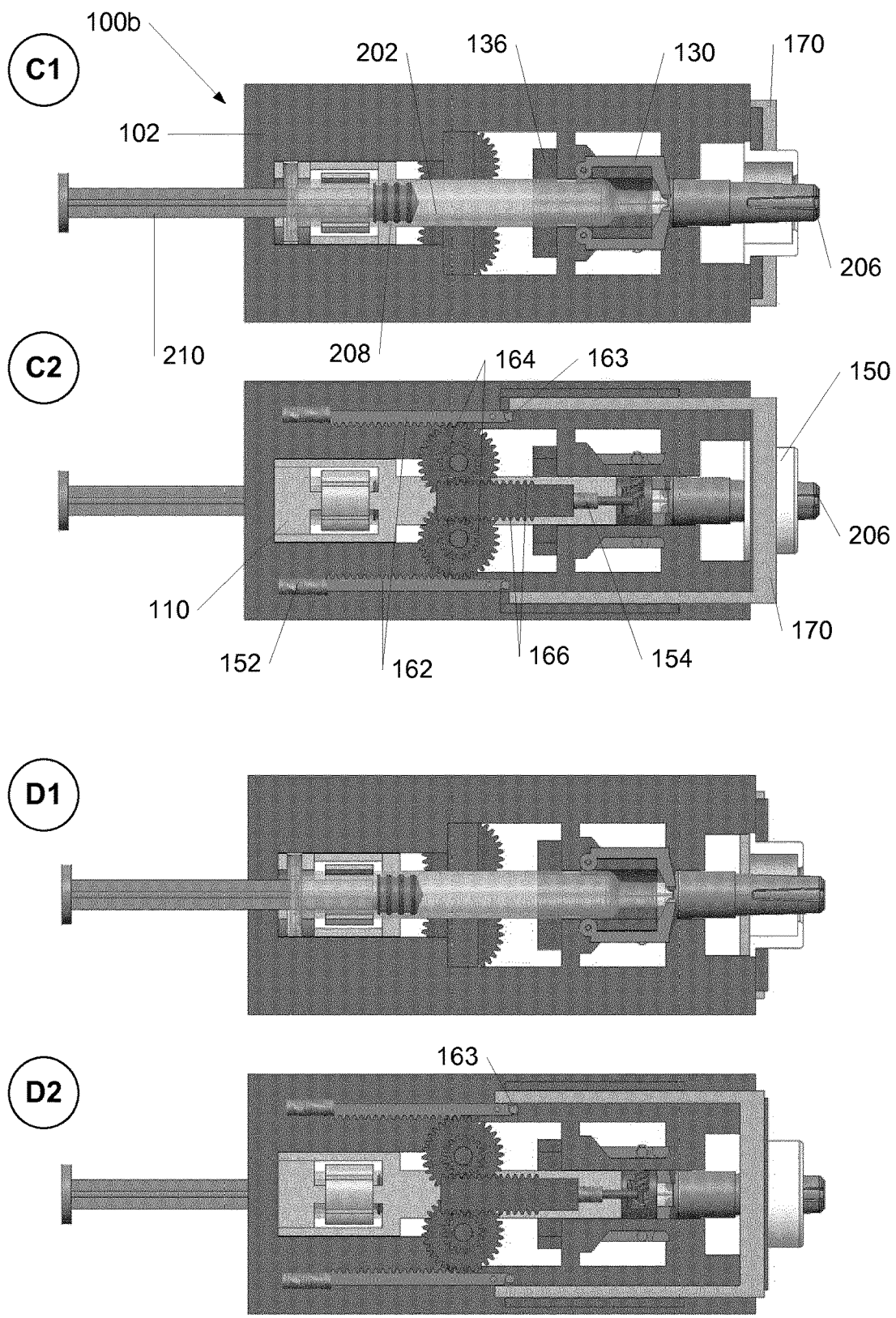
Figure 3:
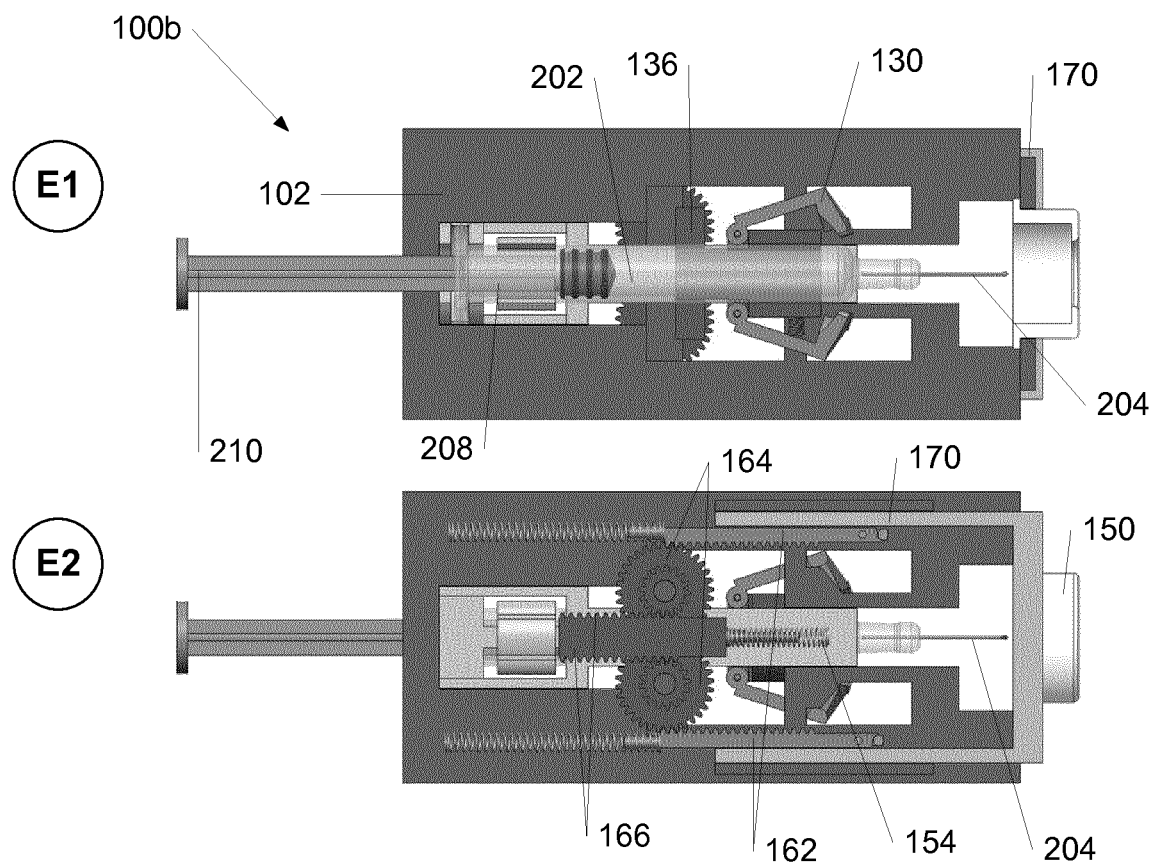

In FIGS. 3A1-E2 a second embodiment of the auto injector 100b is shown. The "1" and "2" images show the auto injector in the same position with the difference being the position where the cut through the auto injector has been made. Like the first embodiment of the auto injector 100a, the second embodiment of the auto injector 100b is extending from a distal end to a proximal end, where the proximal end is against the patients skin during injection of medicament.

Inside the housing 102 is also a syringe holder 110 and a first drive module 120 (not shown in the drawing) adapted to move the syringe holder 110 relatively to the housing 102. The first drive module can e.g. be an electrical motor and may be the only motor in the auto injector 100b.

Inside the housing 102, the auto injector comprises a rigid needle shield remover 130 similar to the one described for the first embodiment. The removal of the rigid needle shield constitutes the differentiating feature between the first and the second embodiment, as the second embodiment of the auto injector 100b comprises a gear rack system positioned inside the housing 102. The gear rack system comprises three rack parts; a first gear rack part 162, a second gear rack part 164 and a third gear rack part 166.

The first gear rack part 162 is displaceable relatively to the housing 102. As shown in FIGS. 3A1-E2, the first gear rack is extending inside a channel extending in the longitudinally direction inside the housing 102. The second gear rack part 164 is connected to the housing 102 and in geared connection with the first gear rack part 162. The second gear rack part is a wheel, which turns around a central axis connected to the housing 102. The third gear rack part 166 is part of the rigid needle shield remover holder 136 to which the needle shield remover 130 is connected. The third gear rack part 166 is displaceable relatively to the housing 102 and is in geared connection with the second gear rack part 164. The second gear rack part 164 connects the first gear rack part 162 and the third gear rack part 166 thereby transferring movement of the first gear rack part 162 to the third gear rack part 166.

The auto injector 100b further comprises a cover 170 which the user can remove from and connect to the housing 102 again after a syringe 200 has been positioned inside the housing 102. The cover 170 can be (manually) moved in the distal direction into a cover channel in the housing 102. Putting the cover onto the auto injector 100b after positioning a syringe 200 inside the housing 102 makes the rigid needle shield arms 133 to move into the gap between syringe 200 and the rigid needle shield 206. This is shown in FIGS. 3A1-2 and 3B1-2, where the rigid needle shield remover 130 is positioned between the rigid needle shield 206 and the proximal end 201 of the syringe compartment in the latter, whereas the rigid needle shield arms 133 are opened in the first illustrations.

When the cover 170 is moved in the distal direction, the cover 170 forces the first gear rack part 162 to move along with it in the distal direction due to the connecting finger 163 as shown by comparing FIGS. 3B1-2 and 3C1-2.

The movement of the first gear rack part 162 distally causes the second gear rack part 164 to rotate whereby the third gear rack part 166 is moved in the proximal direction due to the geared connection between the first/second gear rack parts 162/164 and the second/third gear rack parts 164/166. The first gear rack part 162 causes the third gear rack part 166 to move in the opposite direction with half speed and double force.

The auto injector 100b further comprises two rack springs; a first rack spring 152 and a second rack spring 154. The first rack spring 152 is positioned inside the same channel as the first gear rack part 162 to which it is directly connected to the distal end of the first gear rack part 162.

Figure 2:
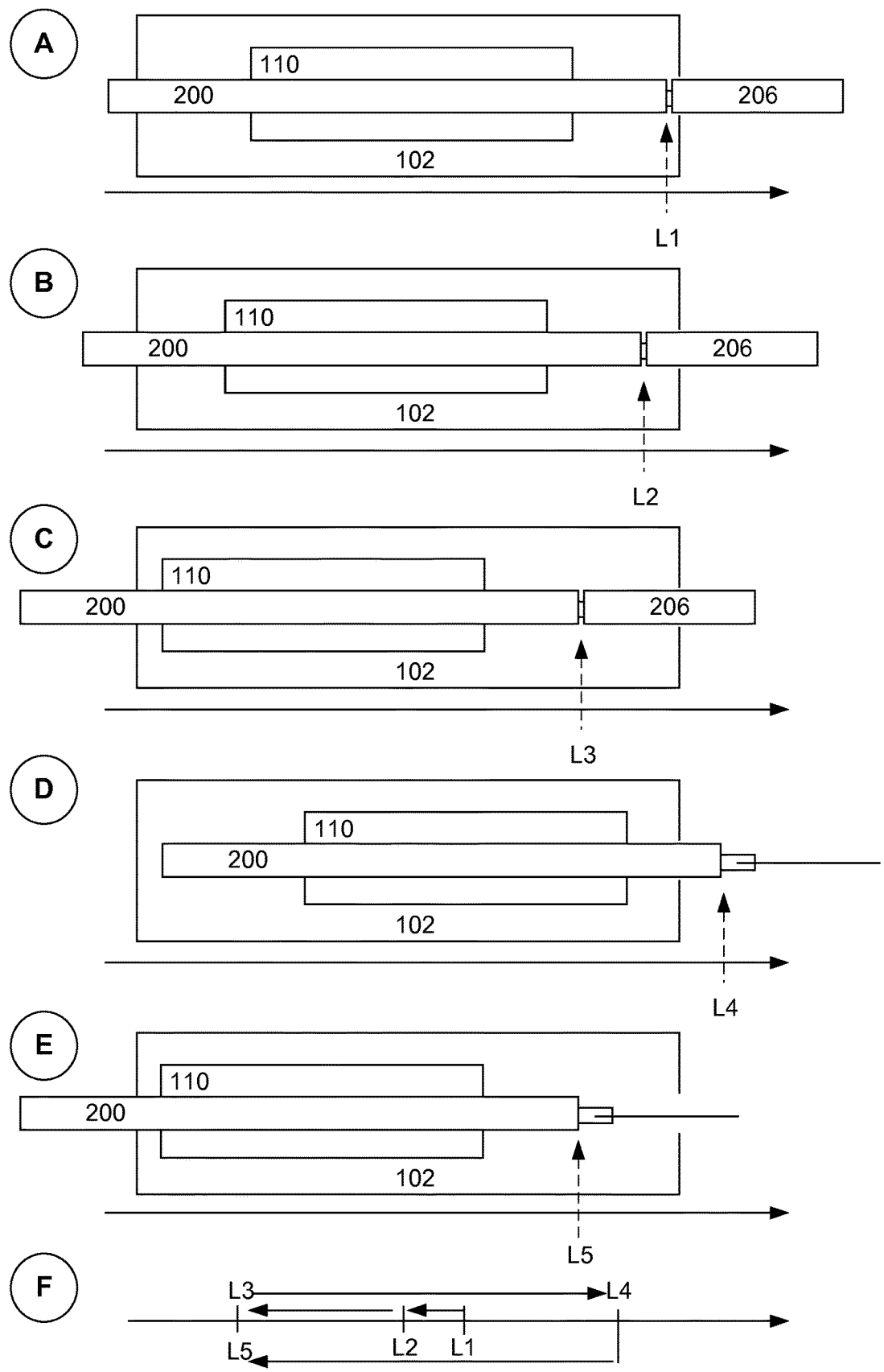
FIGS. 2A-F illustrate the longitudinal position of the syringe holder in the auto injector during removal of the rigid needle shield, and before, during and after injection of medicament in the syringe.

The second rack spring 154 is connected to the rigid needle shield remover holder 136 extending around a part of it as shown in FIGS. 3A2, 3C2, 3D2, and 3E2. In FIG. 3B2 the rack springs 152, 154 are omitted for a clearer view of the remaining parts.

Movement of the first gear rack part 162 in the distal direction, by means of pushing the cover 170 in the distal direction, thereby causes the rack spring 152 to compress as is shown in FIGS. 3C1-2 and 3D1-2. Also, as shown when comparing FIGS. 3A1-2 and 3C1-2, the second rack spring 154 is compressed due to the movement of the third gear rack part 166 in the proximal direction, the latter being a consequence of the gear connection to the first and second gear rack parts 162, 164.

When the cover 170 is moved distally inside the auto injector 100b, the rigid needle shield remover holder 136 is moved proximally pushing the rigid needle shield 206 with it in the proximal direction. This loosens the rigid needle shield 206 from the proximal end 201 of the syringe compartment 202 and the rigid needle shield can now the (manually) removed from the auto injector with the syringe 200 in the positions shown in FIGS. 3C1-D2.

Further, in FIG. 3D2 it can be seen that the first gear rack part 162 is moved against its distal limit, whereby the connecting fingers are forced out of contact with the cover 170 thereby breaking the connection between cover 170 and the first gear rack part 162. When the connection between the cover 170 and the first gear rack part 162 is broken, the first rack spring 152 and the second rack spring 154 are released allowing the gear rack system to reset as the springs 152, 154 relaxes from the compressed positions shown in FIGS. 3C1-3D2. During this reset of the gear rack system, the rigid needle shield remover is opened up as shown in FIGS. 3E1-2 allowing for insertion of the needle 204 and the subsequent injection of the medicament as described for the first embodiment of the auto injector 100a. With the reset, the first gear rack part 162 lies extended alongside the cover 170 inside the housing 102 with the connection fingers pointing straight forward in the proximal direction.

Figure 4:
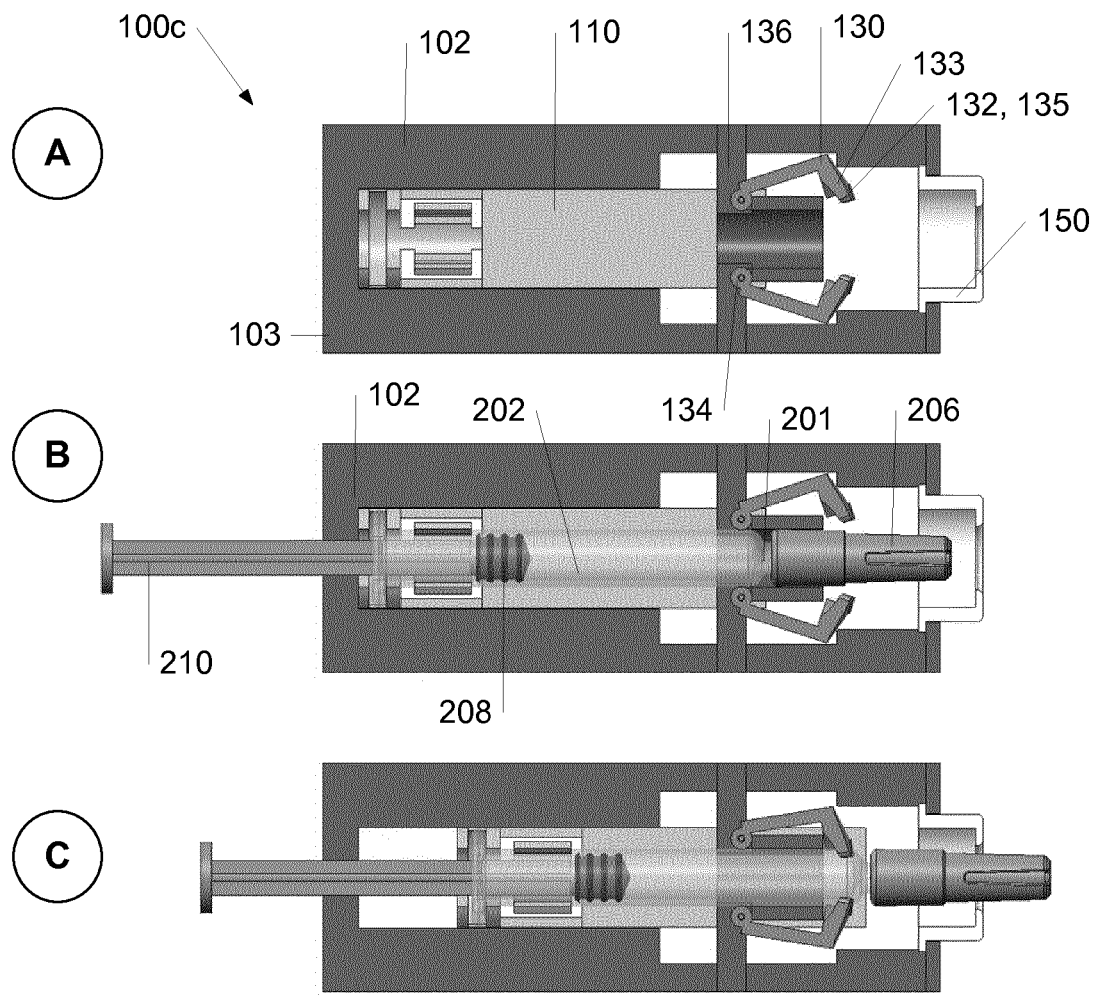
FIGS. 4A-F show cut-through view of a third embodiment of the auto injector during removal of a rigid needle shield.
Figure 4:
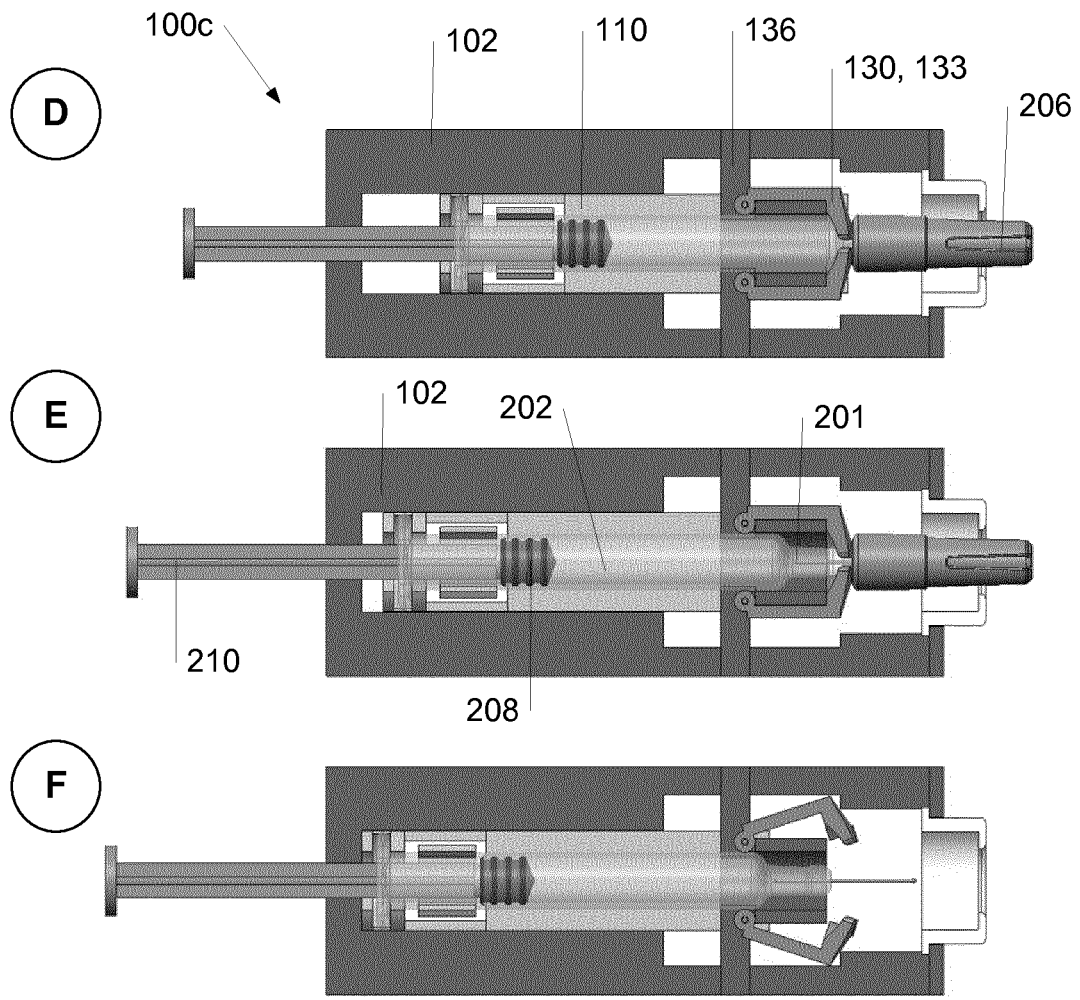

FIGS. 4A-F shows a third embodiment of the auto injector 100c, where FIG. 4A shows the auto injector 100c without a syringe 200 and FIGS. 4B-F shows the auto injector with the syringe 200 inserted. The auto injector 100c comprises a housing 102 extending from a distal end 103 to a proximal end, where the proximal end is against the patients skin during injection of medicament.

Inside the housing 102 is a syringe holder 110 and a first drive module 120 (not shown in the drawing) adapted to move the syringe holder 110 relatively to the housing 102. The first drive module can e.g. be an electrical motor and may be the only motor in the auto injector 100c.

Inside the housing 102, the auto injector further comprises a rigid needle shield remover 130 similarly to the one described in the previous embodiments.

The rigid needle shield remover 130 is connected to a rigid needle shield remover holder 136, which forms part of the housing 102. Compared to the previous embodiments discussed, the rigid needle shield remover holder 136 of the third embodiment of the auto injector 100c is not movable in re to the housing 102.

The syringe holder 110 is in the initial position furthest to the distal end inside the housing 102 as shown in FIG. 4A. The auto injector 100c is now ready for receiving a syringe 200. The rigid needle shield remover 130 is in an open position in this embodiment.

FIG. 4B shows the auto injector 100c with a syringe 200 positioned in the syringe holder 110. In FIG. 4C, the syringe holder 110 with the syringe 200 has been moved in the proximal direction by the drive module. This movement brings the syringe holder 110 into a position corresponding to the primary position L1 as shown and described in FIGS. 2A and 2F. At the same time, the rigid needle shield remover 130 is moving into a position between the rigid needle shield 206 and the proximal end 201 of the syringe compartment 202.

In FIG. 4D, the syringe holder 110 has been moved slightly in the distal direction, and the rigid needle shield remover 130 is now fully positioned between the rigid needle shield 206 and the proximal end 201 of the syringe compartment 202. This position corresponds to the secondary position L2 shown and described in FIGS. 2B and 2F.

FIG. 4E shows the auto injector 100c in a position where the drive module has the syringe holder 110 further in the distal direction without moving the rigid needle shield remover 130.

This loosens the rigid needle shield 206 from the syringe 200. The position corresponds to the tertiary position shown and described in FIGS. 2C and 2F. In this position, the rigid needle shield 206 can be removed by the user.

In FIG. 4F, the rigid needle shield remover 130 has opened up its arms 133 again and the auto injector is ready for insertion of the needle as described in the first embodiment.

All the embodiments of the auto injector described above further comprises a syringe sensor 144 (not shown in the figures) adapted for detecting when a syringe 200 is positioned in the syringe holder 110. The syringe sensor 144 can be positioned inside the housing 102 of the auto injector. The syringe sensor can be positioned in different locations inside the housing 102 or the syringe holder 110.

Placing a cover (e.g. a part of the housing, which is removed when placing the syringe inside the auto injector as discussed in the fourth embodiment of the auto injector) onto the auto injector after positioning of a syringe 200 inside the syringe holder 110 may activate the drive module thereby starting the movement of the syringe holder 110 as described in the above embodiments.

All the embodiments of the auto injector described above further may comprise a rigid needle shield sensor 146 adapted for detecting if the rigid needle shield 206 is attached to the syringe compartment 202. FIGS. 5A-C show an example of a rigid needle shield sensor 146 connected to the syringe holder 110 in an auto injector 100a, 100b, 100c.

The distal end 147 of the rigid needle shield sensor 146 is connected to the syringe holder 110 and the proximal end 148 of the rigid needle shield sensor 146 is in contact with the rigid needle shield 206 when the rigid needle shield 206 is connected to the syringe 200 as shown in FIG. 5B.

Alternatively, the rigid needle shield sensor 146 may be connected to the syringe holder 110 at the different location or be connected to a part of the housing 102. One or more additional rigid needle shield sensors adapted for detecting if the rigid needle shield is attached to the syringe may also be present at one or more different locations along the length of the rigid needle shield 206 when positioned inside the auto injector.

The rigid needle shield sensor 146 shown in FIGS. 5A-C is a spring loaded rotatable arm connected to an electronic switch (not shown). The rotatable arm is in a depressed position as shown in FIG. 5B when the rigid needle shield 206 is connected to the syringe compartment 202. When the rotatable arm is in the depressed position, it interacts with the electronic switch thereby allowing electronics to detect the presence of the rigid needle shield 206. When the rigid needle shield is removed, the rigid needle shield sensor 146 is allowed to relax again as shown in FIG. 5C and the electronic connection to the electronic switch breaks.

In an electronic auto injector, information about whether the rigid needle shield is mounted or fully dismounted from the syringe is important before allowing the user to attempt injection of the medication. If the rigid needle shield still sits on the tip of the syringe compartment when the user attempts insertion of the needle and the subsequent injection of medicament, then potentially no medication would be delivered into the patient.

In the shown design in FIGS. 5A-C, the rigid needle shield sensor 146 only detects the presence of the rigid needle shield 206 close to the syringe compartment 202, however one could easily imagine a design where the rigid needle shield sensor 146 interacts further out (e.g. around the area of the needle tip) whereby even if pulled off but not fully removed, the rigid needle shield 206 would be detectable by the rigid needle shield sensor 146.

Figure 6:
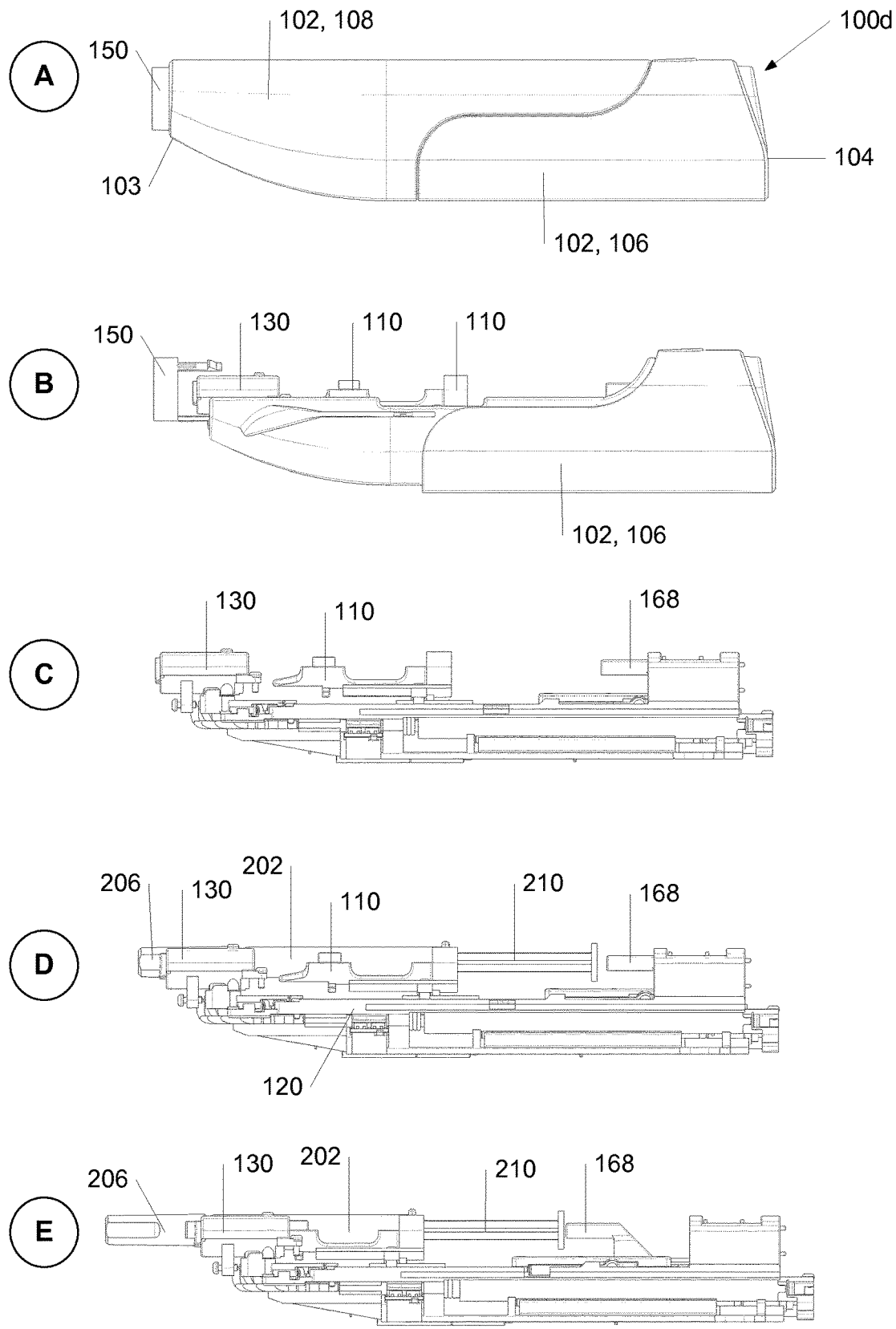
FIGS. 6A-E show view/cut-through view of a fourth embodiment of the auto injector both without a syringe (FIGS. 5A-C) and with a syringe (FIGS. 5D-E).

FIG. 6A shows a fourth embodiment of the auto injector 100*d* comprising a housing 102 extending from a proximal end 103 to a distal end 104. The housing comprises two parts; a first part 106 and a second part 108, the latter forming a removable cover, which allows for the positioning of a syringe inside the auto injector 100*d*. Alternative designs may have the housing constructed as a one-piece item.

In FIG. 6B, the second 108 shown in FIG. 6A has been removed showing the syringe holder 110 and the rigid needle shield remover 130 inside the housing 102 of the auto injector 100*d*.

In FIG. 6C, the first part of the housing 102 and the skin sensor 150 has also been removed whereby the syringe holder 110 and the rigid needle shield remover 130 is seen more clearly. The piston 168 of the auto injector 100*d* can also be seen in FIG. 6C. As shown in FIGS. 6D-E, the piston 168 of the auto injector 100*d* is adapted for moving the plunger rod 210 in the syringe 200 proximally for injection of medicament. Instead of a rod as shown in the figures, a plate or similar in the auto injector may move the plunger rod 210 of the syringe in the proximal direction.

In FIG. 6D a syringe 200 has placed in the syringe holder 110 and in FIG. 6E, the syringe 200 has been moved in the proximal direction by the first drive module 120, whereby the rigid needle shield 206 is in a position for easy removal from the syringe compartment 202.

Figure 7:
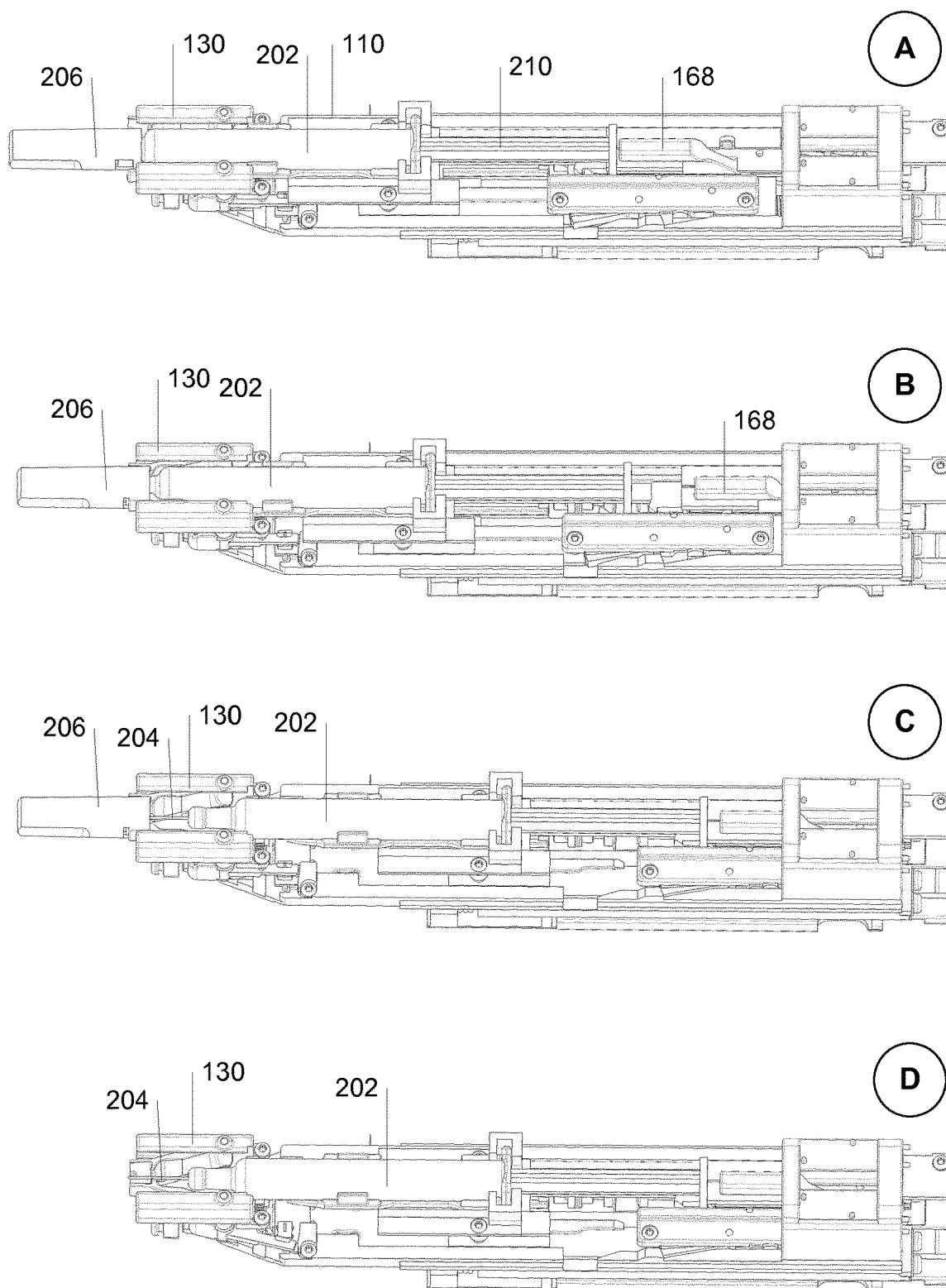
FIGS. 7A-D show the removal of the rigid needle shield in the fourth embodiment of the auto injector in a cut-through view.

FIGS. 7A-D show the auto injector 100*d* with a syringe 200 during the loosening of the rigid needle shield 206 from the syringe compartment 202. In FIG. 7A, the syringe 200 and the syringe holder 110 is in a forward position. As the drive module moves the syringe holder 110 in the distal direction first to the position shown in FIG. 7B and secondly to the position shown in FIG. 7C, the rigid needle shield remover 130 retains the rigid needle shield in the position shown in FIG. 7A thereby loosening the rigid needle shield 206 from the syringe compartment 202. The rigid needle shield can be removed from the syringe compartment 202 as shown in FIG. 7D, which exposes the insertion needle 204. The drive module also moves the piston 168 of the auto injector in the distal direction comparing FIGS. 7A-D.

Figure 8:
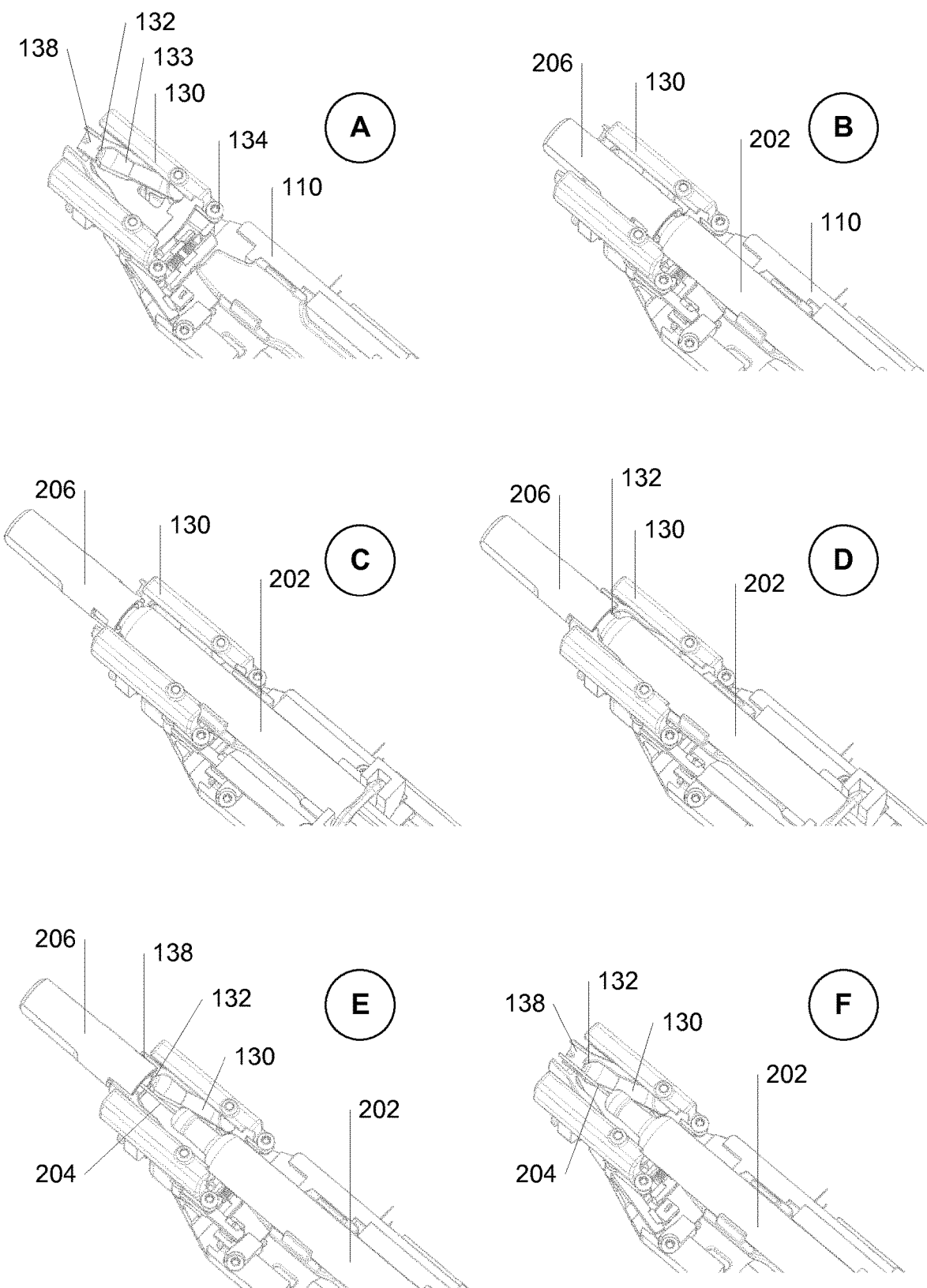
FIGS. 8A-F show a close-up of the removal of the rigid needle shield in the fourth embodiment of the auto injector in a perspective view.

FIGS. 8A-F show a close up of the outer proximal end of the auto injector during the removal of the rigid needle shield. In FIG. 8A, the rigid needle shield remover 130 can be seen before a syringe 200 is positioned in the auto injector 100*d*. The first part 132 of the rigid needle shield remover 130, which is adapted for being positioned between the rigid needle shield and the syringe compartment 202 is clearly visible as a part of the rigid needle shield remover arms 133. At the distal end 134 of the rigid needle shield remover 130 is the second part 138 of the rigid needle shield remover 130, which is adapted for holding the rigid needle shield 206 such that it does not accidentally fall of the syringe after separation from the syringe compartment 202.

In FIG. 8B, the syringe 200 has been positioned inside the auto injector 100*d*. The syringe 200 is in a retracted position and the rigid needle shield remover 130 is not positioned between the rigid needle shield 206 and the syringe compartment 202 yet.

In FIG. 8C, the syringe 200 is in a forward position from where a distal movement of the syringe 200 positions the first part 132 of the rigid needle shield remover 130 between the rigid needle shield 206 and the syringe compartment 202 as shown in FIG. 8D.

In FIG. 8E, the rigid needle shield has been loosened from the syringe compartment 202, but it is retained by the second part 138 of the rigid needle shield remover 130 preventing it from being removed until the user does so manually. In FIG. 8F, the rigid needle shield has been removed by the user and the auto injector 100*d* is ready for injection.

The detection of the presence of a syringe and a rigid needle shield may be obtained using a syringe sensor and a rigid needle shield sensor as described above, e.g. in connection with FIGS. 5A-C.

The rigid needle shield remover arms 133 are pushes centrally at the proximal end by an arm spring, which is not visible in the FIGS. 8A-F. The spring biased configuration provides support to the rigid needle shield remover after the manual removal of the rigid needle shield. The spring biased arms 133 do not interfere with syringe movements and injection procedures and they do not interfere with syringe loading or unloading either due to the rounded edges on top of the arms 133.

The arms 133 can be substantially linear as shown in FIGS. 8A-F or L-shaped as shown in the first three embodiments of the auto injector 100*a*, 100*b*, 100*c*. The rigid needle shield sensor 146 may be adapted for detecting the angular rotation of the two arms 133 towards each other.

FIGS. 9A-D shows mechanism of insertion of the needle and the subsequent injection of medicament. In FIG. 9A, the auto injector 100*d* is in a position ready for activation by pressing an activation button. Upon activation, the drive module 120 (see FIG. 10) moves the piston 168 proximally. When the piston 168 passes a release arm 141 on the auto injector, a release finger 167 on the piston 168 releases the first spring 140 (see FIG. 9B). The first spring 140 forces the syringe holder forward thereby inserting the needle 204. FIG. 9C shows the auto injector 100*d* directly after injection of the needle 204. After insertion of the needle, the drive module 120 continues to move the piston 168 forward in the proximal direction. When the piston 168 catches up with the plunger rod 210, it continues to move the plunger rod 210 (which in turn moves the stopper 208) in the proximal direction thereby delivering the medicament to the patient. This is shown in FIG. 9D.

The first spring 140 is moving at a needle insertion speed, and the drive module is moving the piston at a medicament delivery speed, wherein the needle insertion speed is larger than the medicament delivery speed, whereby the piston 168 and the plunger rod 210 is separated in the longitudinal direction during and for a time period after insertion of the needle 204 before the piston 168 catches up with the syringe compartment 202.

The auto injector 100*d* may further comprising a second spring exerting a pressure on the skin sensor 150 in the proximal direction after removal of the auto injector 100*d* from the skin post injection of the medicament. This pushes the skin sensor 150 in the proximal direction locking the skin sensor 150 in a position where it covers the needle 204 to prevent accidental contact with the needle 204 after injection of medicament.

Figure 10:
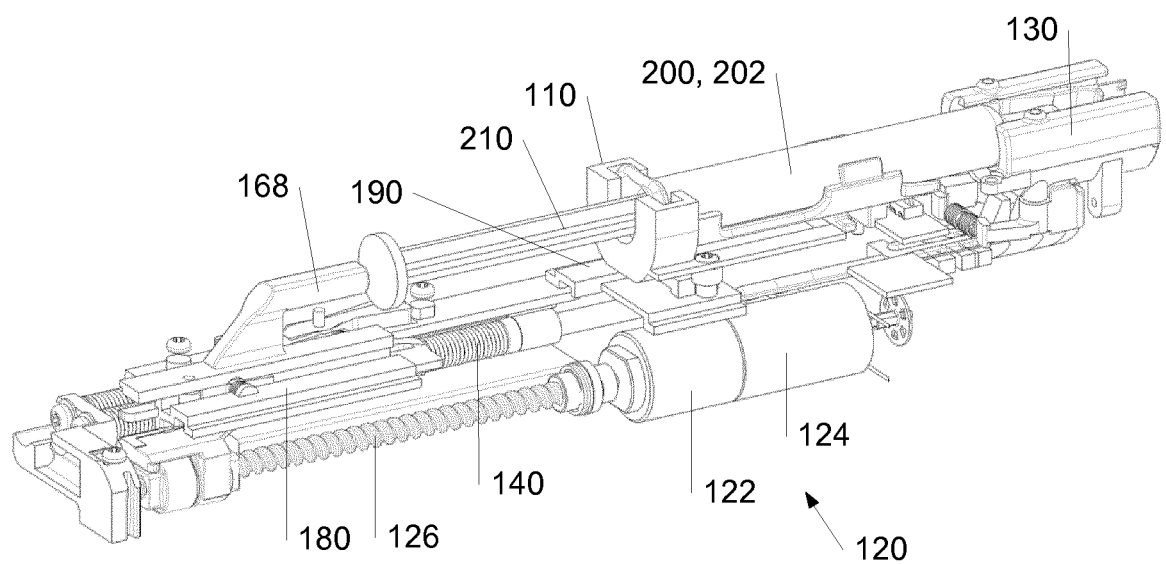
FIG. 10 shows the auto injector as shown in FIGS. 9A-D from a different angle.

FIG. 10 shows interior parts of the auto injector 100*d* connected to a cassette syringe 200 in a perspective view from the distal end. In FIG. 10, the drive module 120 can be seen. The drive module comprises a motor 122 and a gear box 124 connected to a screw 126. The piston 168 is connected to a chassis 180, which in turn is connected to the drive module 120. The syringe holder 110 is connected to a slider 190.

Figure 11A:
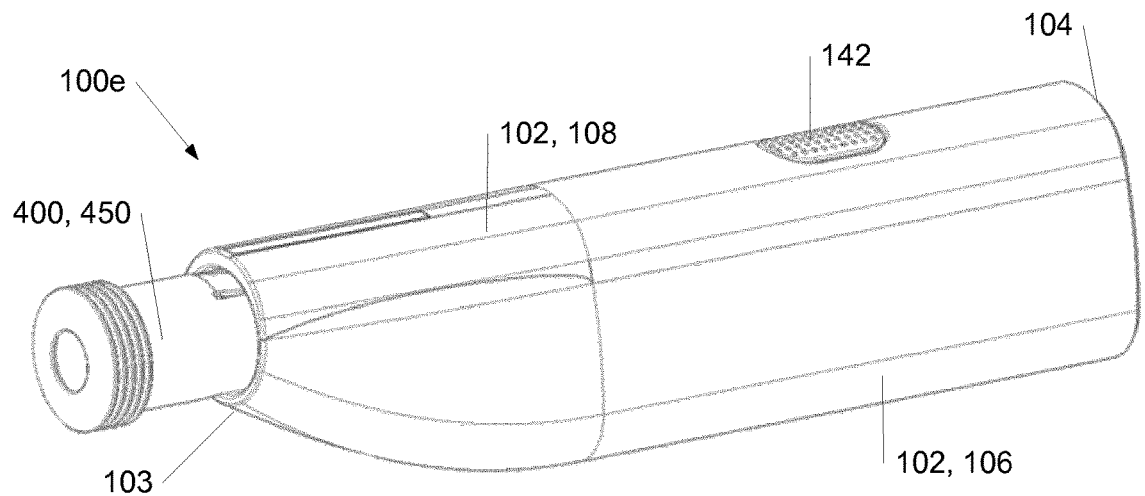
FIGS. 11A-D show a fifth embodiment of the auto injector with a cassette containing in different views.
Figure 11B:
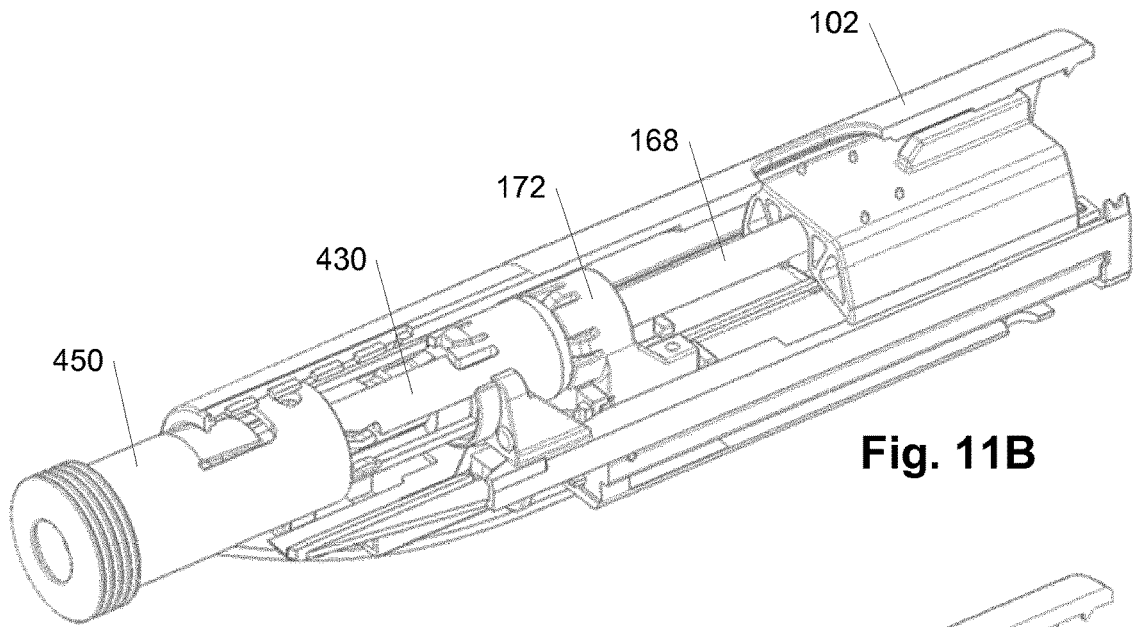
Figure 11C:
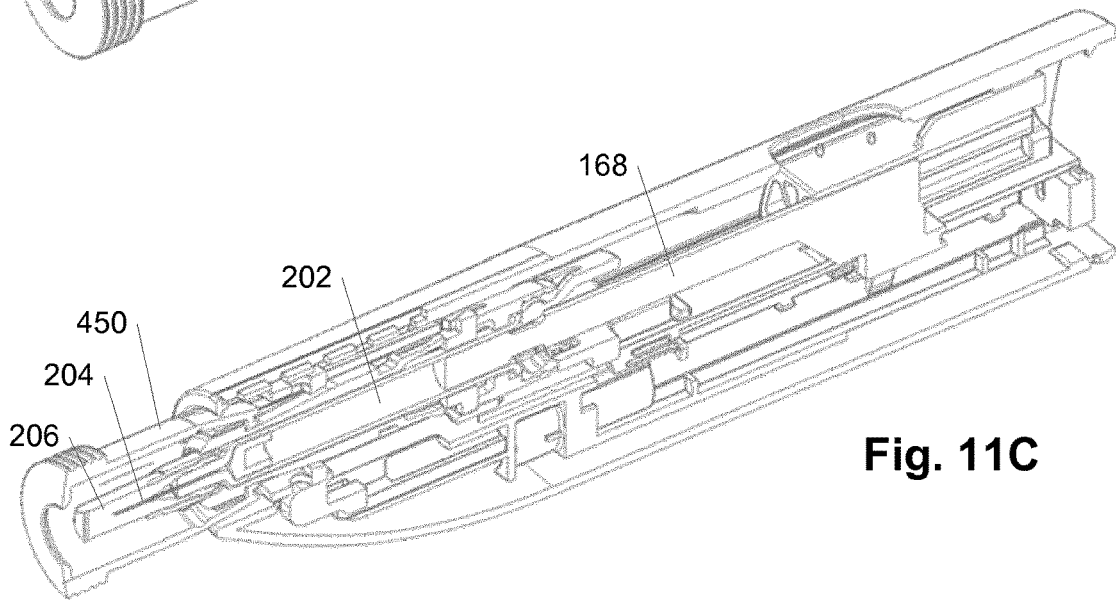

FIGS. 11A-C show a fifth embodiment of the auto injector 100*e* comprising a housing 102 extending from a proximal end 103 to a distal end 104. In FIGS. 11A, the two housing parts; the first part 106 and the second part 108, are visible. The second part 108 is not necessarily removable as a cassette 400 can be front loaded into the auto injector 100*e*. Alternatively, the housing can be a one-piece item. The cassette 400 is visible in FIG. 11A, where the cassette skin sensor 450 is extending outside the proximal end 103 of the housing 102. The activation button 142 is also viewable in FIG. 11A.

In FIG. 11B, the housing 102 has been partly omitted for a clearer view inside the auto injector 100*e*, where the piston 168, the cassette receiver 172 and the cassette with the cassette skin sensor 450 and the rigid needle shield holder 430 can be seen. The cassette 400 is described in more detail in the FIGS. 12-24.

Figure 11D:
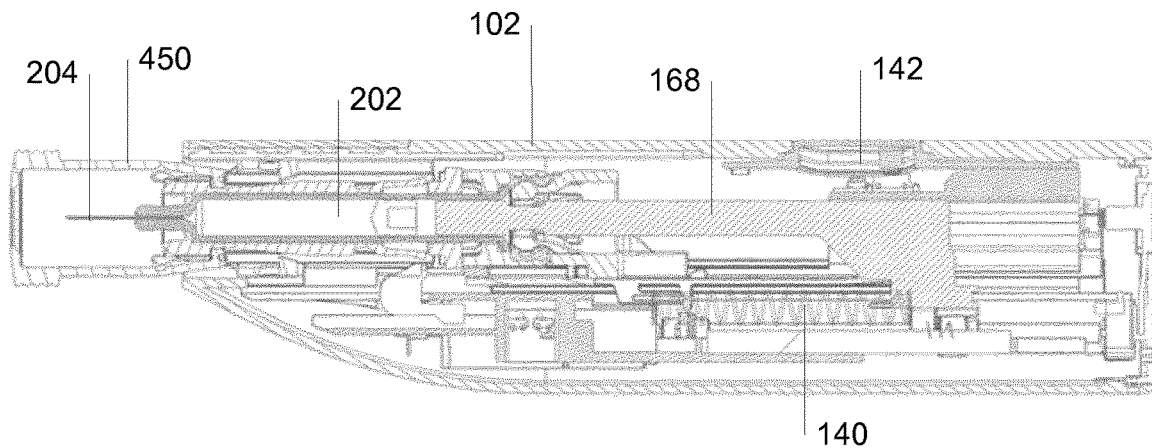
Figure 23:
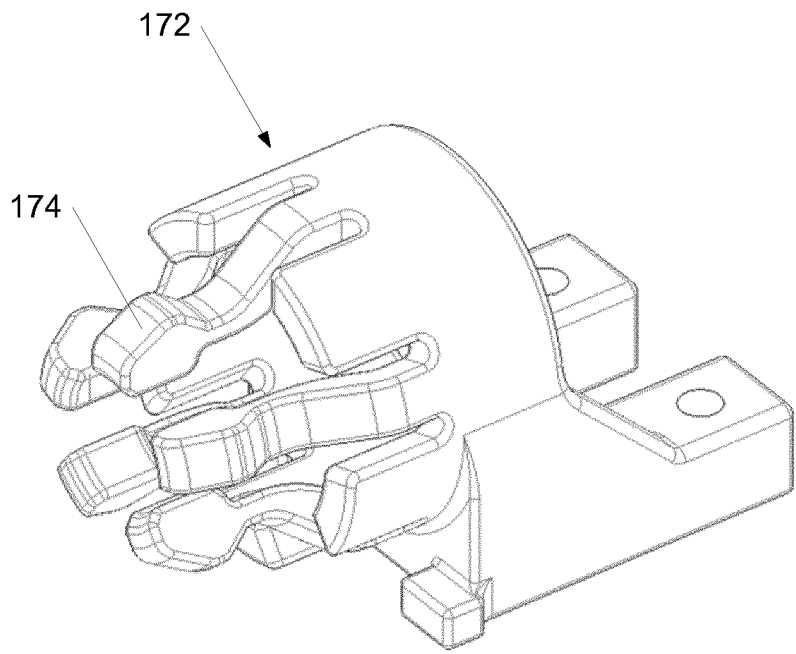
FIG. 23 show the cassette receiver in the fifth embodiment of the auto injector.
Figure 24:
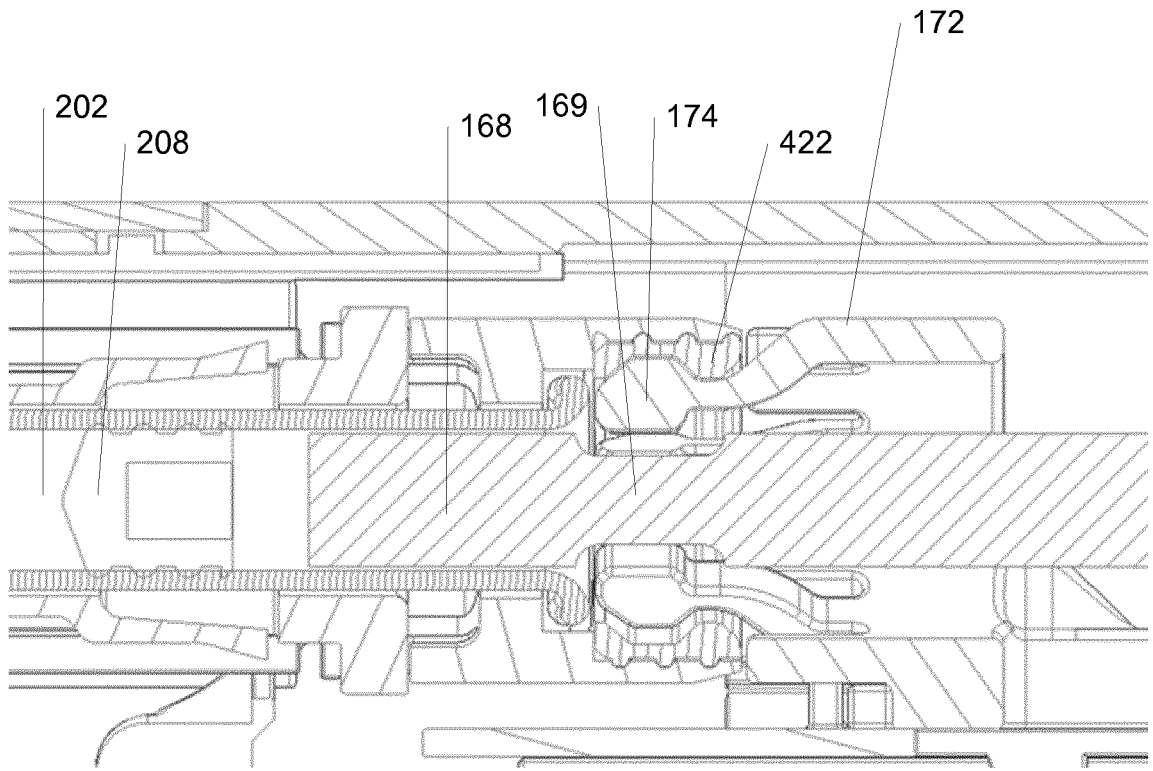
FIG. 24 show a cut-through view of the auto injector with a close-up on the connection between the cassette in the auto injector.

In FIG. 11C a cut through view of the auto injector 100*e* with the cassette 400 is shown in a perspective view. In FIG. 11D a cut through view of the auto injector 100*e* with the cassette 400 after the rigid needle shield 206 has been removed is shown in a side view. In this view, the first spring 140, which is for insertion of the needle 204, can be seen. In FIGS. 23 and 24, the connection between cassette 400 and the auto injector 100*d* is described in further details with FIG. 24 displaying the locking of the two part by a first snap fit joint.

The cassette receiver 172 shown in FIG. 11B is configured to receive a cassette 400, the piston 168 is configured for moving the stopper 208 inside the syringe 200 of the cassette 400 proximally thereby emptying the syringe of medicament, the drive module (see FIGS. 25A-B) is adapted to move the piston 168 and the cassette receiver 172. The piston and the cassette receiver can be moved together or separately by the drive module. The first spring (see FIG. 25B) is adapted for moving the syringe holder 410 with the syringe compartment 202 connected to the needle 204 proximally for insertion of the needle 204.

Due to the connection with the cassette receiver 172, the drive module 120 is further configured for moving the syringe compartment 202, the syringe holder 410 and the cassette skin sensor 450 in the distal direction relative to the rigid needle shield holder 430 and the rigid needle shield 206 thereby allowing for removal of the rigid needle shield 206.

Figure 12:
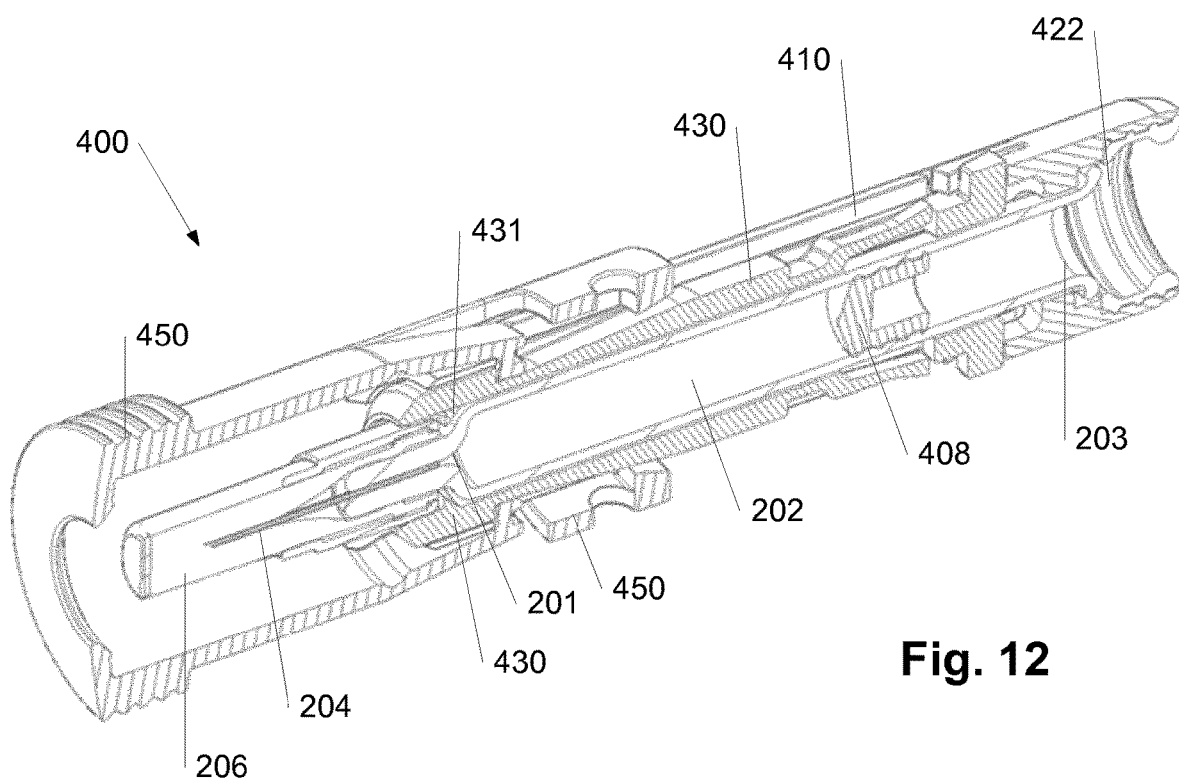
FIG. 12 shows a close-up of the cassette.

FIG. 12 shows a close-up of the cassette 400, which comprises a syringe compartment 202 containing the medicament and extending from a proximal end 201 to a distal end 203, a hollow needle 204 in fluid connection with the proximal end 201 of the syringe compartment 202, a rigid needle shield 206 connected to the proximal end 201 of the syringe compartment 202 and covering the hollow needle 204, and a stopper 208 movable from a distal position to a proximal position inside the syringe compartment 202 by means of the piston 168 moving the stopper 208 proximally for emptying the syringe compartment.

The cassette 400 further comprises a syringe holder 410 extending around at least part of the syringe compartment 202, a rigid needle shield holder 430 having a first part 431 positioned between the rigid needle shield and the proximal end of the syringe compartment, and a cassette skin sensor 450 positioned at the proximal end of the cassette 400. The cassette is normally absent of springs.

Figure 13:
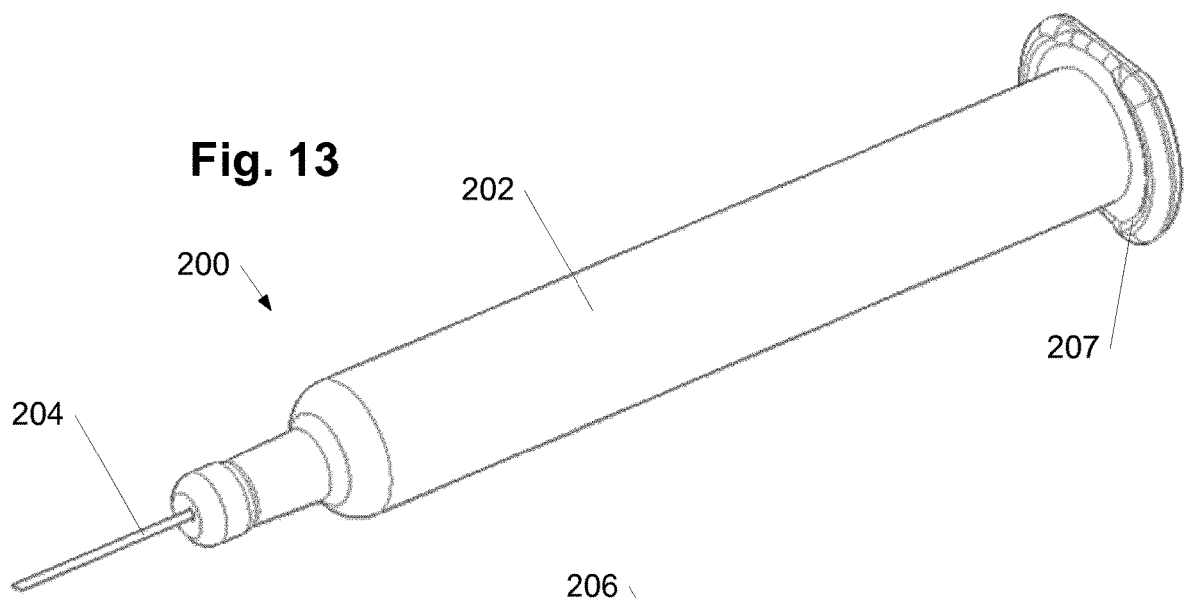
FIG. 13 shows the syringe in the cassette shown in FIG. 12.
Figure 14:
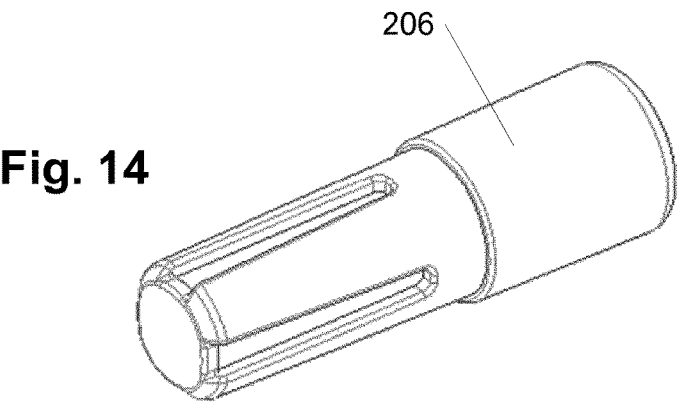
FIG. 14 shows the rigid needle shield in the cassette shown in FIG. 12.
Figure 15:
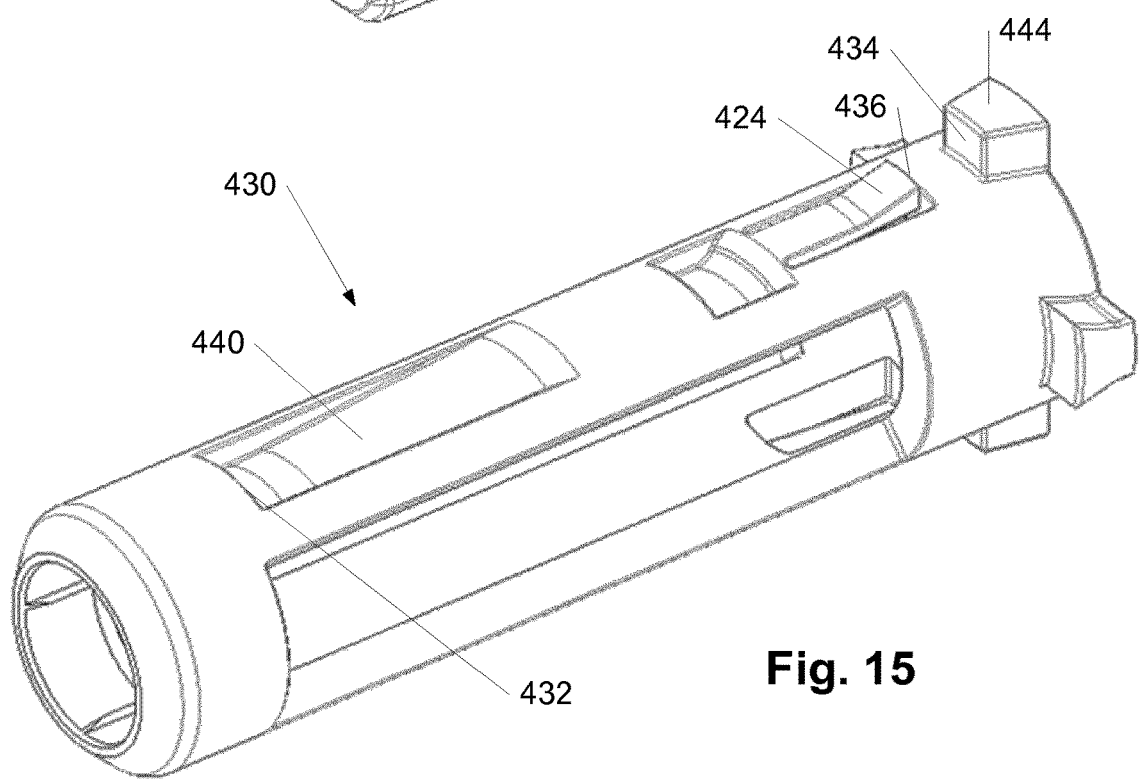
FIG. 15 shows the rigid needle shield holder in the cassette shown in FIG. 12.
Figure 16:
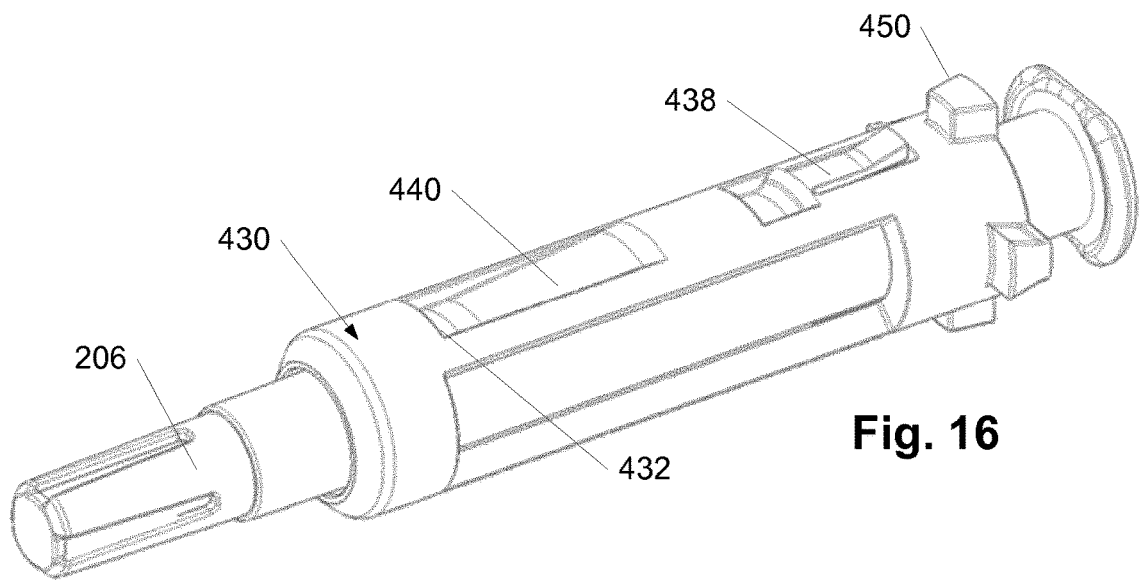
FIG. 16 shows the combination of the syringe, the rigid needle shield, and the rigid needle shield holder shown in FIGS. 13, 14, and 15, respectively.
Figure 17:
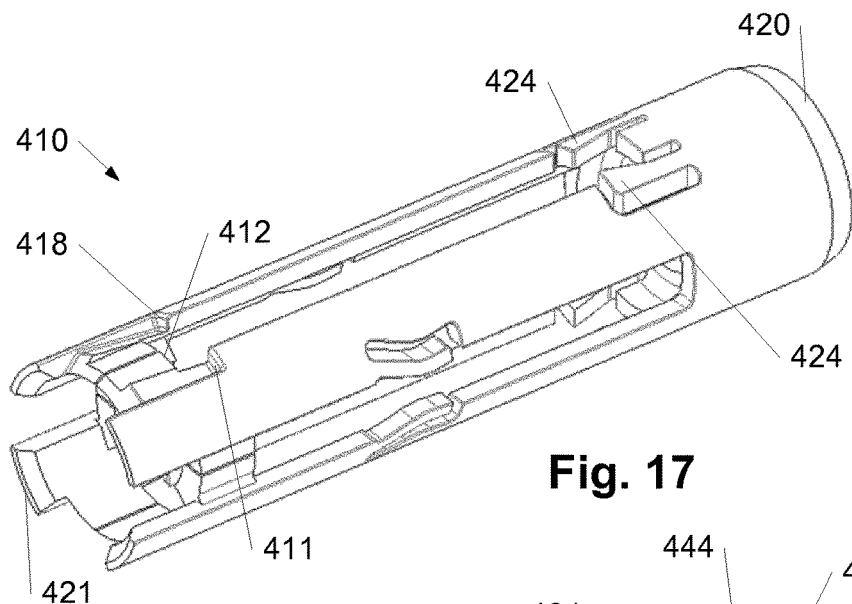
FIG. 17 shows the syringe holder in the cassette shown in FIG. 12.
Figure 18:
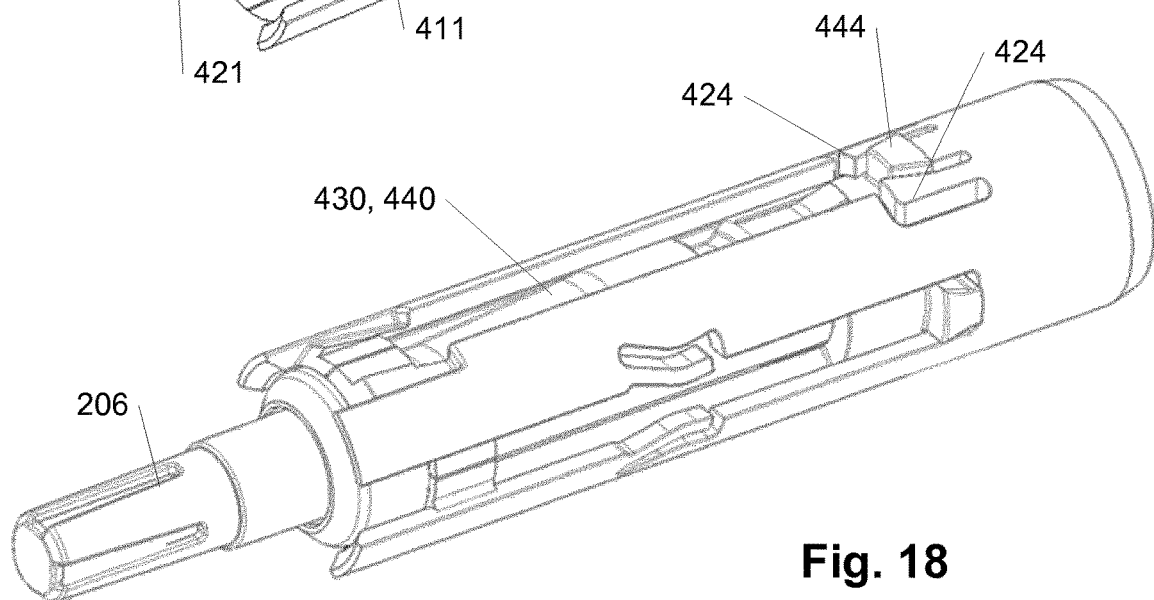
FIG. 18 shows the combination of the syringe, the rigid needle shield, the rigid needle shield holder and the syringe holder shown in FIGS. 13-16.
Figure 19A:
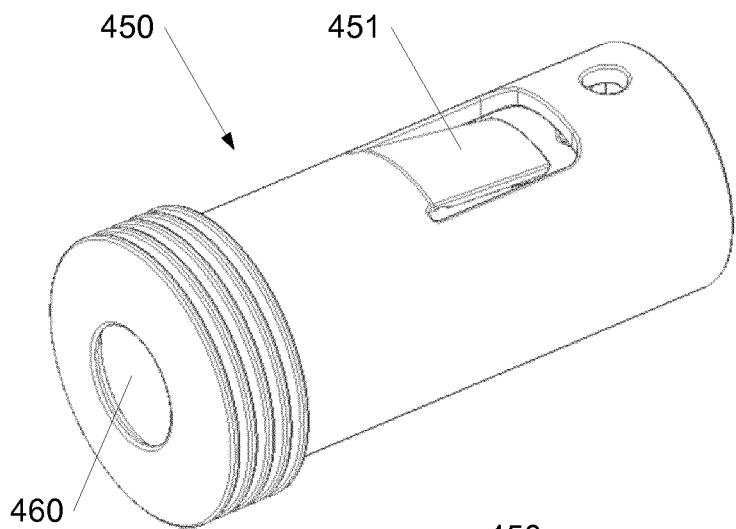
FIGS. 19A-B show the cassette skin sensor in the cassette shown in FIG. 12 with FIG. 18B being a cut-through view showing the inside of the cassette skin sensor.
Figure 19B:
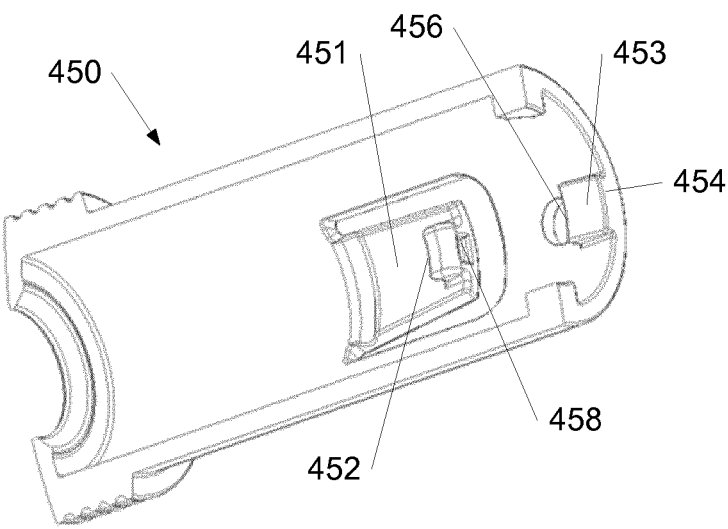

The cassette parts are shown separately and in selected combinations in the following figures, where; FIG. 13 shows the syringe 200 with the syringe compartment 202 and the needle 204, FIG. 14 shows the rigid needle shield 206, FIG. 15 shows the rigid needle shield holder 430, and FIG. 16 shows the combination of the syringe 200, the rigid needle shield 206, and the rigid needle shield holder 430. FIG. 17 shows the syringe holder 410, FIG. 18 shows the combination of the syringe 200, the rigid needle shield 206, the rigid needle shield holder 430 and the syringe holder 410. FIGS. 19A-B show the cassette skin sensor with FIG. 18B being a cut-through view showing the inside of the cassette skin sensor.

Figure 20:
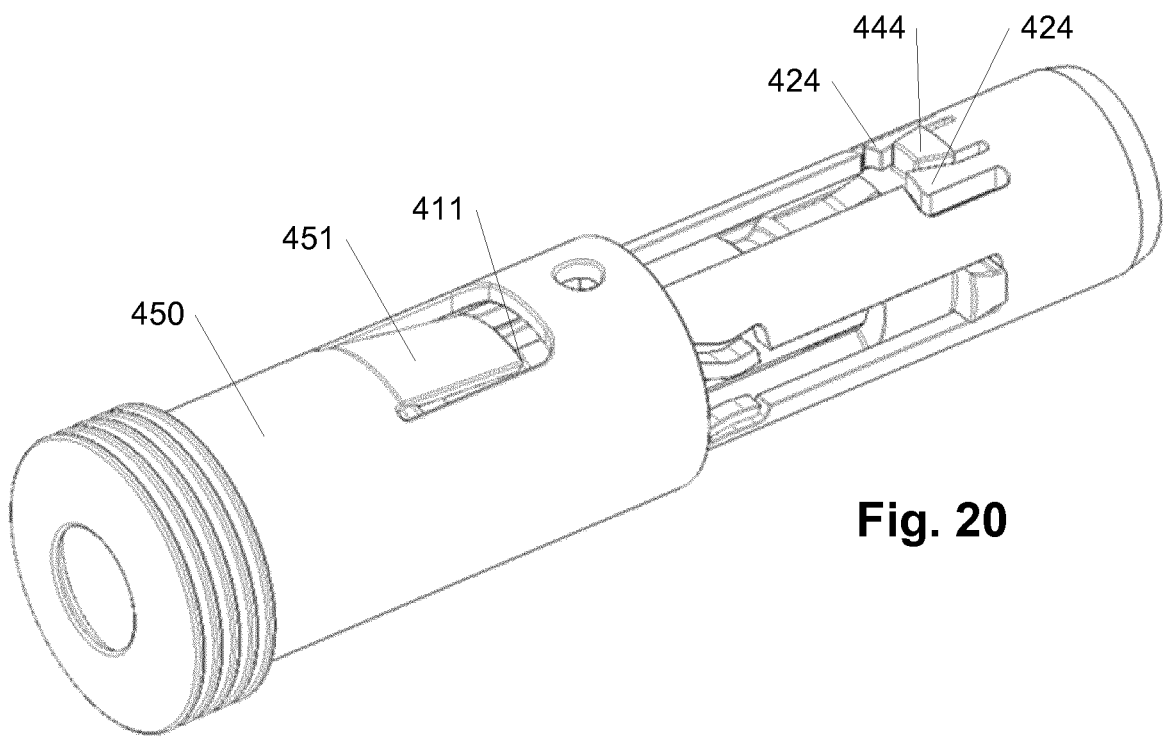
FIG. 20 shows the combination of the syringe, the rigid needle shield, the rigid needle shield holder, the syringe holder and the cassette skin sensor shown in FIGS. 13-19B.
Figure 21:
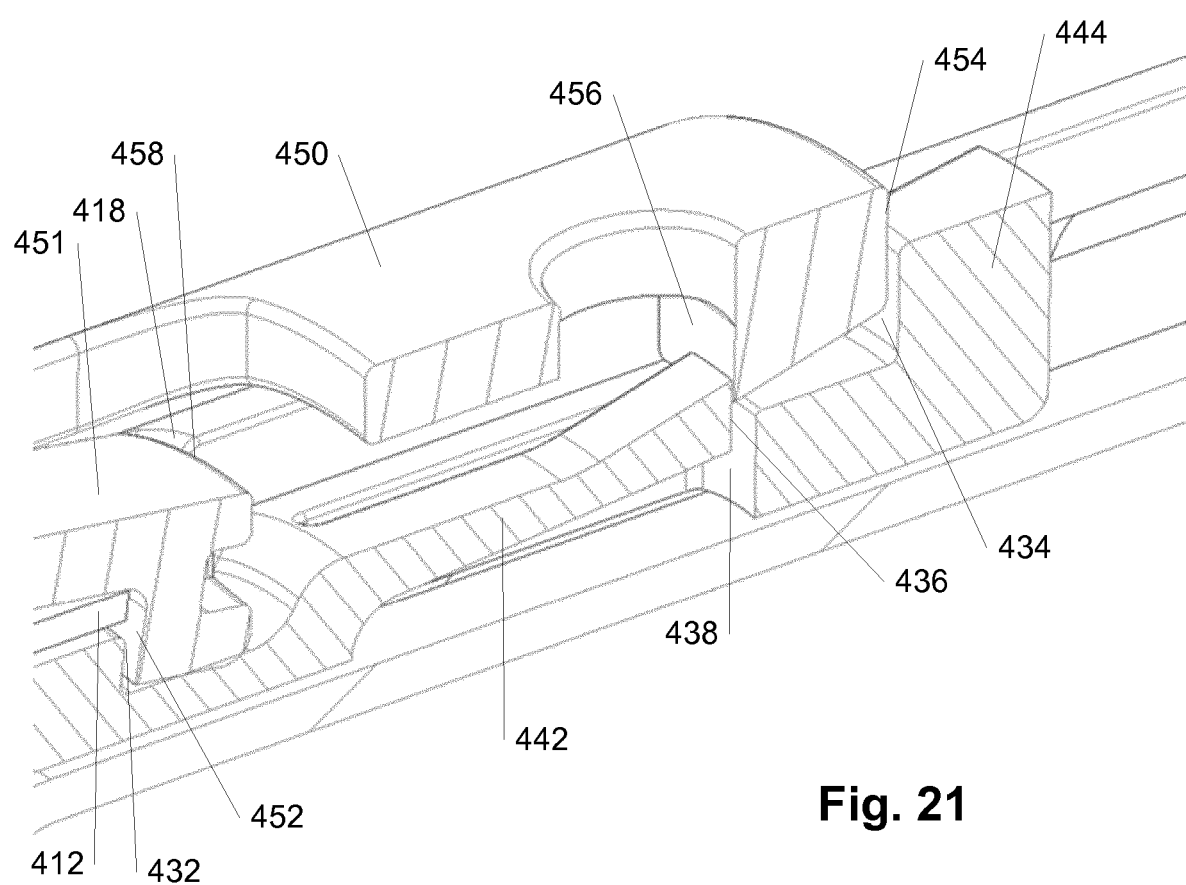
FIG. 21 shows a close-up of the cassette in a position where the cassette skin sensor, the rigid needle shield holder and the syringe holder are locked together.

FIG. 20 shows the combination of the syringe 200, the rigid needle shield 206, the rigid needle shield holder 430, the syringe holder 410 and the cassette skin sensor 450, and FIG. 21 shows a close-up of the cassette 400 in a position where the cassette skin sensor 450, the rigid needle shield holder 430 and the syringe holder 410 are locked together.

As seen in FIGS. 12-20, the rigid needle shield holder 430 is contained partly inside the syringe holder 410. Likewise, the cassette skin sensor 450 is extending partly around the syringe holder 410 and the rigid needle shield holder 430. The syringe holder 410 and the cassette skin sensor 450 are moveable in the distal direction relative to the rigid needle shield holder 430 and the rigid needle shield 206.

The cassette skin sensor 450 covers the rigid needle shield 206 in the first position shown in FIG. 12, which corresponds to the cassette 400 before being placed in the auto injector 100*d*. When the cassette 400 has been placed in the auto injector 100*e*, the drive module 120 of the auto injector 100*d* moves the cassette skin sensor 450 in the distal direction relative to the rigid needle shield 206. This exposes the rigid needle shield 206 since it is held in position by the rigid needle shield holder 430. In this second position, at least a proximal part of the rigid needle shield 206 is exposed allowing the rigid needle shield 206 to be removed by the user.

The rigid needle shield holder 430 is attached to the syringe holder 410 by a second snap joint 424, 444, which can be seen in FIG. 18. The syringe holder 410 comprises one or more proximally extending arms 424 as also seen in FIG. 17. As seen in FIG. 15, the rigid needle shield holder 430 comprises one or more distally extending protrusions 444. FIG. 18 shows how the one or more proximally extending arms 424 of the syringe holder 410 locks to the one or more distally extending protrusions 444 of the rigid needle shield holder 430 thereby forming the second snap joint 424, 444. The second snap joint 424, 444 is released upon movement of the syringe holder 410 distally relative to the rigid needle shield holder 430. Normally, the auto injector 100*e* comprises a chassis adapted for retaining the rigid needle shield holder 430 while the syringe holder 410 is moved distally thereby releasing the second snap fit.

The cassette skin sensor 450 is locked to the syringe holder 410 by a third snap joint 411, 451 as shown in FIG. 20. The third snap joint is formed by a first support surface 411 on the syringe holder 410 and an arm 451 on the cassette skin sensor 450, wherein the arm 451 of the cassette skin sensor 450 rests against the first support surface 411 of the syringe holder 410 thereby forming the third snap joint 411, 451. The third snap joint is released by movement of the cassette skin sensor 450 distally relative to the rigid needle shield holder 430. More specifically, the arm 451 of the cassette skin sensor 450 is released from the first support surface 411 of the syringe holder 410 by an inclining surface 440 on the rigid needle shield holder 430. The surface 440 on the rigid needle shield holder 430 is clearly visible in FIG. 16 and FIG. 19B shows the internal side of the arm 451 on the cassette skin sensor 450, which shows the first proximal surface 452 of the arm 451.

After the stopper 208 has been moved proximally for emptying the syringe compartment 202, a second spring in the auto injector 100e exerts a pressure on the cassette skin sensor 450 in the proximal direction. This locks the cassette skin sensor 450, the rigid needle shield holder 430, and the syringe holder 410 to each other positioning the cassette skin sensor 450 in a proximal position covering the needle 204. This prevents the user from accidentally getting in contact with the needle 204 after injection. The locking can be seen in a close up in FIG. 21, and is described in detail below.

The rigid needle shield holder 430 comprises a first distal surface 432 as shown in FIGS. 15 and 16. After delivery of the medicament, the first proximal surface 452 of the cassette skin sensor arm 451 and the first distal surface 432 of the rigid needle shield holder 430 abuts thereby preventing the cassette skin sensor 450 from moving proximally in relation to the rigid needle shield holder 430.

The cassette skin sensor 450 comprises a first distal surface 454 as shown in FIG. 19B, and the rigid needle shield holder 430 comprises a first proximal surface 434 as shown in FIG. 15. After delivery of the medicament, the first distal surface 454 of the cassette skin sensor 450 and the first proximal surface 434 of the rigid needle shield holder 430 abuts thereby preventing the rigid needle shield holder 430 from moving proximally in relation to the cassette skin sensor 450.

The cassette skin sensor 450 comprises a second proximal surface 456 as shown in FIG. 19B, and the rigid needle shield holder 430 comprises a second distal surface 436 as shown in FIG. 15. After delivery of the medicament, the second proximal surface 456 of the cassette skin sensor 450 and the second distal surface 436 of the rigid needle shield holder 430 abuts thereby preventing the rigid needle shield holder 430 from moving distally in relation to the cassette skin sensor 450.

The cassette skin sensor 450 comprises a second distal surface 458 as shown in FIG. 19B, and the syringe holder 410 comprises a first proximal surface 418 as shown in FIG. 17. After delivery of the medicament, the second distal surface 458 of the cassette skin sensor 450 and the first proximal surface 418 of the syringe holder 410 abuts thereby preventing the cassette skin sensor 450 from moving distally in relation to the syringe holder 410.

The arm 451 of the cassette skin sensor 450 comprises a first proximal surface 452 as shown in FIG. 19B, and the syringe holder 410 comprises a first distal surface 412 as shown in FIG. 17. After delivery of the medicament, the first proximal surface 452 of the cassette skin sensor arm 451 and the first distal surface 412 of the syringe holder 410 abuts thereby preventing the syringe holder 410 from moving distally in relation to the cassette skin sensor 450.

The cassette 400 may further comprise a rigid needle shield sensor 446 adapted for detecting if the rigid needle shield 206 is attached to the syringe compartment 202 or not. The rigid needle shield sensor 446 is not shown in the figures, but it may easily be understood that a sensor as described in connection with FIG. 5A-C could be included in the cassette 400. The rigid needle shield sensor 446 may be connected to the rigid needle shield holder 430. In such a setup, a distal end 447 of the rigid needle shield sensor 446 may be connected to the rigid needle shield holder 430 and a proximal end 448 of the rigid needle shield sensor 446 may be in contact with the rigid needle shield 206 when the rigid needle shield 206 is connected to the syringe compartment 202. This provides a cassette with a rigid needle shield sensor similar to the one described in connection with FIG. 5A-C.

Figure 22A:
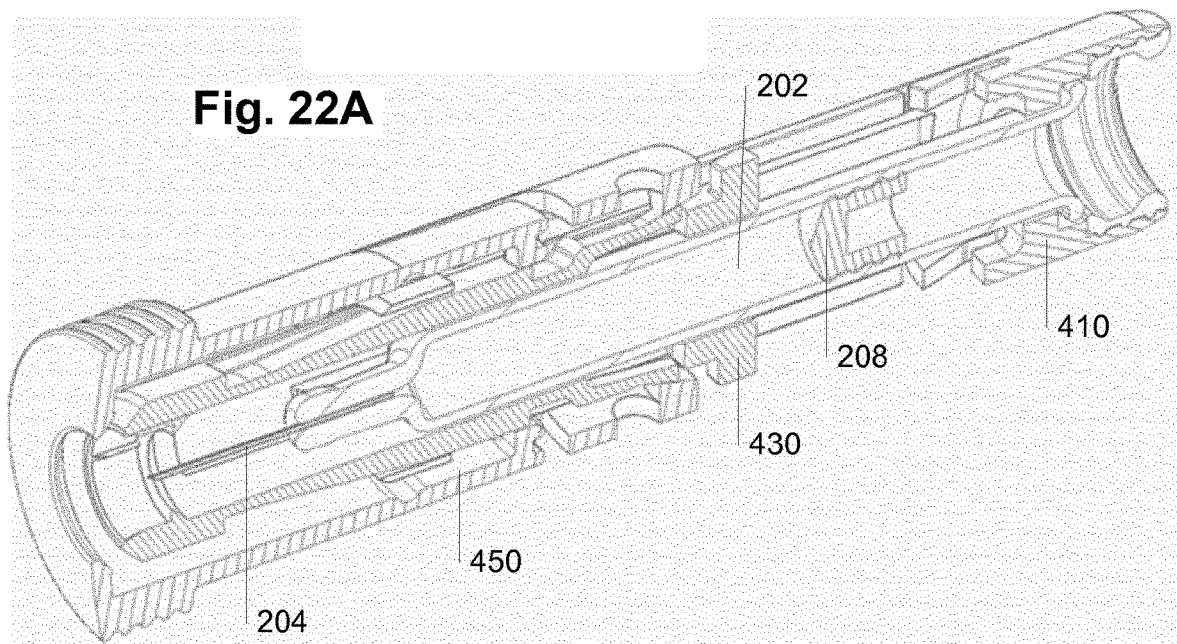
FIGS. 22A-D show the cassette during selected steps during insertion of the needle and the injection of the medicament.
Figure 22B:
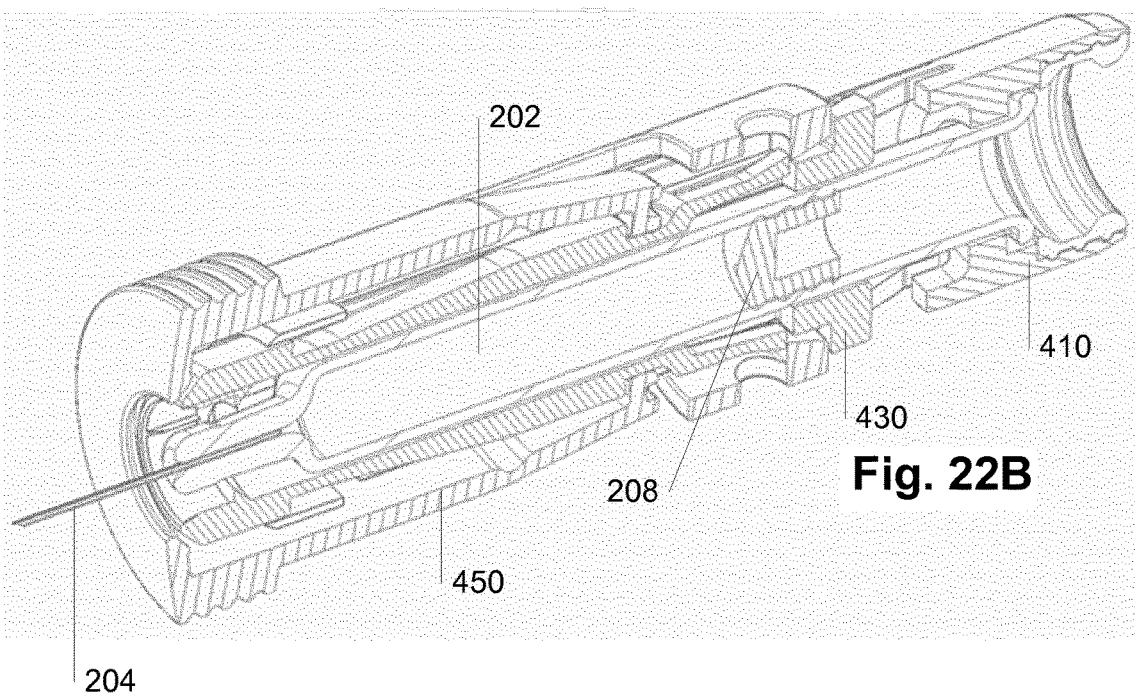
Figure 22C:
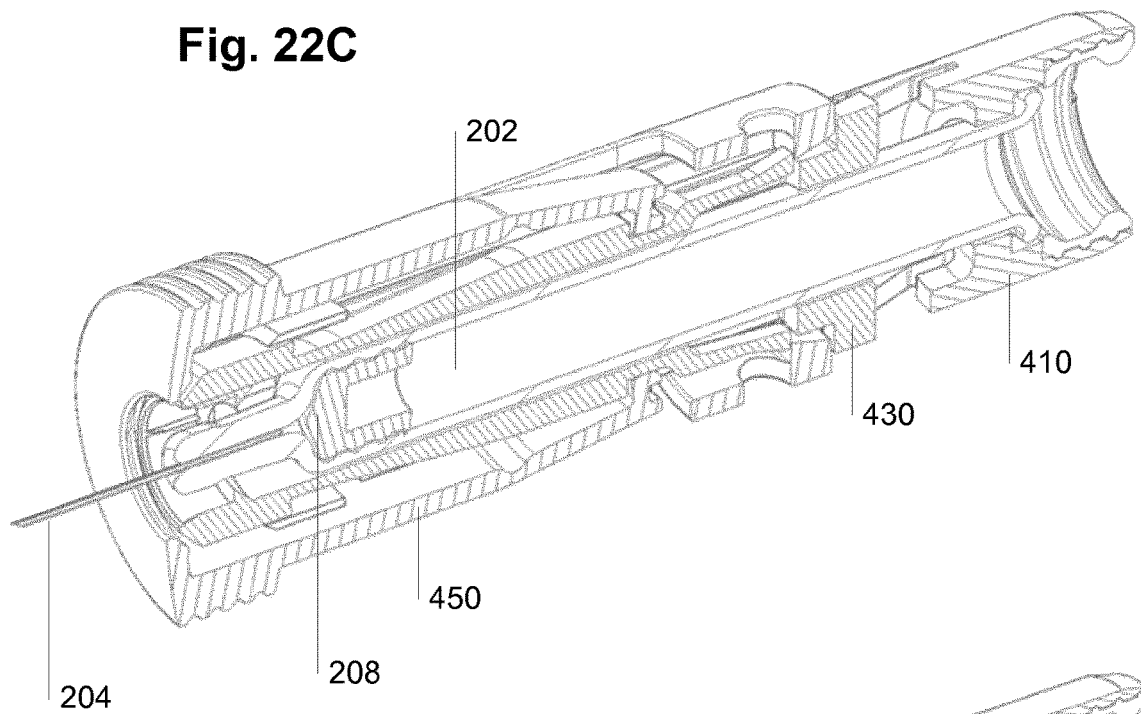
Figure 22D:
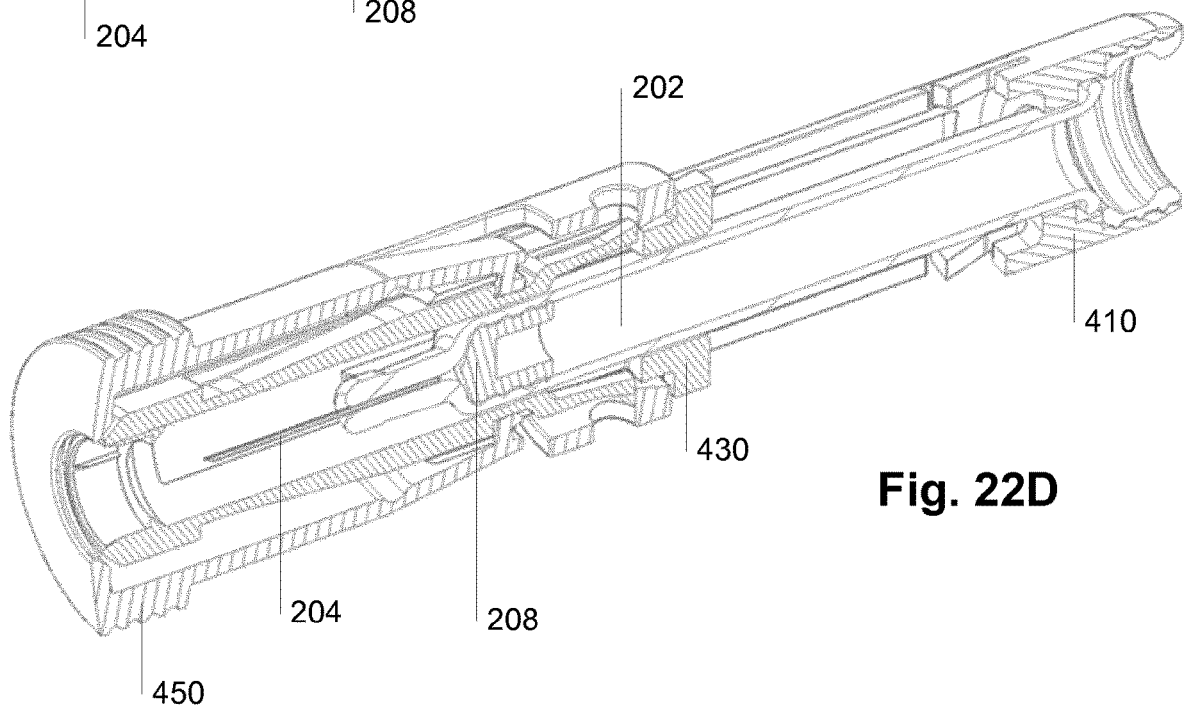

FIGS. 22A-D show the cassette 400 during selected steps during insertion of the needle and the injection of the medicament. In FIG. 22A, the cassette 400 is shown after removal of the rigid needle shield ready for insertion for the needle 204. In FIG. 22B, the syringe holder 410 has been moved proximally compared to the rigid needle shield holder 430 and the cassette skin sensor 450, whereby the needle 204 has been inserted into the patient. The medicament has not yet been delivered. In FIG. 22C, the stopper 208 has been moved forward and the medicament delivered to the patient. In FIG. 22D, the needle 204 has been retracted from the patient and the cassette skin sensor 450 and the rigid needle shield holder 430 have moved proximally in relation to the syringe holder 410, whereby the cassette skin sensor 450 is covering the needle 204. The cassette 400 is now in the locked position shown in FIG. 21.

FIG. 23 show the cassette receiver 172 in the fifth embodiment of the auto injector 100e in a close up. The distal end of the syringe holder 410 is locked to the cassette receiver 172 by a first snap joint 174, 422 when the cassette 400 is loaded into the auto injector 100e. The first snap joint is constructed such that it allows for release of the cassette 400 from the cassette receiver 172 when the piston 168 is in a first position as shown in FIG. 24. The distal end 420 of the syringe holder 410 comprises an inner recess 422, which the locking arms 174 on the cassette receiver 172 snaps into as shown in FIG. 24. The piston 168 comprises a constricted portion 169, which is positioned such that locking arms 174 on the cassette receiver 172 can be flexed thereby allowing for the syringe holder 410 to be attached to the cassette receiver 172. When the piston moves to a second position in the distal direction, the constricted portion 169 moves away from the locking arms 174. This locks the cassette 400 to the cassette receiver 172 since the locking arms 174 is now prevented from flexing, which is required in order to release the inner recess 422 from the locking arms 174.

Figure 25A:
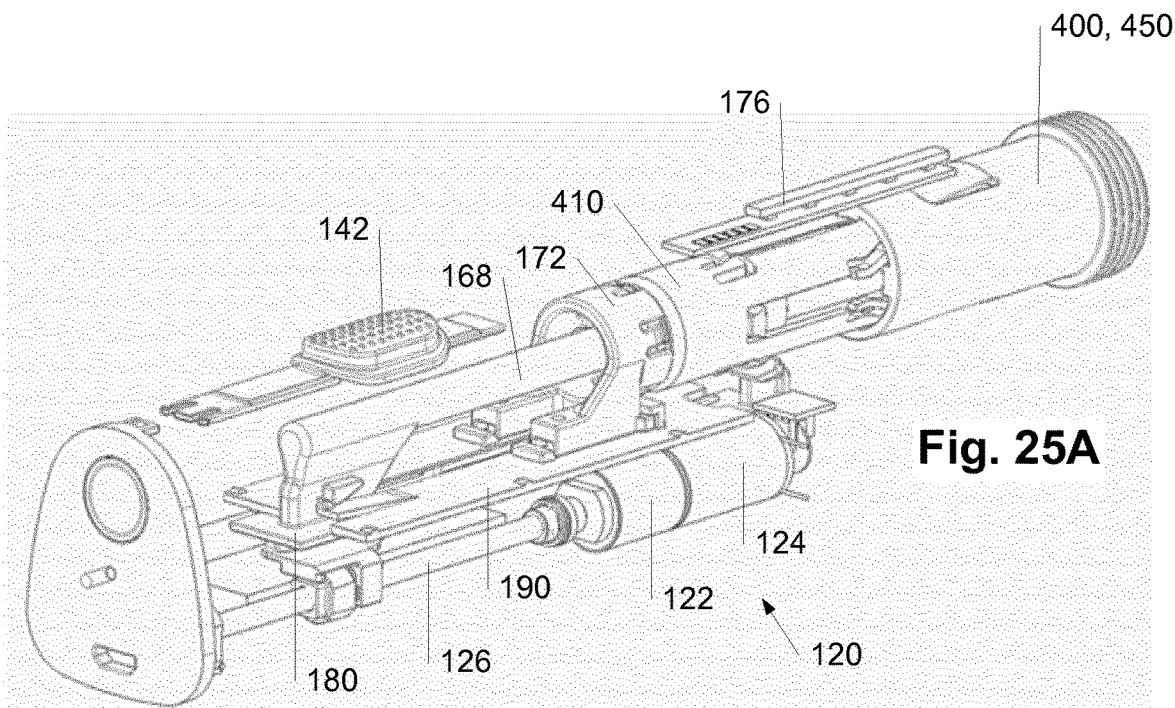
FIG. 25A shows interior parts of the fifth embodiment of the auto injector connected to a cassette in a view from the distal end.
Figure 25B:
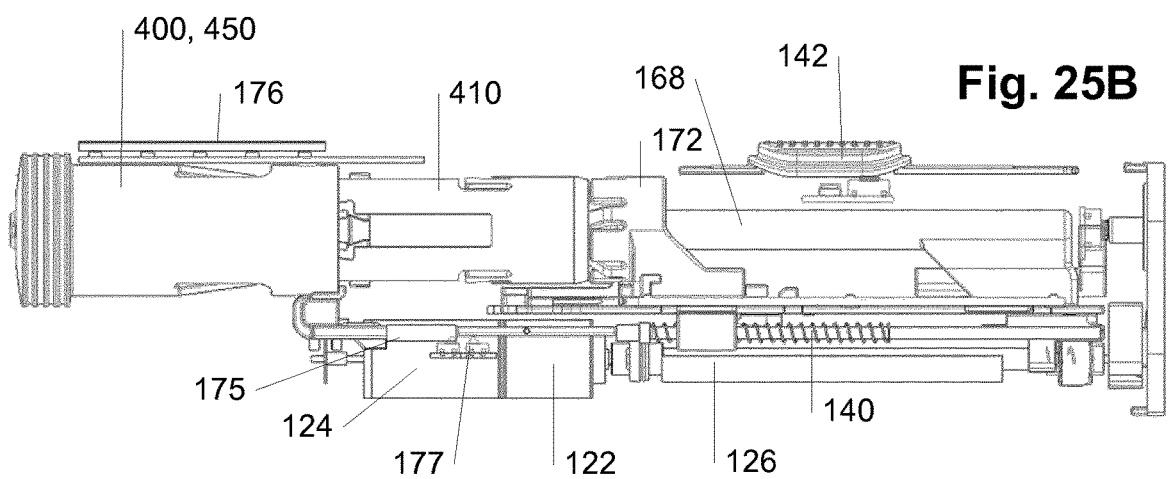
FIG. 25B shows a side cut-through view of the parts shown in FIG. 25 seen from the opposite direction.
Figure 25C:
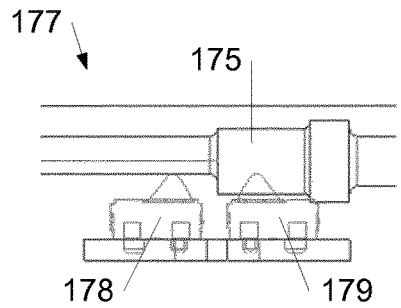
FIGS. 25C-D show enlargement views of the sensor system.
Figure 25D:
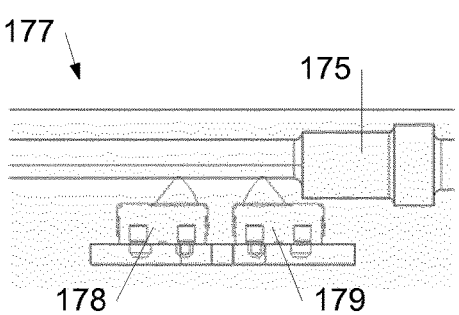

FIG. 25A shows interior parts of the auto injector 100e connected to a cassette 400 in a view from the distal end. FIG. 25B shows a side cut-through view of the parts shown in FIG. 25A. In FIG. 25A, the drive module 120 can be seen. The drive module comprises a motor 122 and a gear box 124 connected to a screw 126. The piston 168 shown in FIG. 25A is connected to a chassis 180, which in turn is connected to the drive module 120. The cassette receiver 172 connected to a slider 190 is also seen in FIG. 25A. A light panel 176 is further visible. The panel may provide the user with visual information. Alternatively, audio feedback may be provided to the user from the panel. In FIG. 25B, a sensor system 177 comprising a skin sensor switch 178 and a cassette sensor switch 179 is also seen. FIGS. 25C-D show enlargement of the sensor system 177. In FIG. 25C, the skin sensor switch 178 is open and cassette sensor switch 179 is close corresponding to the situation where no cassette 400 is placed in the auto injector 100e. In FIG. 25D, the skin sensor switch 178 and cassette sensor switch 179 are both is open corresponding to the situation where a cassette 400 has been placed in the auto injector 100e. The switches are opened and closed as an actuator component 175 is being pushed in the longitudinal direction by the skin sensor 450 in the cassette 400.

Figure 26A:
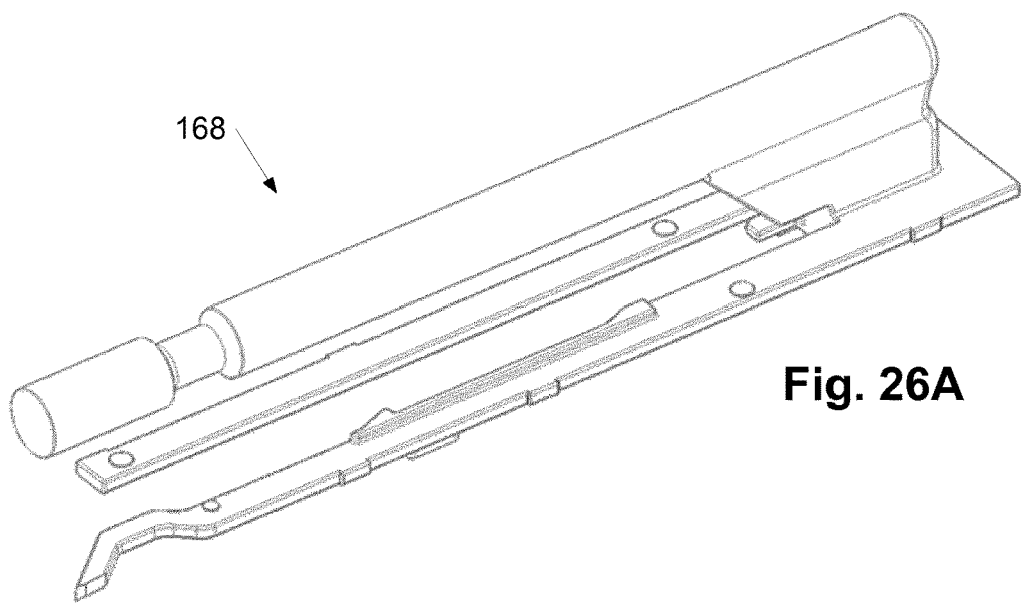
FIG. 26A shows the piston in the auto injector in the fifth embodiment.
Figure 26B:
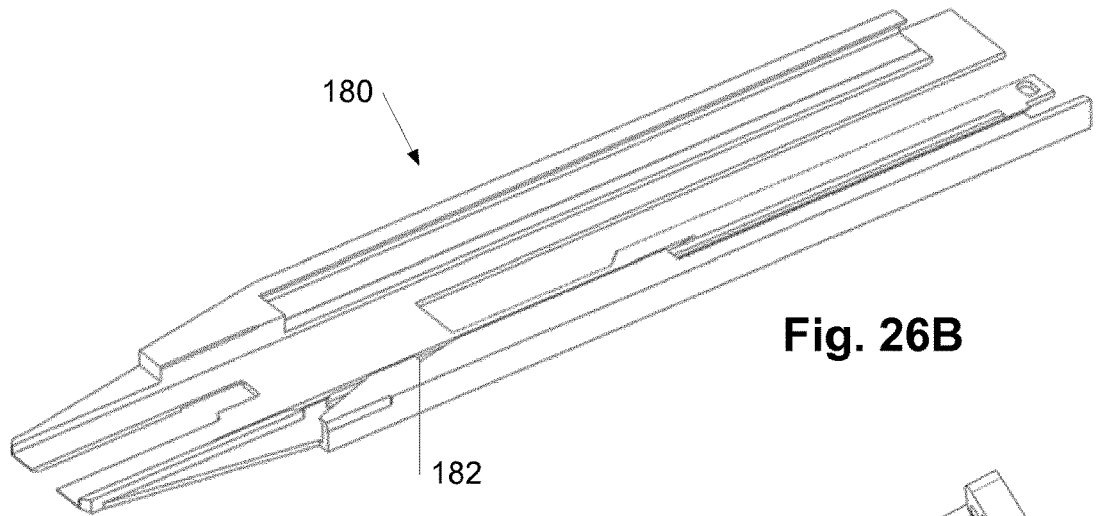
FIG. 26B shows the chassis in the auto injector in the fifth embodiment
Figure 26C:
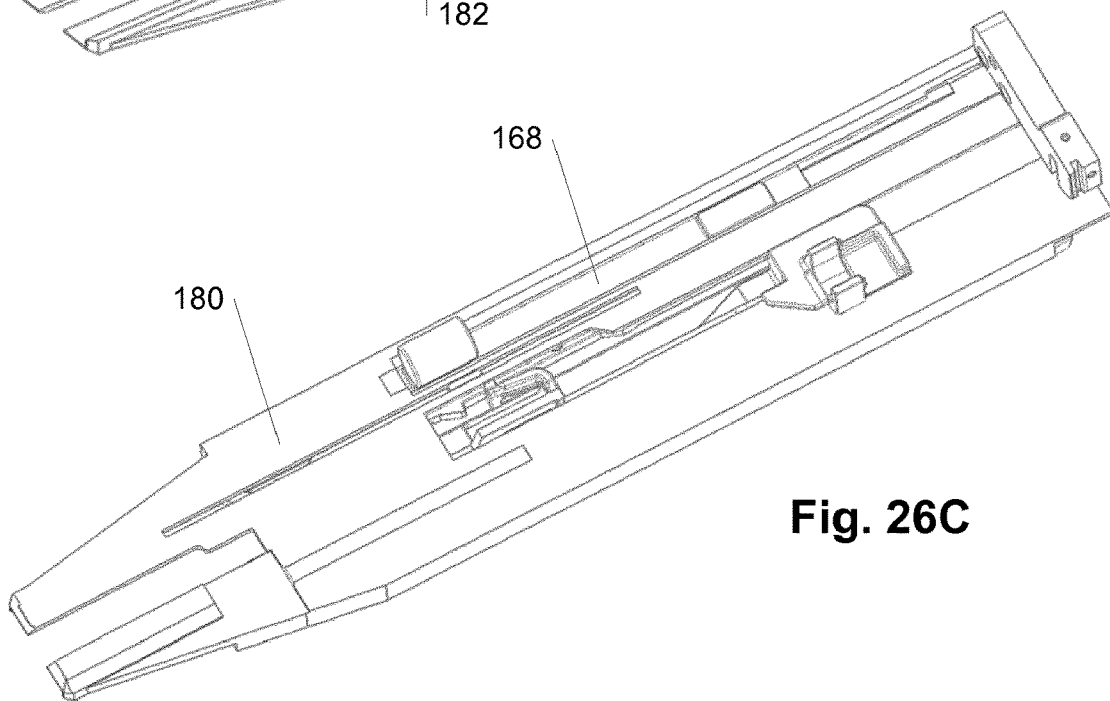
FIG. 26C shows the piston of FIG. 26A connected to the chassis of FIG. 26B in a bottom-up view.

FIG. 26A shows the piston 168, FIG. 26B the chassis 180 and FIG. 26C shows the piston 168 connected to the chassis 180 in a bottom-up view.

Figure 27:
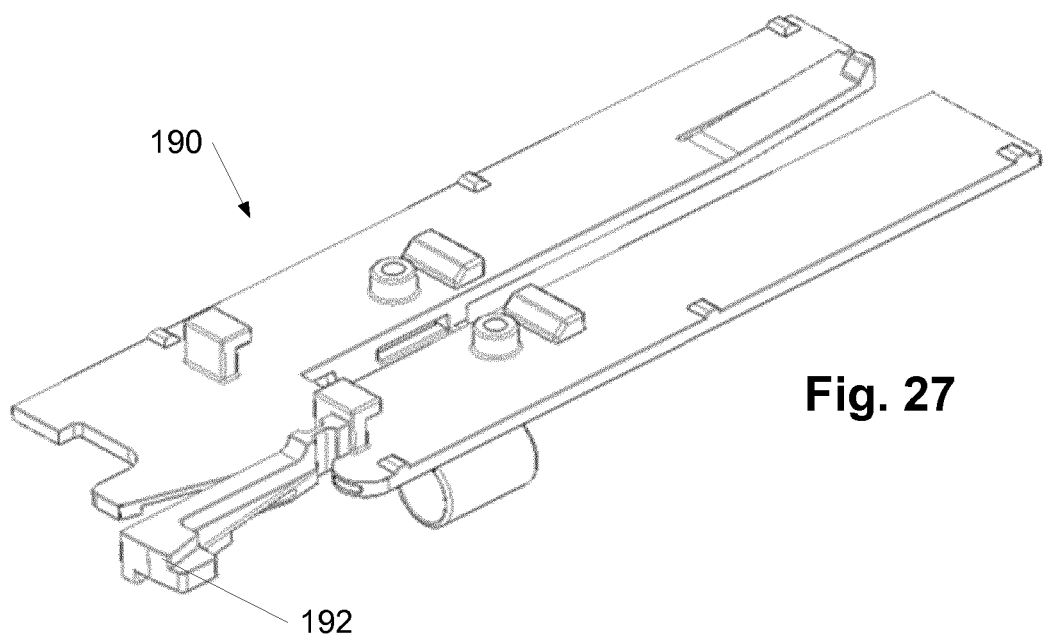
FIG. 27 shows the slider in the auto injector in the fifth embodiment.
Figure 28:
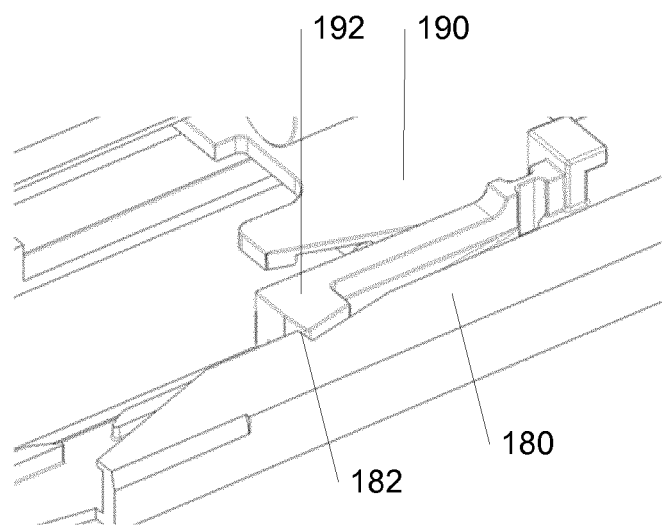
FIG. 28 shows close-up of the chassis and the slider locked together.

FIG. 27 shows the slider 190 to which the cassette receiver 172 (not shown in the figure) is attached. FIG. 28 shows close-up of the chassis 180 and the slider 190 locked together. The chassis 180 comprises a locking surface 182, which a locking arm 192 on the slider 190 abuts creating a locked connection. When the drive module 120 moves the chassis 180 with the piston 168 in the distal direction after loading of a cassette 400 in the auto injector 100e, the locking surface 182 comes in contact with the locking arm 192 on the slider 190, the slider 190 is also moved distally. In this position, the piston 168 has reached a position where it non-releasable locks the cassette to the cassette receiver 172. The rigid needle shield holder 430 (not shown in this figure) is resting against a hard stop in the chassis and cannot move into the auto injector 100e. The remaining components of the cassette can move into the auto injector 100e, when the slider 190 moves proximally.

Upon activation of the activation button 142, the drive module 120 moves the chassis 180 proximally for insertion of the needle and injection of medicament. The locking arm 192 is released from the locking surface 182 during this movement allowing the first spring 140 to push the slider 190 with the cassette 400 forward thereby inserting the needle 204. The drive module 120 continues to move the chassis with the plunger rod forward in the proximal direction. When the piston 168 catches up with the cassette 400, it continues to move the stopper 208 in the proximal direction thereby delivering the medicament to the patient. The first spring 140 is thereby moving at a needle insertion speed, and the drive module is moving the piston at a medicament delivery speed, wherein the needle insertion speed is larger than the medicament delivery speed, whereby the piston 168 and the stopper 208 is separated in the longitudinal direction during and for a time period after insertion of the needle 204 before the piston 168 catches up with the syringe compartment 202. This is also shown and discussed in connection with FIGS. 9A-D.

The auto injector may further comprising a second spring exerting a pressure on the cassette skin sensor 450 in the proximal direction after removal of the auto injector 100e from the skin post injection of the medicament. This pushes the skin sensor 450 in the proximal direction locking the cassette parts together as described in connection with FIG. 21.

Figure 29A:
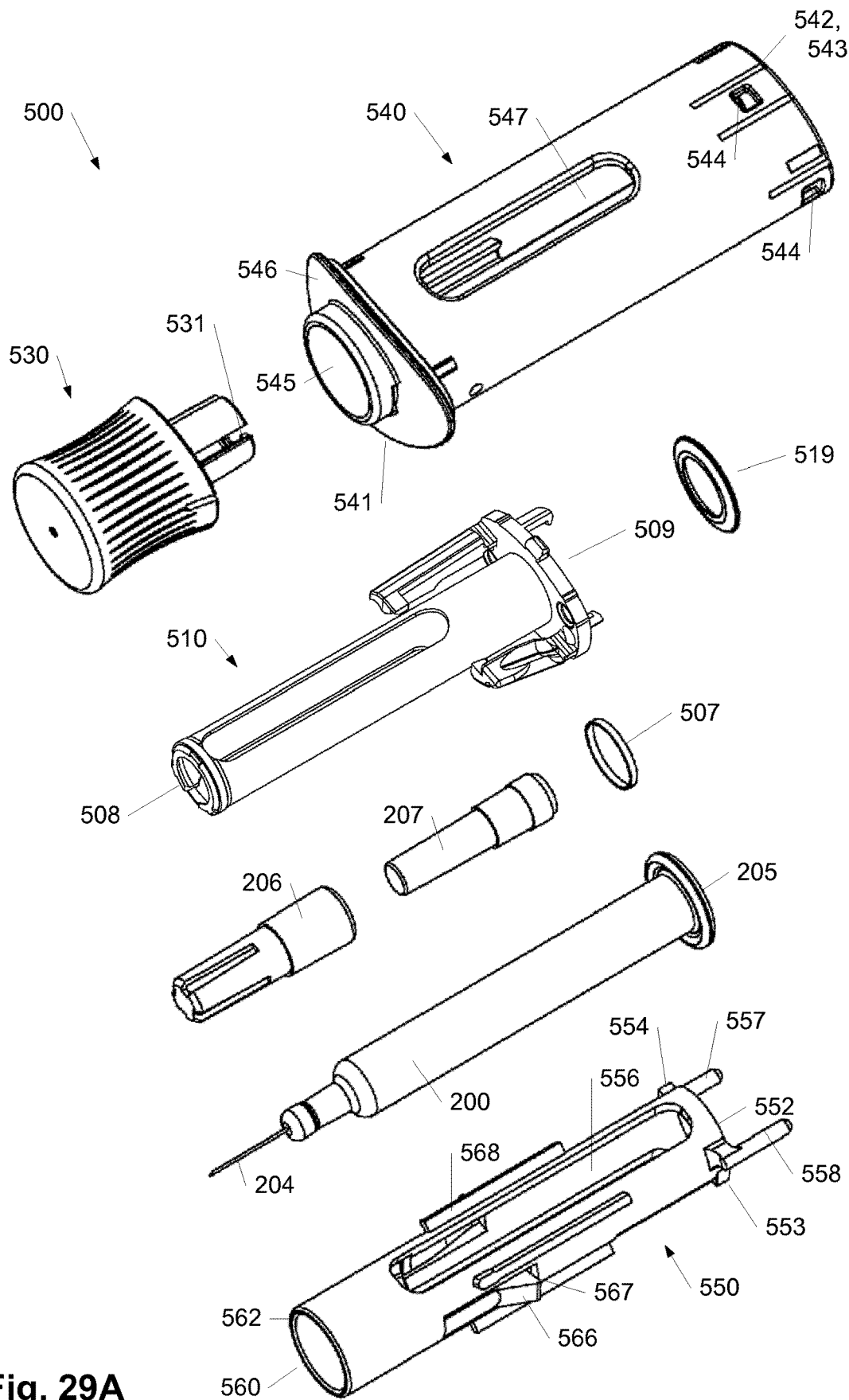
FIG. 29A shows a sixth embodiment of a cassette in an exploded view.

FIG. 29A shows a sixth embodiment of a cassette 500 in an exploded view. The auto injector 100f for receiving the cassette 500 is shown in FIGS. 31-35. Like in the previously described embodiments, a syringe 200 with a syringe compartment 202 containing the medicament, a hollow needle 204 in fluid connection with the syringe compartment, a rigid needle shield 206 connected to the proximal end of the syringe compartment and covering the hollow needle, and a stopper 208 movable from a distal position to a proximal position inside the syringe compartment 202 by means of a piston in the auto injector.

The needle shield 206 shown in FIG. 29A has both an outer part 206, and an inner part 207. The parts may normally be a connected or even produced as a one-piece item.

Positioned around the syringe 200 is a syringe holder 510 extending around at least part of the syringe compartment 202. The syringe holder 510 has a syringe holder support tube 511, which supports the syringe compartment 202. The tube 511 has an opening for inspection of the medicament in the syringe compartment 202. The syringe 200 is fixed inside the syringe holder 510 at the end 205 of the syringe 200, which has a collar-like shape. A ring-shaped syringe holder part 519 may be used for securing the syringe 200 inside the syringe holder 510. This may also be omitted.

The cassette 500 comprises a cassette housing 540 extending from a proximal end 541 to a distal end 542. The cassette housing 540 is oval, which helps ensure an accurate positioning of the cassette 500 inside the auto injector 100f. The oval shape may also make the cassette more compact.

The cassette housing 540 is enclosing a cassette skin sensor 550. At the proximal end 541 of the cassette housing 540 is a housing shoulder 546 with an opening 545 through which the cassette skin sensor 550 can extend. The cassette housing 540 have internal protruding rails 548 (not shown in the figure) on its inside for guiding the skin sensor 550. The two parts 540, 550 are movable in relation to each other in an unlocked configuration. The cassette skin sensor 550 is positioned such that it extends proximally from the cassette housing 540.

The cassette housing 540 has a distal end surface 543 with a skin sensor housing opening 545 through which the cassette skin sensor 550 extends. This is most clearly seen in the cut-through images, e.g. in FIG. 30. The cassette housing 540 has an opening 547 in the longitudinal direction for inspection of the medicament in the cassette 500.

The cassette skin sensor 550 has two pins; a first cassette skin sensor pin 557 and a second cassette skin sensor pin 558, extending from the distal end 552 of the cassette skin sensor 550.

Figure 29B:
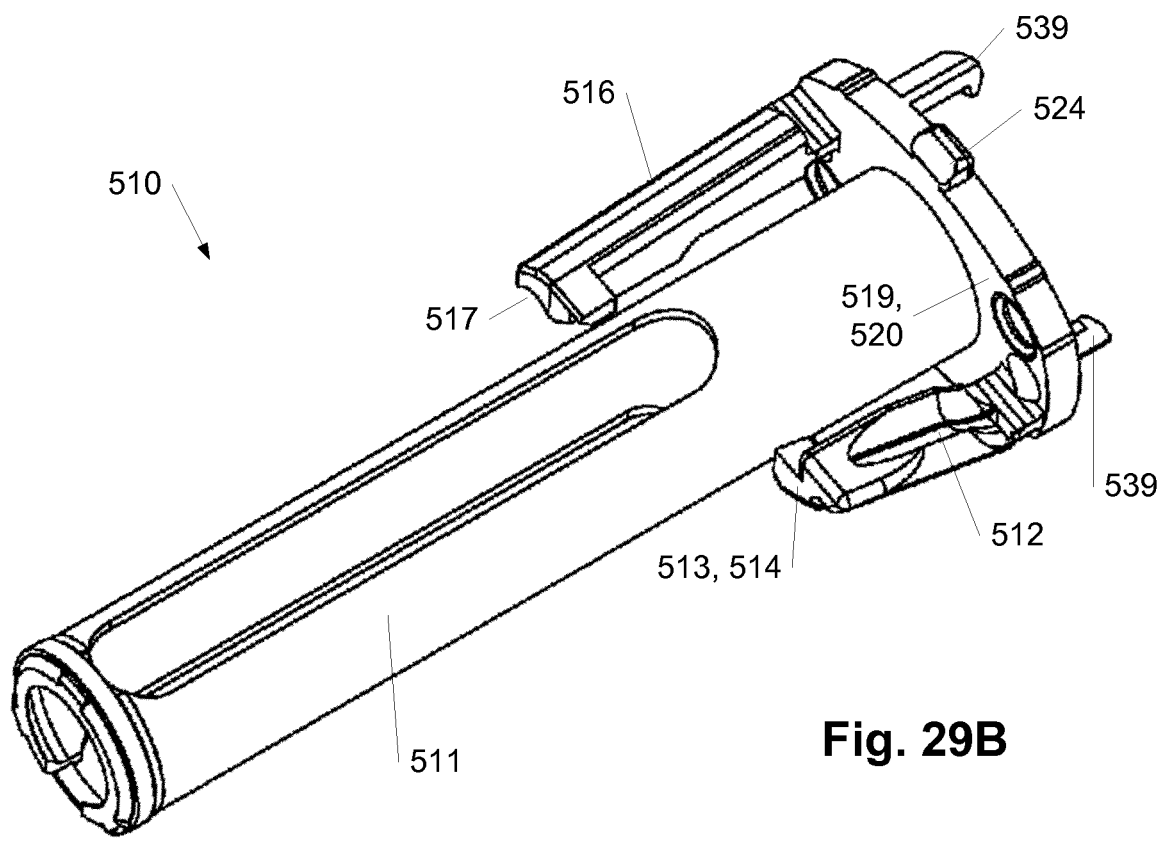
FIGS. 29B-C show a close-up of the syringe holder from two different directions.
Figure 29C:
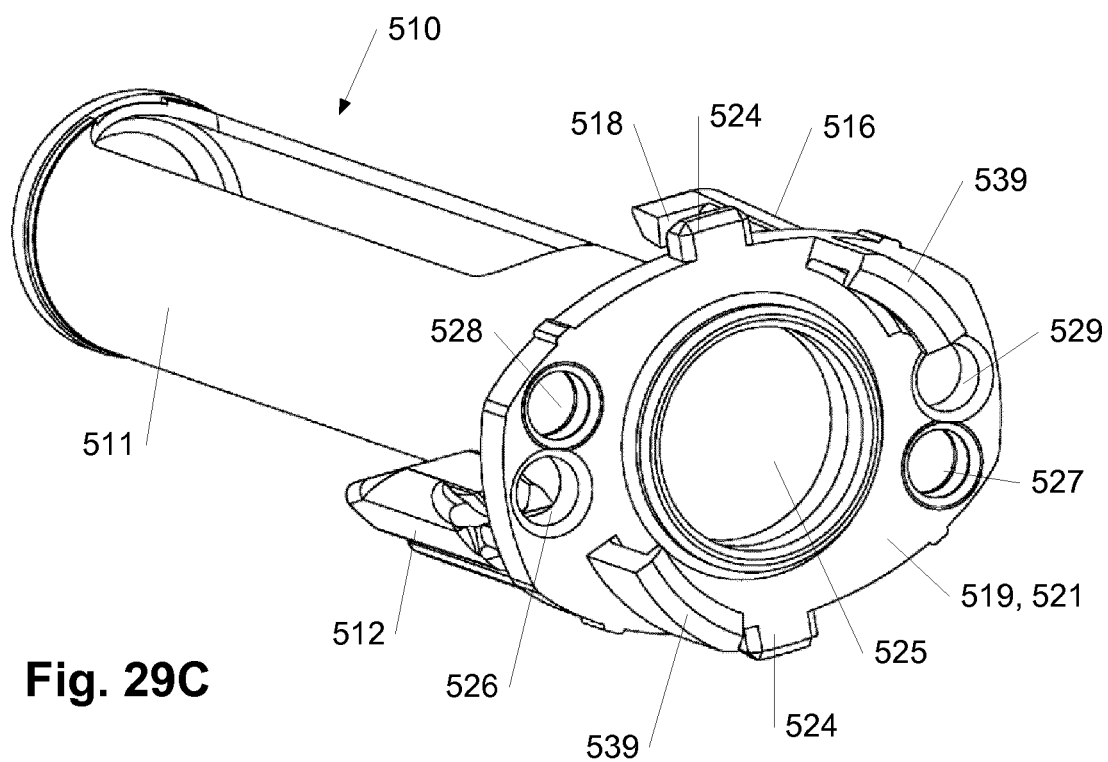

The cassette skin sensor 550 covers at least part if not the majority of a syringe holder 510, which is shown in more details in FIGS. 29B-C in a front-end and a rear-end perspective view. The syringe holder 510 has an elongated support tube 511 with an opening for inspection of the medicament. At the distal end 509 of the syringe holder 510 is a ring-shaped syringe holder part 519, which has a number of openings including: a first pin opening 526, a second pin opening 527, a third pin opening 528, a fourth pin opening 529, and a piston opening 525. It is through the piston opening 525 that the auto injector piston 1168 extends when medicament is delivered to the patient.

The syringe holder 510 also comprises a first syringe holder arm 512 extending in a proximal direction from the ring-shaped syringe holder part 519. The first syringe holder arm 512 has a proximal surface 514 at the proximal end of the arm 512. When the cassette skin sensor 550 and the syringe holder 510 are in a first position, a first locking protrusion 553 on the cassette skin sensor 550 engages with the proximal surface 514. This engagement of the first locking protrusion 553 and the proximal surface 514 prevents movement of the cassette skin sensor 550 towards the syringe holder 510. The first syringe holder arm 512 is flexibly connected to the ring-shaped syringe holder part 519.

The syringe holder 510 also comprises a syringe holder ring 507, which locks the syringe 200 inside the syringe holder 510.

When the cassette 500 is positioned in the auto injector 100f, the first pin opening 526 allows for passage of a first skin sensor release pin 1156 of the auto injector 100f there through. This is seen and described in connection with e.g. FIGS. 35A-F. When the first skin sensor release pin 1156 of the auto injector 100f passes through the first pin opening 526 in the syringe holder 510, it comes in contact with the first syringe holder arm 512 and deflects it. This causes a release of the cassette skin sensor 550 allowing it to move towards the syringe holder 510, i.e. a distal direction movement of the cassette skin sensor 550. Upon movement of the cassette skin sensor 550 towards the syringe holder 510, the first cassette skin sensor pin 557 moves towards—and possibly through—the second pin opening 527 in the syringe holder 510. Similarly, the second cassette skin sensor pin 558 moves towards—and possibly through—the third pin opening 528 in the syringe holder 510 when the second cassette skin sensor 558 moves distally.

The syringe holder 510 and the skin sensor 550 are longitudinally movable relative to each other upon release of the skin sensor 550 from the syringe holder 510.

Figure 35A:
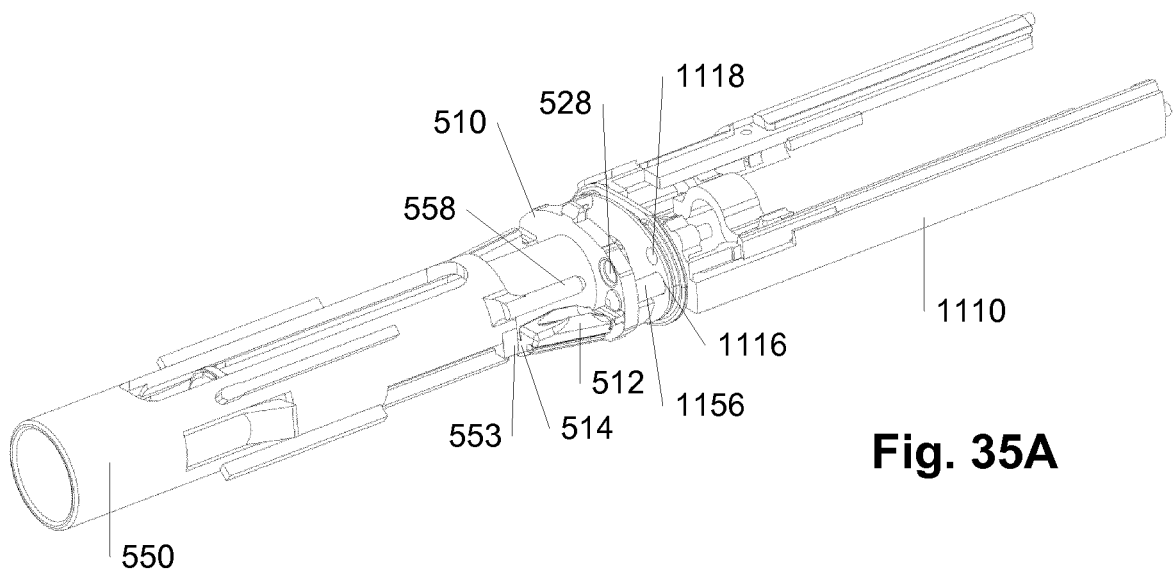
FIGS. 35A-C show the steps in releasing the cassette skin sensor from the syringe holder by means of the auto injector.
Figure 35B:
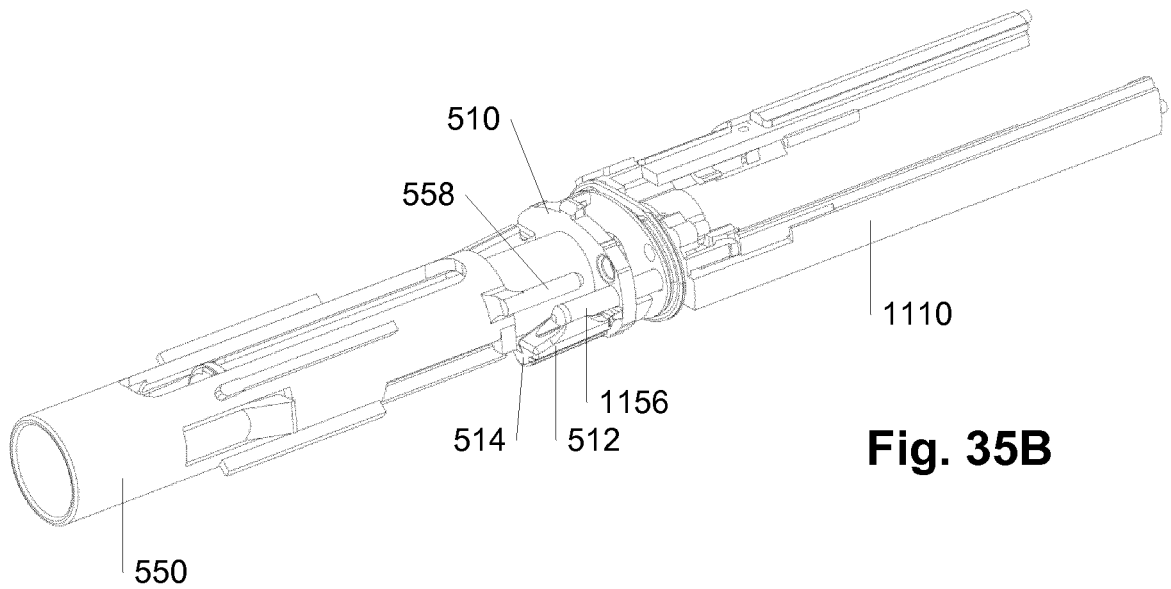
Figure 35C:
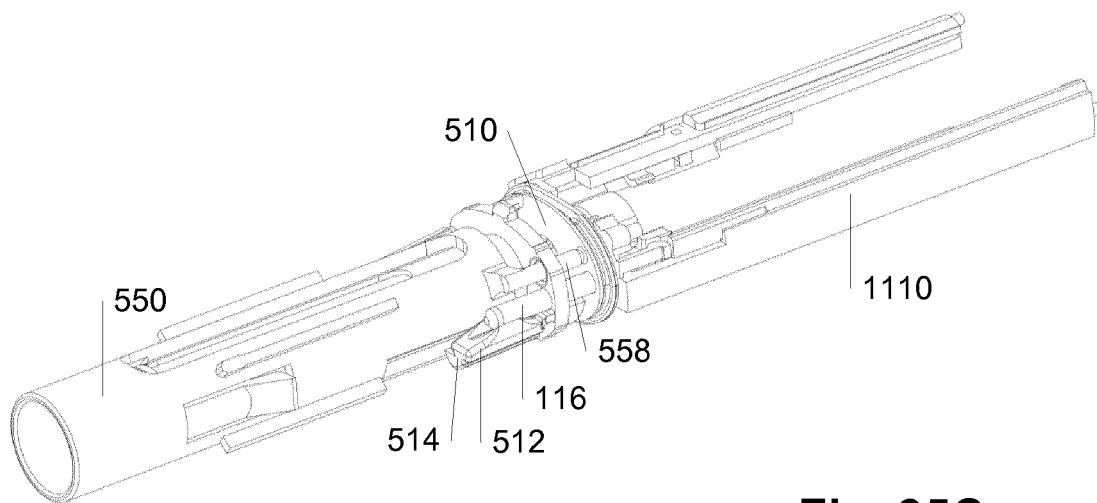
Figure 35D:
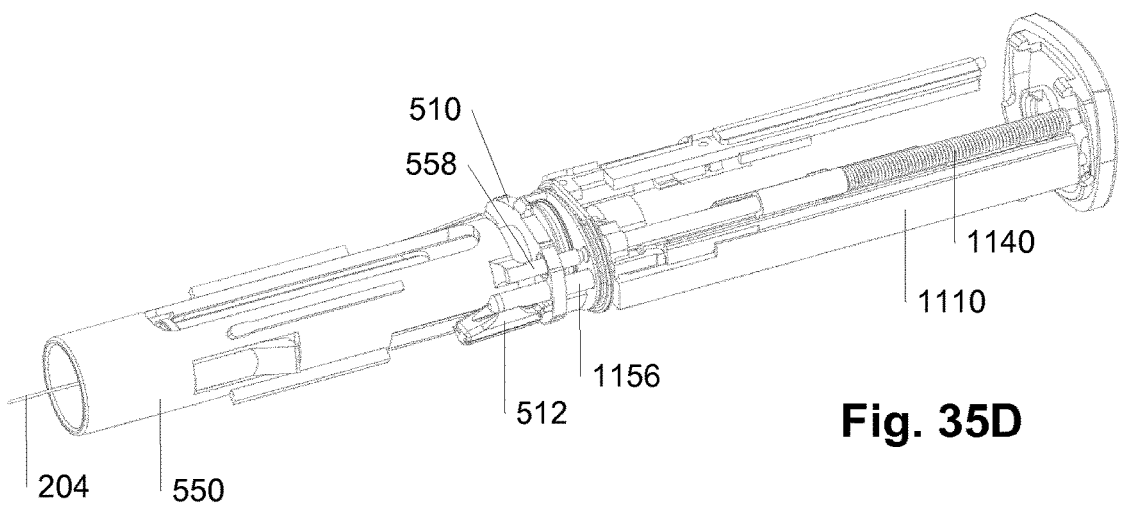
FIGS. 35D-F show the locking of the cassette skin sensor in a proximal position after delivery of medicament.
Figure 35E:
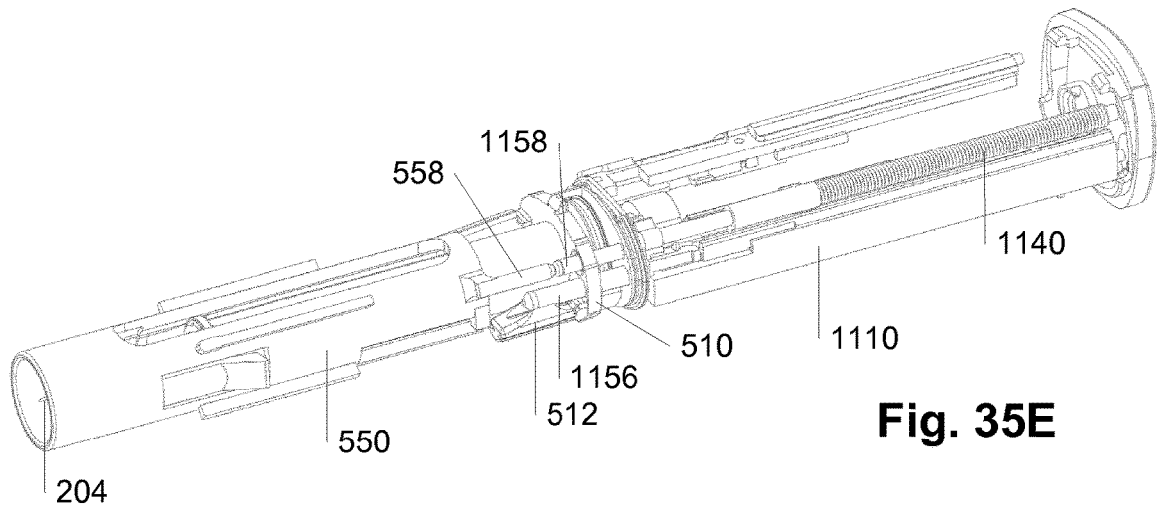
Figure 35F:
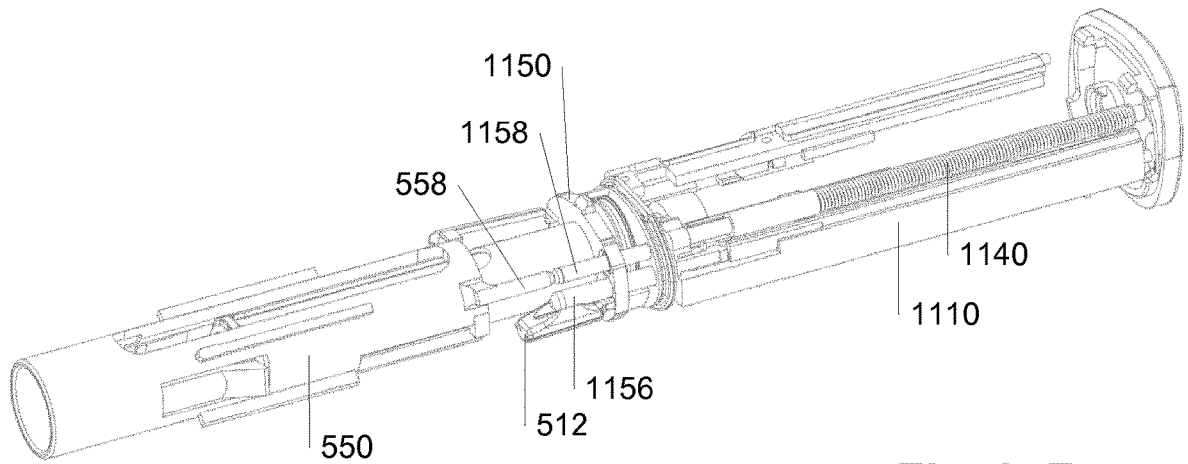
Figure 35G:
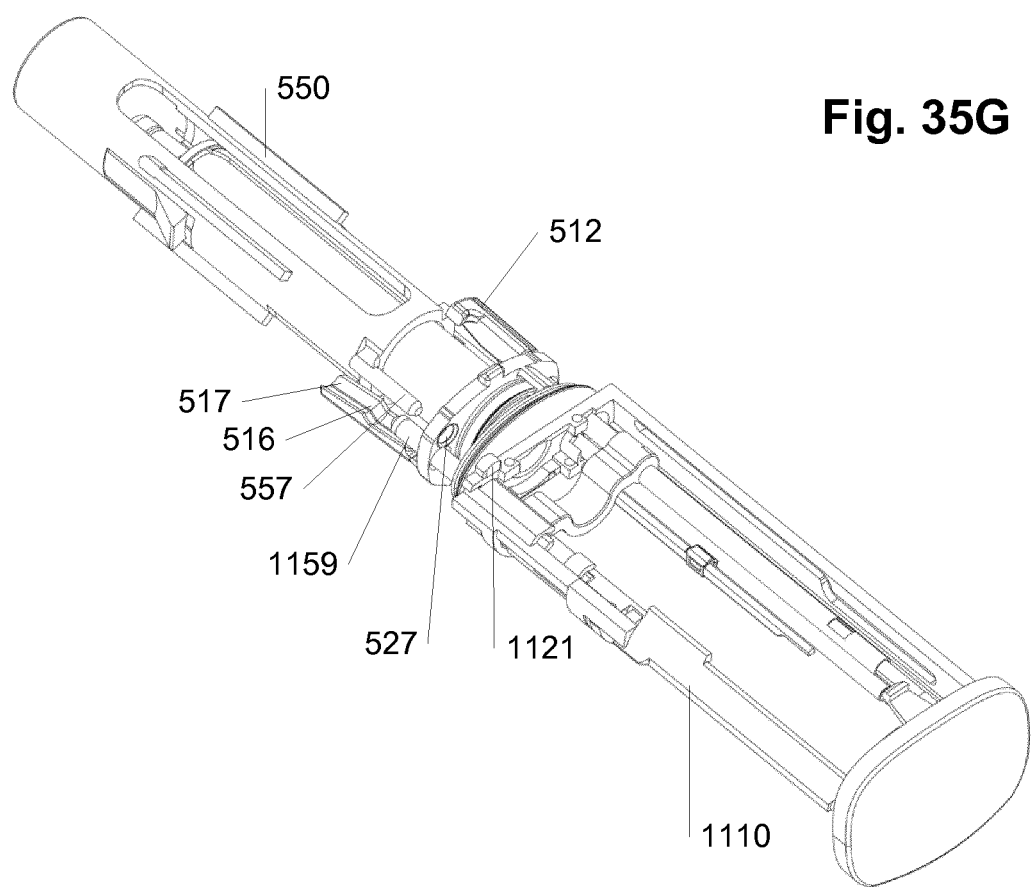
FIG. 35G shows the cassette skin sensor seen from a different angle compared to FIGS. 35A-F.

The syringe holder 510 also has a second syringe holder arm 516 extending in a proximal direction from the ring-shaped syringe holder part 519 (see FIG. 35G). The second syringe holder arm 516 comprises a distal surface 518 at the proximal end of the arm. The distal surface 518 is resting against a second locking protrusion 554 on the cassette skin sensor 550. This engagement prevents movement of the cassette skin sensor 550 away from the syringe holder 510. Before unlocking the cassette skin sensor 550 and the syringe holder 510 by deflection of the first syringe holder arm 512, the two parts are thus prevented from both moving towards and away from each other.

The second syringe holder arm 516 is also flexibly connected to the ring-shaped syringe holder part 519. When a second skin sensor release pin 1159 of the auto injector 100ƒ is pushed through the fourth pin opening 529, it comes in contact with the second syringe holder arm 516 (see FIG. 35G). This results in a deflection of the second syringe holder arm 516, which in turn releases the cassette skin sensor 550 again, this time allowing it to move away from the syringe holder 510 in the proximal direction.

The third pin opening 528 allows passage of a skin sensor forward pin 1158 of the auto injector 100ƒ (see FIGS. 35A-F), which pushes on the second cassette skin sensor pin 558 of the cassette skin sensor 550. The second cassette skin sensor pin 558 may also pass through the third pin opening 528 before coming in contact with the skin sensor forward pin 1158.

The syringe holder 510 has two syringe holder locking protrusions 524 fitting into openings 544 at the distal end 542 of the cassette housing 540. This locks the syringe holder 510 and the cassette housing 540 together. More locking protrusions/openings could also be imagined.

The syringe holder 510 further comprises one or more cassette locking protrusions 539 locking the syringe 200 to the cassette 500.

The cassette 500 further has a rigid needle shield holder 530 having a first part 531 positioned between the rigid needle shield 206 and the proximal end of the syringe compartment 202. The rigid needle shield holder 530 comprises an inner rigid needle shield tube 535 with the first part 531 and an outer an outer rigid needle shield tube 536. This is most clearly seen in FIGS. 34A-C. The outer rigid needle shield tube 536 surrounds the inner rigid needle shield tube 535, and the inner rigid needle shield tube 535 surrounds the rigid needle shield 206.

Figure 30:
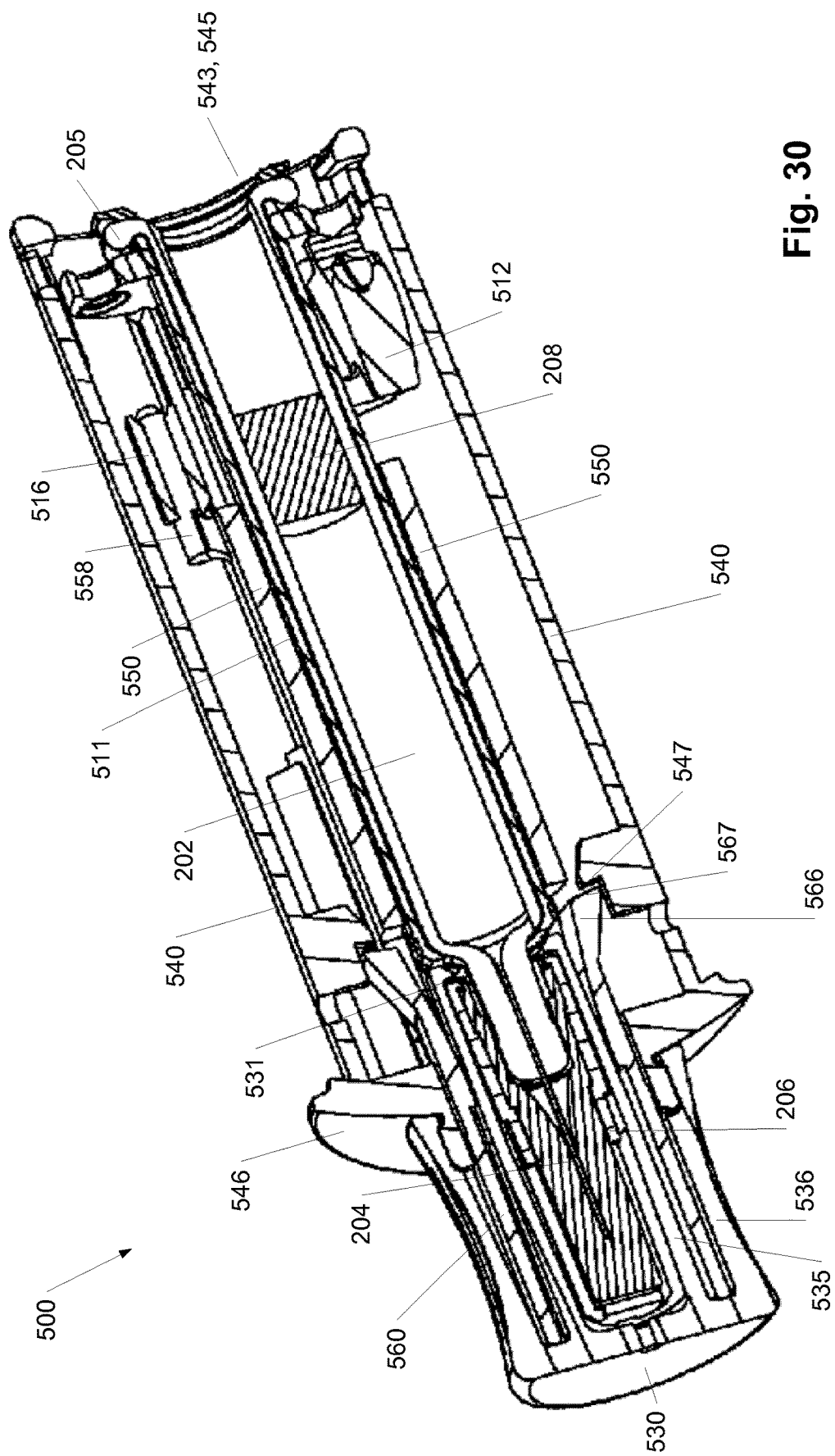
FIG. 30 shows a cut-through of the cassette of FIG. 29A.

The outer rigid needle shield tube 536 abuts the housing shoulder 546 of the cassette housing 540 as shown in FIG. 30. The proximal end 560 of the cassette skin sensor 550 is positioned between the inner rigid needle shield tube 535 and the outer rigid needle shield tube 536 as shown in FIG. 30. The rigid needle shield holder 530 is removable from the syringe compartment 202, and wherein when the rigid needle shield holder 530 is removed, the rigid needle shield 206 follows with it, whereby the hollow needle 204 is exposed. The rigid needle shield holder 530 therefore functions as both a cassette cap and a rigid needle shield holder.

Figure 31:
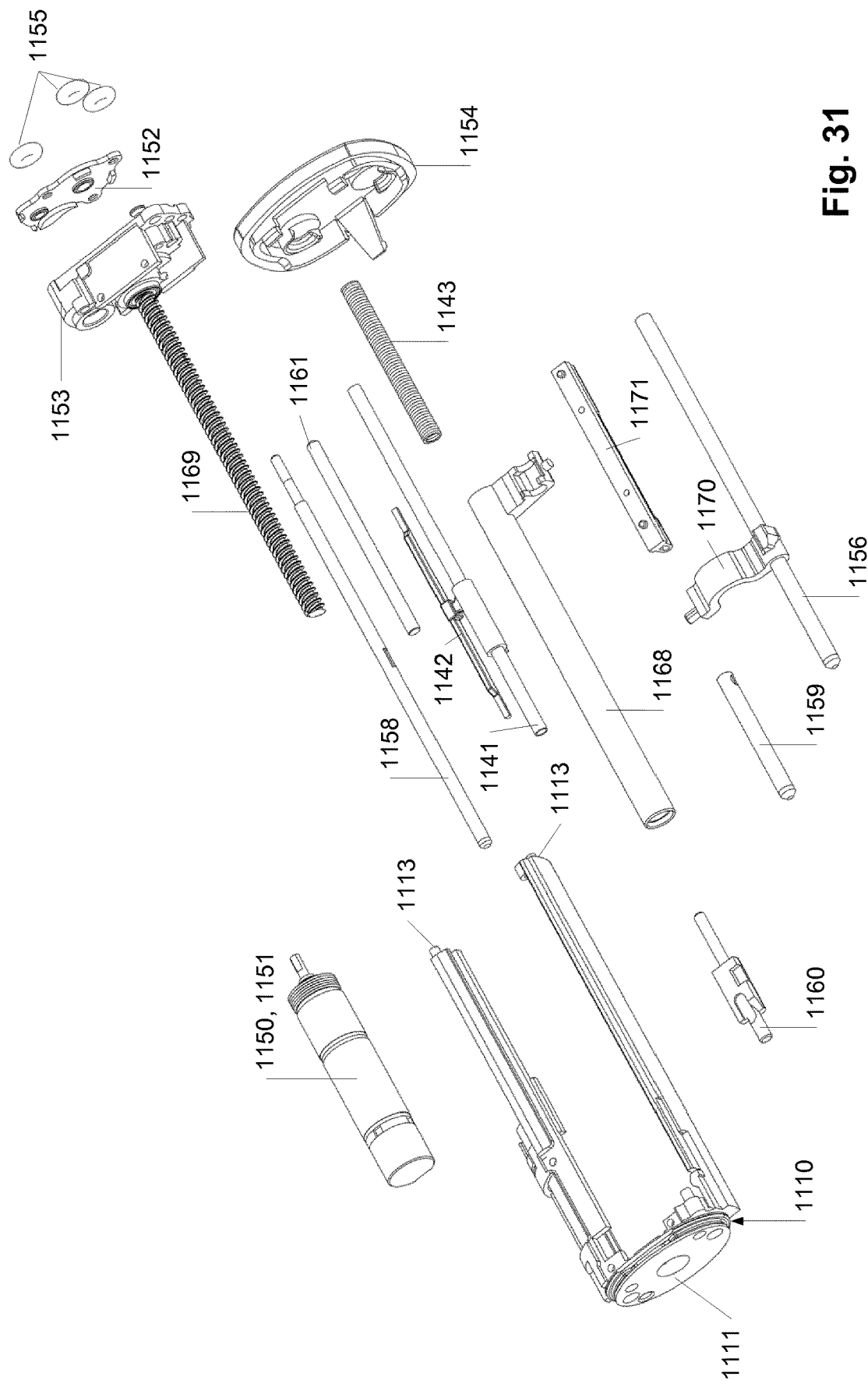
FIG. 31 shows a sixth embodiment of an auto injector for receiving the cassette of FIGS. 29-30, where the auto injector is shown in an exploded view.
Figure 32A:
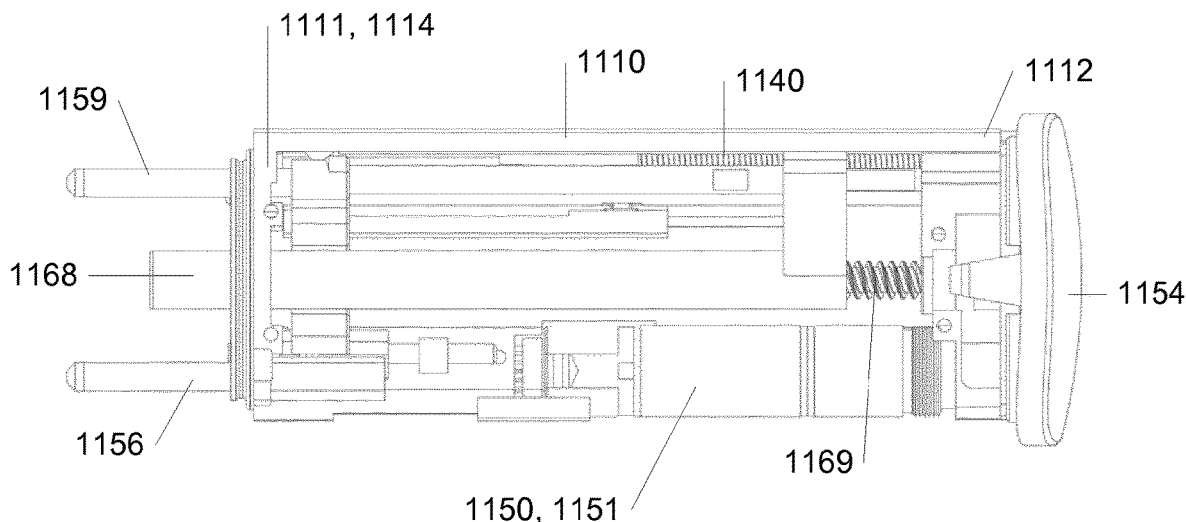
FIG. 32A shows a cut-through view and FIG. 32B a side-view of the of the auto injector of FIG. 31.
Figure 32B:
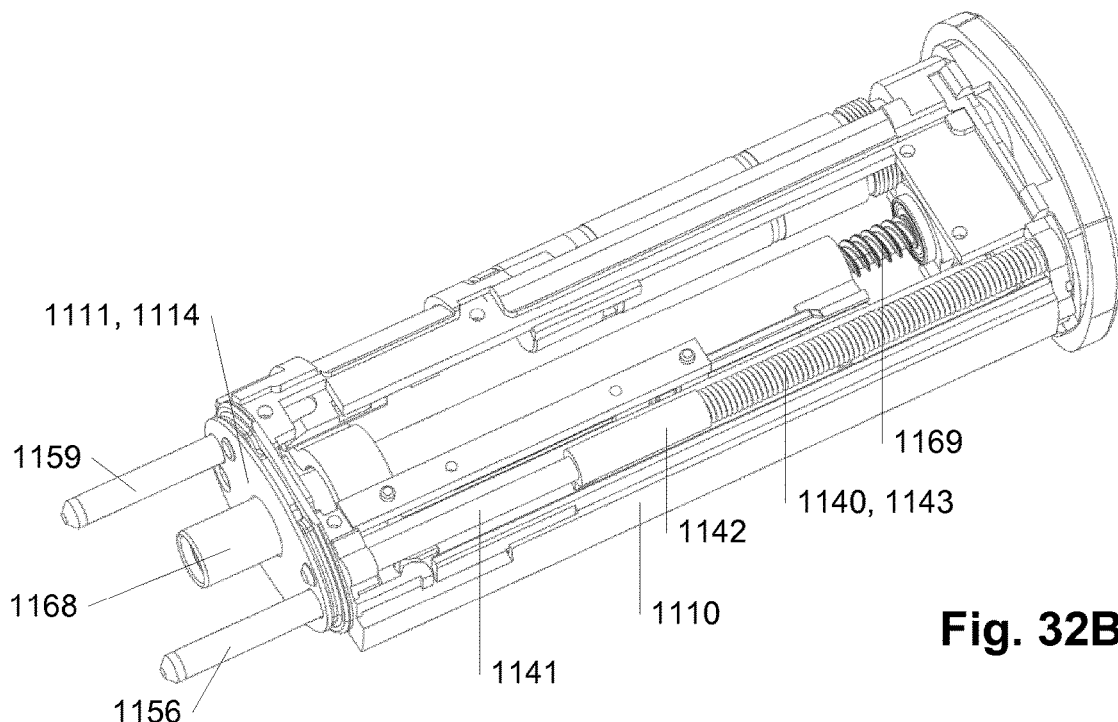

FIGS. 31-32 show a sixth embodiment of an auto injector for receiving the cassette of FIGS. 29-30. The auto injector 100ƒ is shown in an exploded view in FIG. 31, whereas FIGS. 32A-B show the assembled auto injector 100ƒ. For obtaining a clear view inside the auto injector, the outer housing 1102 has been omitted. The outer housing 1102 can be seen in FIGS. 34A-D.

The auto injector 100ƒ extends from a proximal end to a distal end and comprises the outer housing 1102 extending from a proximal end to a distal end. The housing is in one piece in this embodiment of the auto injector. The cassette 500 is loaded into the auto injector in a front-loading configuration.

The auto injector comprises a cassette receiver 1110 configured to receive the cassette 500. The cassette 500 is interfacing with the auto injector 100ƒ at the distal end of the cassette 500, whereby the two part are sharing the same longitudinal axis. This mitigates the risk of the cassette getting stuck inside in the auto injector. Further, it makes the connection as slim as possible. The only auto injector element, which extends in parallel with the cassette 500 is normally the outer housing 1102. Inside the auto injector 100ƒ, is a drive module 1150, which is adapted to move a piston 1168. The piston 1168 is moved proximally pushing on the stopper 208 inside the syringe whereby medicament can be expelled from the syringe. The piston 1168 has an inner threading (not shown in the figures), which engages with an outer threading on a led screw 1169. When the lead screw 1169 is rotated by the drive module 1150, the piston 1168 moves proximally. The drive module 1150 includes a motor 1151, which through a gear assembly 1153, rotates the lead screw 1169. The gear assembly 1153 is covered by a gear cover 1152, some O-rings 1155 and a chassis cover 1154.

The drive module 1150 also controls the movement of a number of pins comprised in the auto injector 100ƒ. As shown in FIG. 31, the number of pins include; a first skin sensor release pin 1156, a skin sensor forward pin 1158, a second skin sensor release pin 1159, and a cassette detection pin 1160. Thus, the drive module 1150 is further configured for moving the first skin sensor release pin 1156, the skin sensor forward pin 1158, the second skin sensor release pin 1159, and the cassette detection pin 1160 proximally.

Acting on the skin sensor forward pin 1158, which pushes the cassette skin sensor 550 proximally after delivery of medicament, is a spring system 1140. The spring system 1140 includes a spring guidance pin 1141 around which a supporting chassis 1142 connected to the skin sensor forward pin 1158 is found. Extending around the guidance pin 1141 is also a spring 1143. When the spring 1143 is allowed to relax, it pushes the supporting chassis 1142 forward, which in turn pushes the skin sensor forward pin 1158 proximally. Inside the skin sensor forward pin 1158 at the distal end thereof is a guide pin 1161 for the skin sensor forward pin 1158. When the skin sensor spring system 1140 pushes the cassette skin sensor 550 proximally after delivery of medicament, it is pushed into a locked position preventing distal movement of the cassette skin sensor 550.

Figure 33:
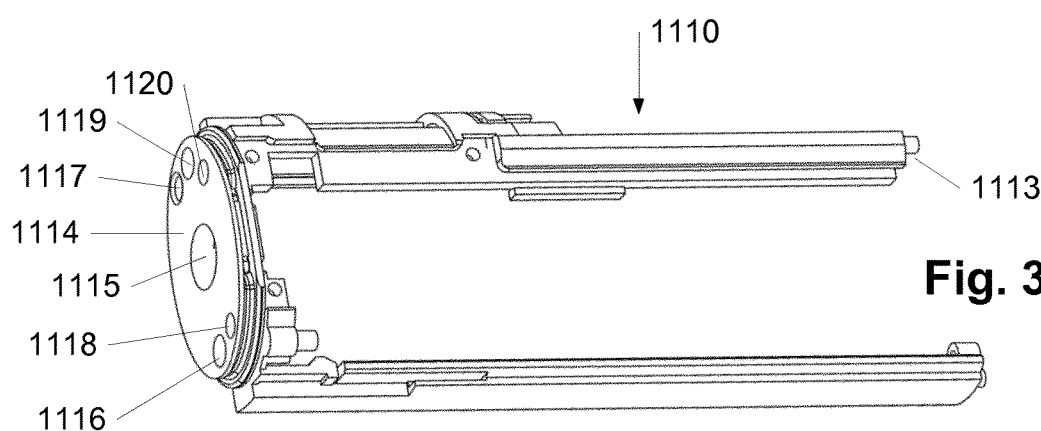
FIG. 33 shows a close-up of the chassis shown in FIG. 31.

The auto injector 100ƒ also comprises a cassette receiver 1110 configured to receive a cassette. The cassette receiver is in the shape of a chassis as seen in FIGS. 31 and 33, the latter showing an enlarged view of the cassette receiving chassis 1110. The cassette receiving chassis 1110 is extending from a proximal end 1111 to a distal end 1112. At the proximal end 1111 of the chassis 1110, is a ring-shaped chassis part 1114 with a number of openings including a piston opening 1115, a first pin opening 1116, a second pin opening 1117, a third pin opening 1118, a fourth pin opening 1119, and a fifth opening 1120.

When the cassette 500 is positioned in the auto injector 100f, the piston opening 1115 is aligned with piston opening 525 in the syringe holder 510 to allow the auto injector piston 1168 to extend there through. Likewise, the first pin opening 526 in the syringe holder 510 is aligned with the first pin opening 1116 such that the first skin sensor release pin 1156 can pass through both openings to deflect the first syringe holder arm 512 thereby unlocking the cassette skin sensor 550 from the syringe holder 510.

The second pin opening 1117 in the a ring-shaped chassis part 1114 is aligned with the second pin opening 527 in the syringe holder 510 for allowing passage of the first cassette skin sensor pin 557 of the cassette skin sensor 550 to pass there through. The second pin opening 1117 does not extend all the way through, but instead has an end surface 1121 (see FIG. 35G), which stops the first cassette skin sensor pin 557 of the cassette skin sensor 550 in its distal movement towards the auto injector. Thus, the second pin opening 1117 is a well-shaped opening with an end surface 1121 limiting the distal movement of the first cassette sensor pin 557 and thereby the cassette skin sensor 550 inside the auto injector 100f.

The third pin opening 1118 is aligned with the third pin opening 528 in the syringe holder 510 for allowing passage of the skin sensor forward pin 1158, and/or the second cassette skin sensor pin 558 there through. This is shown in details in FIGS. 35A-F. The fourth pin opening 1119 is aligned with the fourth pin opening 529 in the syringe holder 510 for allowing passage of the second skin sensor release pin 1159 there through.

The fifth opening 1120 does not have a corresponding opening in the syringe holder. Instead, through the fifth opening 1120, a cassette detection pin 1160 extends. The cassette detection pin 1160 detects when a cassette 500 is connected to the auto injector 100f. The release of the cassette skin sensor 550 will not occur if there is no detection of a cassette by the cassette detection pin 1160.

The cassette receiver 1110, the piston 1168, and the drive module 1150 are comprised inside the outer housing 1102 of the auto injector 100f, and the cassette 500 is removable received in the auto injector 100f.

FIGS. 34A-C show cut-through views of the auto injector 100f with the cassette 500 during the loading and locking of the cassette 500 in the auto injector 100f. In FIG. 34A, the cassette 500 has been received inside the auto injector housing 1102. As seen in FIGS. 34A-C, the outer housing 1102 has a protruding tab 1105 on its inside. When the cassette 500 is positioned in the auto injector 100f, the cassette locking protrusion 539 is positioned near the protruding tab 1105. The auto injector then moves the skin sensor release pins 1156, 1159 forward along with the piston 1168 as seen when comparing FIGS. 34A and 34B.

The cassette locking protrusion 539 are now prevented from bypass the protruding tab 1105, thereby locking the cassette 500 to the auto injector 100f. As the cassette 500 is now firmly locked inside the auto injector 100f, the rigid needle shield holder 530 can now be manually removed from the cassette 500. This also removes the rigid needle shield 206 exposing the needle 204.

By further proximal movement of at least the first skin sensor release pin 1156, the cassette skin sensor 550 is released from the syringe holder 510. This process is shown in FIGS. 35A-C illustrating the steps in releasing the cassette skin sensor 550 from the syringe holder 510 by means of moving the first skin sensor release pin 1156 proximally. As seen in FIGS. 35B, the first locking protrusion 553 and the proximal surface 514 of the arm 512 no longer engage. The auto injector is now ready for insertion of the needle 204 into a patient. This is done by pressing the cassette 500 towards the skin of the patient thereby pushing the cassette skin sensor 550 distally as shown in FIGS. 35C and 35D. Thus, when the drive module 1150 moves the first skin sensor release pin 1156 proximally, the cassette skin sensor 550 is distally unlocked from the syringe holder 510 allowing for distal movement of the cassette skin sensor 550, wherein the unlocking of the cassette skin sensor 550 locks the cassette 500 in the auto injector 100f.

When the drive module 1150 moves the piston 1168 proximally for delivery of medicament, the second skin sensor release pin 1159 is also unlocked for movement of the cassette skin sensor 550 proximally after delivery of medicament and/or removal of the auto injector 100f from the patient's skin.

FIGS. 35D-E show the locking of the cassette skin sensor 550 in a proximal position after delivery of medicament. FIG. 35D illustrates delivery position. In this position, the skin sensor forward pin 1158 exerts a pressure on the second cassette skin sensor pin 558 by the spring system 1140. In FIG. 35E, the auto injector has been lifted from the skin of the patient. By doing so, the spring system 1140 pushes the cassette skin sensor 550 forward in the proximal direction. As the cassette skin sensor 550 has been unlocked for movement in the proximal direction by second skin sensor release pin 1159, the cassette skin sensor 550 can be locked in a forward position where contact with the needle is prevented by e.g. a protrusion inside the cassette housing engaging with the cassette skin sensor protrusion.

After delivery of medicament, the drive module retracts the piston and the skin sensor release pins 1156, 1157, which unlocks the cassette from the auto injector allowing the user to remove the cassette. The rigid needle shield and the rigid needle shield holder cannot be connected to the cassette after use, which ensures that the user will not mistake a used cassette for a non-used.

The cassette 500 and auto injector 100f is shown and described in a configuration using manual insertion of the needle. An automatic needle insertion could also be envisioned by included a spring-motor system as described in connection with e.g. FIG. 9.

Figure 36:
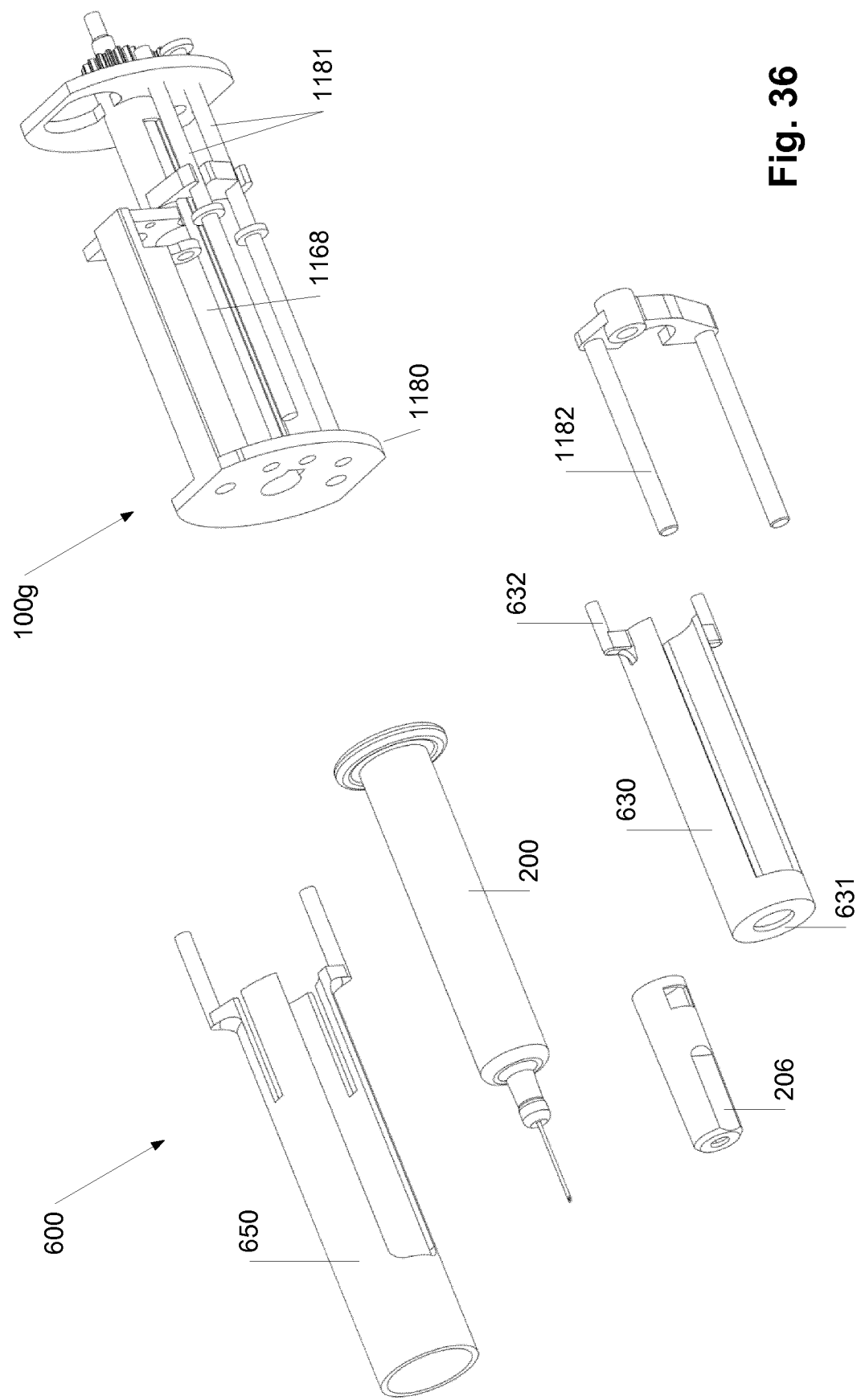
FIG. 36 show a seventh embodiment of the auto injector with cassette in an exploded view.
Figure 37A:
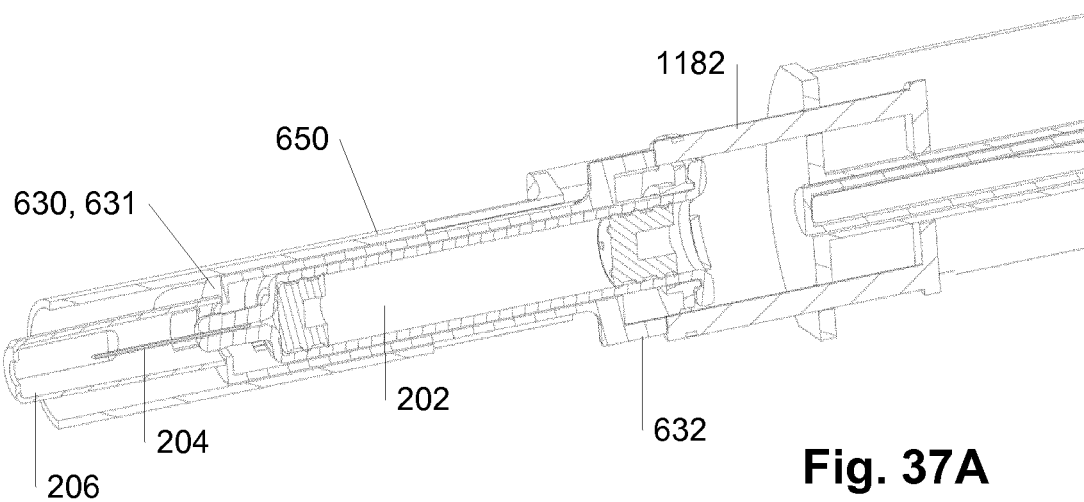
FIGS. 37A-C show the release of the rigid needle shield in the auto injector cassette of FIG. 36.
Figure 37B:
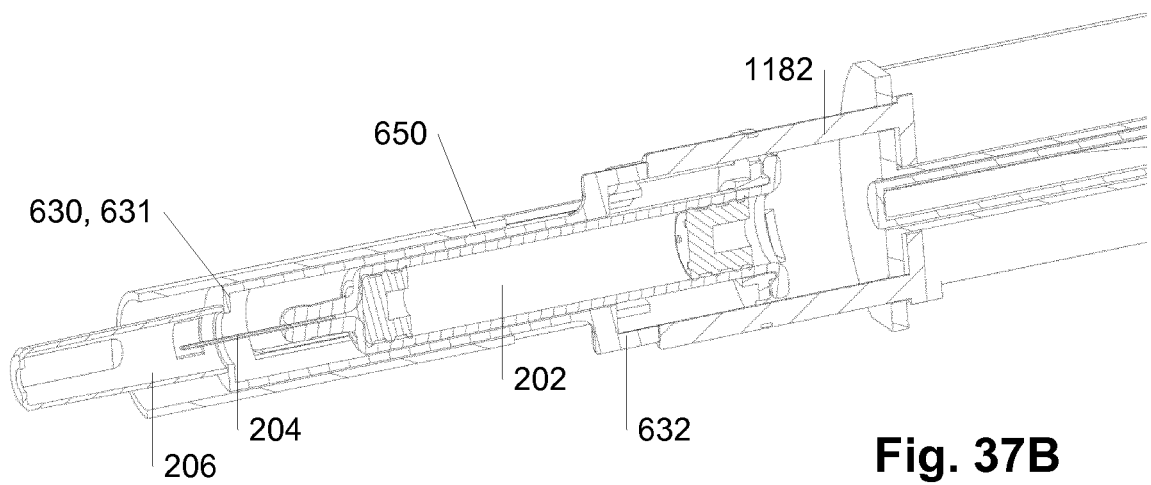
Figure 37C:
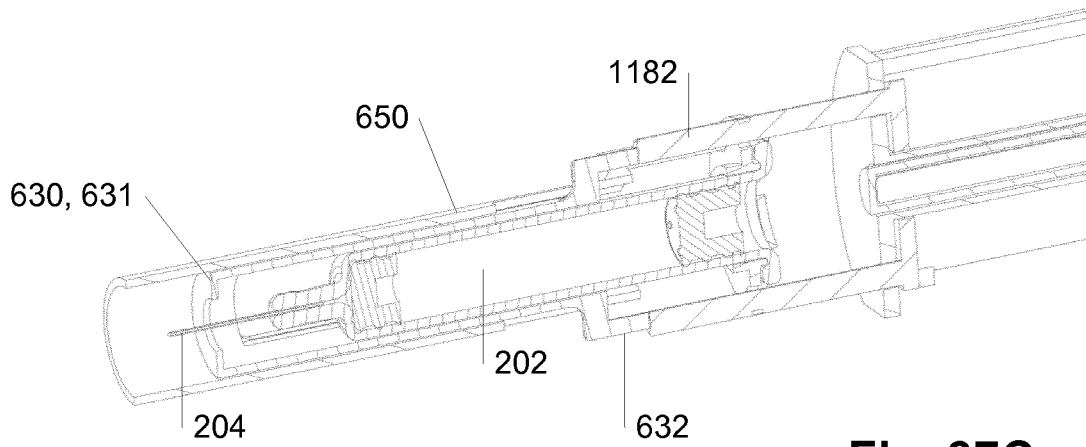

FIG. 36 show selected parts of a seventh embodiment of the auto injector 100g with a cassette 600 in an exploded view. The auto injector 100g comprises a cassette receiving chassis 1180 shown with a number of release pins 1181 and a piston 1168, and a rigid needle shield release pin system 1182. The cassette 600 comprises a rigid needle shield holder 630 with a first part 631 positioned between the rigid needle shield 206 and the proximal end of the syringe 200. The rigid needle shield holder 630 is an elongated tube positioned between the syringe 200 and a cassette skin sensor 650, and is longitudinal movable relative to the cassette skin sensor 650. The rigid needle shield holder 630 comprises two rigid needle shield holder pins 632 extending from a distal end of the rigid needle shield holder 630. The rigid needle shield release pin system 1182 are abutting the two holder pins 632. When the rigid needle shield release pin system 1182 is moved forward in the proximal direction, the rigid needle shield holder 630 is pushed proximally for release of the rigid needle shield 206. This release sequence is shown in FIGS. 37A-C, where FIG. 37A shows the system prior to movement of the needle shield release pin system 1182, FIG. 37B shows the system after proximal movement of the needle shield release pin system 1182, and FIG. 37C shows the system after the user has removed the rigid needle shield 206.

The auto injector may further be described by the following items:

1. An auto injector (100a, 100b, 100c, 100d) for delivery of a medicament, the auto injector extending from a proximal end to a distal end, the auto injector comprising:
   a housing (102);
   a syringe holder (110) configured to receive a syringe (200) comprising:
     a syringe compartment (202) extending from a proximal end (201) to a distal end (203), the syringe compartment containing the medicament;
     a hollow needle (204) in fluid connection with the proximal end (201) of the syringe compartment;
     a rigid needle shield (206) connected to the proximal end (201) of the syringe compartment and covering the hollow needle;
     a stopper (208) movable from a distal position to a proximal position inside the syringe compartment by means of a plunger rod (210) moving the stopper proximally;
   a first drive module (120) adapted to move the syringe holder (110) relatively to the housing (102);
   a rigid needle shield remover (130) comprising a first part (132) adapted for being positioned between the rigid needle shield (206) and the proximal end (201) of the syringe compartment, wherein when the first part is positioned between the rigid needle shield and the proximal end of the syringe compartment, the rigid needle shield can be separated from the proximal end of the syringe compartment upon relative movement between the syringe holder and the rigid needle shield remover,
   wherein the syringe holder, the first drive module, and the a rigid needle shield remover are comprised inside the housing of the auto injector, and wherein the rigid needle shield remover (130) comprises at least two arms (133) extending from a distal end (134) to a proximal end, the at least two arms each pivotally attached to the auto injector or the rigid needle shield remover holder.
2. The auto injector according to item 1, wherein the syringe further comprises the plunger rod connected to a distal end of the syringe compartment.
3. The auto injector according to item 1, wherein the auto injector comprises a piston acting as the plunger rod, the piston being positioned inside the housing possibly extending outside the housing at a distal end of the plunger rod.
4. The auto injector according to item 1, wherein the syringe further comprises the plunger rod connected to a distal end of the syringe compartment, and wherein the auto injector comprises a piston moving the plunger rod distally for delivery of medicament.
5. The auto injector according to any preceding item further comprising a first spring (140) adapted for moving the syringe holder proximally for insertion of the needle.
6. The auto injector according to item 5 further comprising an activation button (142) adapted for releasing the first spring such that the syringe holder containing the syringe is moved proximally for insertion of the needle.
7. The auto injector according to item 6, wherein the activation button (142) is positioned outside the housing.
8. The auto injector according to item 6, wherein the activation button (142) is positioned inside the housing.
9. The auto injector according to any preceding item further comprising a second drive module adapted for moving the plunger rod distally for the delivery of the medicament.
10. The auto injector according to any of the items 1-8, wherein the first drive module is further adapted for moving the plunger rod distally for the delivery of the medicament.
11. The auto injector according to any preceding item, wherein the first drive module is configured for moving the syringe holder distally from a primary position (L1) to a secondary position (L2), wherein in the secondary position the first part of the rigid needle shield remover is positioned between the rigid needle shield and the proximal end of the syringe compartment.
12. The auto injector according to item 11, wherein the first drive module is configured for moving the syringe holder further distally from the secondary position (L2) to a tertiary position (L3), wherein in the tertiary position (L3) the rigid needle shield is loosened from the syringe compartment.
13. The auto injector according to item 12, wherein during the movement of the syringe holder from the secondary position (L2) to the tertiary position (L3), the rigid needle shield remover is not moving.
14. The auto injector according to item 12 or 13, wherein the rigid needle shield remover supports the rigid needle shield in the tertiary position (L3) thereby preventing it from being separated from the syringe before the user manually removes it.
15. The auto injector according to any of the items 12-14, wherein the rigid needle shield in the tertiary position (L3) is sticking 5-15 mm out of the housing for easy manually removal by the user.
16. The auto injector according to any preceding item, wherein the auto injector further comprises a rigid needle shield sensor (146) adapted for detecting if the rigid needle shield is attached to the syringe.
17. The auto injector according to item 16, wherein the rigid needle shield sensor is connected to the rigid needle shield remover, the syringe holder, or the syringe.
18. The auto injector according to item 17, wherein a distal end (147) of the rigid needle shield sensor is connected to the syringe holder and a proximal end (148) of the rigid needle shield sensor is in contact with the rigid needle shield when the rigid needle shield is connected to the syringe.
19. The auto injector according to any of the items 16-18, wherein the rigid needle shield sensor comprises a spring loaded rotatable arm and an electronic switch, wherein the rotatable arm is in a depressed position when the rigid needle shield is connected to the syringe, and wherein the rotatable arm is in the depressed position interacts with the electronic switch thereby allowing electronics to detect the presence of the rigid needle shield.
20. The auto injector according to any of the items 16-19, wherein the auto injector further comprises one or more additional rigid needle shield sensors adapted for detecting if the rigid needle shield is attached to the syringe at one or more different locations along the length of the rigid needle shield compared to the first mentioned rigid needle shield sensor.
21. The auto injector according to any of the items 12-20, wherein the first spring is adapted for moving the syringe holder proximally from the tertiary position (L3) to a quaternary position (L4) for insertion of the needle.
22. The auto injector according to any of the items 21, wherein the first drive module or the second drive module is moving the plunger rod distally for the delivery of the medicament when the syringe holder is in the quaternary position (L4).
23. The auto injector according to any of the items 22, wherein the first drive module is further configured for moving the syringe holder distally from the quaternary position (L4) to a quinary position (L5) after delivery of the medicament, wherein the syringe is removable from the auto injector in the quinary position (L5).
24. The auto injector according to any of the items 23, wherein the quinary position (L5) and the first position (L1) are the same.
25. The auto injector according to any of the items 24, wherein the quinary position (L5) and the tertiary position (L3) are the same.
26. The auto injector according to any preceding item, wherein the auto injector further comprises a syringe sensor (144) adapted for detecting when a syringe is positioned in the syringe holder.
27. The auto injector according to item 26, wherein the syringe sensor is positioned inside the housing of the auto injector.
28. The auto injector according to any of the preceding items further comprising a rigid needle shield remover holder positioned inside the housing, wherein the distal end of the needle shield remover is pivotally attached to the rigid needle shield remover holder.
29. The auto injector according to item 28, wherein the rigid needle shield remover holder is movable in a longitudinal direction relatively to the housing of the auto injector.
30. The auto injector according to item 28, wherein the rigid needle shield remover holder is an integrated part of the housing of the auto injector.
31. The auto injector according to any preceding item, wherein the distal ends of the at least two arms (133) of the needle shield remover are pivotally attached to the auto injector or the rigid needle shield remover holder.
32. The auto injector according to any of the items 1-30, wherein a middle position between the distal ends and the proximal ends of each of the at least two arms of the needle shield remover is pivotally attached to the auto injector or the rigid needle shield remover holder.
33. The auto injector according to any preceding item, wherein the rigid needle shield remover comprises a second part (138) adapted for supporting the rigid needle shield when it has been separated from the syringe compartment.
34. The auto injector according to any preceding item, wherein the auto injector further comprises one or more arms springs and wherein the rigid needle shield remover comprises at least two arms, wherein the one or more arms springs pushes the at least two arms centrally at the proximal end of the at least two arms.
35. The auto injector according to item 34, wherein the rigid needle shield sensor is adapted for detecting the angular rotation of the at least two arms towards each other.
36. The auto injector according to item 34 or 35, wherein the one or more arms are substantially linear.
37. The auto injector according to item 34 or 35, wherein the one or more arms are L-shaped.
38. The auto injector according to any preceding item further comprising a skin sensor (150) at the proximal end of the auto injector, the skin sensor being longitudinally displaceable relatively to the housing.
39. The auto injector according to item 38, wherein the skin sensor covers the insertion needle after insertion.
40. The auto injector according to any preceding item, wherein the first drive module is an electrical motor.
41. The auto injector according to item 40, wherein the electrical motor of the first drive module is the only motor in the auto injector.
42. The auto injector according to any of the items 9-40, wherein the second drive module is an electrical motor.
43. The auto injector according to any preceding item further comprising a syringe comprising:
 a syringe compartment extending from a proximal to a distal end, the syringe compartment containing the medicament;
 a hollow needle in fluid connection with the proximal end of the syringe compartment;
 a rigid needle shield connected to the proximal end of the syringe compartment and covering the hollow needle;
 a stopper movable from a distal position to a proximal position inside the syringe compartment.

The cassette and auto injector may further be described by the following clause:
1. A cassette (400, 500) for use in an auto injector for administering a medicament, the auto injector (100e, 100f, 100g) extending from a proximal end to a distal end and comprising:
 a housing (102, 1102) extending from a proximal end (103, 1103) to a distal end (104, 1104);
 a piston (168, 1168);
 a cassette receiver (172, 1110) configured to receive the cassette (400, 500);
 a drive module (120, 1150) adapted to move the piston (168, 1168);
 wherein the cassette receiver (172, 1110), the piston (168, 1168), and the drive module (120, 1150) are comprised inside the housing (102, 1102) of the auto injector (100e, 1000, and
 wherein the cassette (400, 500) comprises:
 a syringe compartment (202) containing the medicament and extending from a proximal end to a distal end;
 a hollow needle (204) in fluid connection with the proximal end of the syringe compartment;
 a rigid needle shield (206) connected to the proximal end of the syringe compartment and covering the hollow needle;
 a stopper (208) movable from a distal position to a proximal position inside the syringe compartment by means of the piston moving the stopper proximally for emptying the syringe compartment;
 a syringe holder (410, 510) extending around at least part of the syringe compartment;
 a rigid needle shield holder (430, 530, 630) having a first part (431, 531, 631) positioned between the rigid needle shield and the proximal end of the syringe compartment, and
 a cassette skin sensor (450, 550, 560), wherein the cassette (400, 500) is removable received in the auto injector (100e, 100f).

2. The cassette according to any preceding clause, wherein the syringe compartment (202), the hollow needle (204) and the stopper (208) is part of a syringe (200), wherein the syringe (200) is fixed inside the syringe holder (410, 510) at a distal end (205) of the syringe (200).

3. The cassette according to any preceding clause, wherein the cassette (400, 500) is interfacing with the auto injector (100e, 100f at the distal end of the cassette (400, 500) sharing the same longitudinal axis.

4. The cassette according to any preceding clause, wherein the syringe holder (510) comprises a syringe holder support tube (511), which supports the syringe compartment (202).

5. The cassette according to any preceding clause, wherein the cassette skin sensor (450, 550) covers at least part of the syringe holder (410, 510), such as the majority of the syringe holder.

6. The cassette according to any preceding clause, wherein the cassette skin sensor (550) comprises at least a first skin sensor pin (557) and/or a second skin sensor pin (558) extending from the distal end (552) of the cassette skin sensor (550).

7. The cassette according to any preceding clause, wherein the syringe holder (510) comprises one or more openings selected from the group of:
   a first pin opening (526) for allowing passage of a first skin sensor release pin (1156) of the auto injector (100f) there through;
   a second pin opening (527) for allowing passage of the first cassette skin sensor pin (557);
   a third pin opening (528) for allowing passage of a skin sensor forward pin (1158) of the auto injector (100f, and/or the second cassette skin sensor pin (558) there through;
   a fourth pin opening (529) for allowing passage of a second skin sensor release pin (1159) of the auto injector (1000 there through;
   a piston opening (525) for allowing passage of the auto injector piston (1168) there through.

8. The cassette according to clause 7, wherein the syringe holder (510) comprises a ring-shaped syringe holder part (519), wherein the piston opening (525) and/or one or more of the pin openings (526, 527, 528, 529) are positioned in the ring-shaped syringe holder part (519).

9. The cassette according to clause 8, wherein the syringe holder (510) comprises a first syringe holder arm (512) extending in a proximal direction from the ring-shaped syringe holder part (519).

10. The cassette according to clause 9, wherein the first syringe holder arm (512) comprises a proximal surface (514), and wherein the cassette skin sensor (550) comprises a first locking protrusion (553) engaging with the proximal surface (514), wherein the engagement of the first locking protrusion (553) and the proximal surface (514) prevents movement of the cassette skin sensor (550) towards the syringe holder (510).

11. The cassette according to any of the clauses 9-10, wherein the first syringe holder arm (512) is flexibly connected to the ring-shaped syringe holder part (519).

12. The cassette according to any of the clauses 9-11, wherein the first syringe holder arm (512) is deflectable by proximal movement of the first skin sensor release pin (1156) of the auto injector (1000 through the first pin opening (526) in the syringe holder (510), wherein the deflection of the first syringe holder arm (512) releases the cassette skin sensor (550) allowing it to move towards the syringe holder (510).

13. The cassette according to clause 12, wherein upon movement of the cassette skin sensor (550) towards the syringe holder (510):
   the first cassette skin sensor pin (557) is brought into/extends through the second pin opening (527) in the syringe holder (510), and
   the second cassette skin sensor pin (558) is brought into/extends through the third pin opening (528) in the syringe holder (510).

14. The cassette according to any of the clauses 8-13, wherein the syringe holder (510) comprises a second syringe holder arm (516) extending in a proximal direction from the ring-shaped syringe holder part (519).

15. The cassette according to clause 14, wherein the second syringe holder arm (516) comprises a distal surface (518), and wherein the cassette skin sensor (550) comprises a second locking protrusion (554) against which the distal surface (518) is resting, wherein the engagement of the second locking protrusion (554) and the distal surface (518) prevents movement of the cassette skin sensor (550) away from the syringe holder (510).

16. The cassette according to any of the clauses 14-15, wherein the second syringe holder arm (516) is flexibly connected to the ring-shaped syringe holder part (519).

17. The cassette according to any of the clauses 14-16, wherein the second syringe holder arm (516) is deflectable by proximal movement of the second skin sensor release pin (1159) of the auto injector (1000 through the fourth pin opening (529) in the syringe holder (510), wherein the deflection of the second syringe holder arm (516) allows the cassette skin sensor (550) it to move away from the syringe holder (510).

18. The cassette according to any preceding clause, wherein the syringe holder (510) further comprises one or more cassette locking protrusions (539) locking the syringe holder (510) and thereby the cassette (500) to the auto injector housing (1102) when the cassette (500) is positioned in the auto injector (100).

19. The cassette according to any preceding clause, wherein the syringe holder (510) and the skin sensor (550) are longitudinally movable relative to each other upon release of the skin sensor (550) from the syringe holder (510).

20. The cassette according to any preceding clause, wherein the cassette (550) further comprises a cassette housing (540) extending from a proximal (541) to a distal end (542), the cassette housing (540) enclosing at least the syringe holder (510) and the cassette skin sensor (550).

21. The cassette according to clause 20, wherein the cassette housing (540) comprises one or more locking openings (544) at the distal end (542) into which the one or more syringe holder locking protrusions (524) on the syringe holder (510) locks syringe holder (510) to the cassette housing (540).

22. The cassette according to any of the clauses 20-21, wherein the cassette housing (540) comprises one or more internal protruding rails (548) inside the cassette housing (540) for guiding the skin sensor (550) inside the cassette housing (540).

23. The cassette according to any of the clauses 20-22, wherein the cassette housing (540) comprises a distal end surface (543) with a skin sensor housing opening (545) through which the cassette skin sensor (550) extends.

24. The cassette according to any of the clauses 20-23, wherein the cassette housing (540) is oval.

25. The cassette according to any preceding clause, wherein the rigid needle shield holder (530) comprises an inner rigid needle shield tube (535) with the first part (531) and an outer an outer rigid needle shield tube (536), wherein:
the outer rigid needle shield tube (536) surrounds the inner rigid needle shield tube (535), and
the inner rigid needle shield tube (535) surrounds the rigid needle shield (206).

26. The cassette according to clause 25, wherein the outer rigid needle shield tube (536) abuts the housing shoulder (546) of the cassette housing (540), and wherein the proximal end (560) of the cassette skin sensor (550) is positioned between the inner rigid needle shield tube (535) and the outer rigid needle shield tube (536).

27. The cassette according to clause 25 or 26, wherein the rigid needle shield holder (530) is removable from the syringe compartment (202), and wherein when the rigid needle shield holder (530) is removed, the rigid needle shield (206) follows with it, whereby the hollow needle (204) is exposed.

28. The cassette according to any of the clauses 1-24, wherein the rigid needle shield holder (630) is an elongated tube positioned between the syringe (200) and the cassette skin sensor (650).

29. The cassette according to clause 28, wherein the rigid needle shield holder (630) comprises at least one holder pin (632) extending from a distal end of the rigid needle shield holder (630).

30. The cassette according to clause 29, wherein upon proximal movement of a rigid needle shield holder pin (1182) in the auto injector abutting the at least one holder pin (632), the rigid needle shield holder (630) is pushed proximally for release of the rigid needle shield (206).

31. The cassette according to clause 1, wherein the rigid needle shield holder is contained partly inside the syringe holder.

32. The cassette according to any of the preceding clauses 1-5 or 31, wherein the cassette skin sensor is extending partly around the syringe holder and the rigid needle shield holder.

33. The cassette according to any of the preceding clauses 1-5 or 31-32, wherein the syringe compartment, the syringe holder and the cassette skin sensor are moveable in the distal direction relative to the rigid needle shield holder and the needle shield.

34. The cassette according to any of the preceding clauses 1-5 or 31-33, wherein the cassette skin sensor in a first position covers the rigid needle shield and in a second position exposes at least a proximal part of the rigid needle shield allowing the rigid needle shield to be removed.

35. The cassette according to any of the preceding clauses 1-5 or 31-34, wherein the drive module of the auto injector is further adapted to move the cassette receiver, wherein the piston and the cassette receiver can be moved together or separately 36. The cassette according to any of the preceding clauses 1-5 or 31-35. wherein the drive module is adapted for moving the cassette skin sensor distally relative to the rigid needle shield thereby exposing the rigid needle shield.

37. The cassette according to any of the preceding clauses 1-5 or 31-36, wherein a distal end of the syringe holder is adapted for locking to the cassette receiver in the auto injector when the cassette is placed inside the auto injector.

38. The cassette according to clause 37, wherein the distal end of the syringe holder is locked to the cassette receiver (172) by a first snap joint (174, 422), wherein the first snap joint:
allows for release of the cassette from the cassette receiver when the piston is in a first position, and
locks the cassette to the cassette receiver when the piston is in a second position.

39. The cassette according to clause 38, wherein the distal end (420) of the syringe holder comprises an inner recess (422), wherein one or more locking arms (174) on the cassette receiver snaps into the inner recess of the syringe holder thereby forming the first snap fit joint.

40. The cassette according to any of the preceding clauses 1-5 or 31-39, wherein the rigid needle shield holder is attached to the syringe holder by a second snap joint (424, 444).

41. The cassette according to clause 40, wherein the syringe holder comprises one or more proximally extending arms (424) and the rigid needle shield holder comprises one or more distally extending protrusions (444), wherein the one or more proximally extending arms (424) of the syringe holder locks to the one or more distally extending protrusions (444) of the rigid needle shield holder thereby forming the second snap joint.

42. The cassette according to clause 40 or 41, wherein upon movement of the syringe holder distally relative to the rigid needle shield holder, the second snap joint is released.

43. The cassette according to clause 42, wherein the auto injector further comprises a chassis adapted for retaining the rigid needle shield holder while the syringe holder is moved distally thereby releasing the second snap fit.

44. The cassette according to any of the preceding clauses 1-5 or 31-43, wherein the cassette skin sensor is locked to the syringe holder by a third snap joint (411, 451).

45. The cassette according to clause 44, wherein the syringe holder comprises a first support surface (411) and the cassette skin sensor comprises an arm (451), wherein the arm of the cassette skin sensor rests against the first support surface of the syringe holder thereby forming the third snap joint.

46. The cassette according to clause 44 or 45, wherein the third snap joint is released by movement of the cassette skin sensor distally relative to the rigid needle shield holder.

47. The cassette according to any of the clauses 44-46, wherein the rigid needle shield holder comprises an inclining surface (440) adapted for releasing the arm (451) of the cassette skin sensor from the first support surface of the syringe holder when moving the cassette skin sensor distally relative to the rigid needle shield holder.

48. The cassette according to clause 47, wherein after the stopper has been moved proximally for emptying the syringe compartment, a second spring in the auto injector exerts a pressure on the cassette skin sensor in the proximal direction, whereby the cassette skin sensor, the rigid needle shield holder, and the syringe holder locks to each other positioning the cassette skin sensor in a proximal position covering the needle.

49. The cassette according to any of the preceding clauses 1-5 or 31-48, wherein:
the arm (451) of the cassette skin sensor (450) comprises a first proximal surface (452); and
the rigid needle shield holder (430) comprises a first distal surface (432),
wherein after delivery of the medicament, the first proximal surface (452) of the cassette skin sensor arm (451) and the first distal surface (432) of the rigid needle shield holder (430) abuts thereby preventing the cassette skin sensor (450) from moving proximally in relation to the rigid needle shield holder (430).

50. The cassette according to any of the preceding clauses 1-5 or 31-49, wherein:
the cassette skin sensor (450) comprises a first distal surface (454); and
the rigid needle shield holder (430) comprises a first proximal surface (434),
wherein after delivery of the medicament, the first distal surface (454) of the cassette skin sensor and the first proximal surface (434) of the rigid needle shield holder abuts thereby preventing the rigid needle shield holder from moving proximally in relation to the cassette skin sensor.

51. The cassette according to any of the preceding clauses 1-5 or 31-50, wherein:
the cassette skin sensor comprises a second proximal surface (456); and
the rigid needle shield holder comprises a second distal surface (436),
wherein after delivery of the medicament, the second proximal surface (456) of the cassette skin sensor and the second distal surface (436) of the rigid needle shield holder abuts thereby preventing the rigid needle shield holder from moving distally in relation to the cassette skin sensor.

52. The cassette according to any of the preceding clauses 1-5 or 31-51, wherein:
the cassette skin sensor comprises a second distal surface (458); and
the syringe holder (410) comprises a first proximal surface (418),
wherein after delivery of the medicament, the second distal surface of the cassette skin sensor and the first proximal surface of the syringe holder abuts thereby preventing the cassette skin sensor from moving distally in relation to the syringe holder.

53. The cassette according to any of the preceding clauses 1-5 or 31-52, wherein:
the arm (451) of the cassette skin sensor (450) comprises a first proximal surface (452); and
the syringe holder (410) comprises a first distal surface (412),
wherein after delivery of the medicament, the first proximal surface (452) of the cassette skin sensor arm (451) and the first distal surface (412) of the syringe holder (410) abuts thereby preventing the syringe holder (410) from moving distally in relation to the cassette skin sensor (450).

54. The cassette according to any of the preceding clauses 1-5 or 31-53, wherein the cassette is absent of springs.

55. The cassette according to any of the preceding clauses 1-5 or 31-54, wherein the cassette further comprises a rigid needle shield sensor (446) adapted for detecting if the rigid needle shield is attached to the syringe compartment.

56. The cassette according to clause 55, wherein rigid needle shield sensor is connected to the rigid needle shield holder.

57. The cassette according to clause 55 or 56, wherein a distal end (447) of the rigid needle shield sensor is connected to the rigid needle shield holder and a proximal end (448) of the rigid needle shield sensor is in contact with the rigid needle shield when the rigid needle shield is connected to the syringe compartment.

58. The cassette according to any of the clauses 55-57, wherein the rigid needle shield sensor comprises a spring loaded rotatable arm and an electronic switch, wherein the rotatable arm is in a depressed position when the rigid needle shield is connected to the syringe compartment, and wherein the rotatable arm is in the depressed position interacts with the electronic switch thereby allowing electronics to detect the presence of the rigid needle shield.

59. The cassette according to any of the clauses 55-58, wherein the cassette further comprises one or more additional rigid needle shield sensors adapted for detecting if the rigid needle shield is attached to the syringe at one or more different locations along the length of the rigid needle shield compared to the first mentioned rigid needle shield sensor.

60. An auto injector (100*e*, 100*f* for administering a medicament, the auto injector extending from a proximal end to a distal end, the auto injector comprising a housing (102, 1102), wherein inside the housing (102, 1102) is comprised;
a cassette receiver (172, 1110) configured to receive a cassette according to any of the preceding clauses;
a piston (168, 1168) configured for moving the stopper inside the syringe of the cassette proximally thereby emptying the syringe of medicament, and;
a drive module (120, 1150) adapted to move the piston.

61. The auto injector according to clause 60 further comprising one or more pins selected from the group of:
a first skin sensor release pin (1156);
a skin sensor forward pin (1158);
a second skin sensor release pin (1159);
a cassette detection pin (1160).

62. The auto injector according to clause 60 or 61, wherein the cassette receiver (1110) is a cassette receiving chassis extending from a proximal end (1111) to a distal end (1112), wherein the proximal end (1111) of the chassis (1110) comprises a ring-shaped chassis part (1114) with one or more openings selected from the group of:
a piston opening (1115) for allowing passage of the auto injector piston (1168) there through;
a first pin opening (1116) for allowing passage of the first skin sensor release pin (1156) there through;
a second pin opening (1117) for allowing passage of the first cassette skin sensor pin (557);
a third pin opening (1118) for allowing passage of:
the skin sensor forward pin (1158) of the auto injector, and/or
the second cassette skin sensor pin (558) there through;

a fourth pin opening (1119) for allowing passage of the second skin sensor release pin (1159) there through;

a fifth opening (1120) for allowing passage of the cassette detection pin (1160) there through.

63. The auto injector according to clause 62, wherein the second pin opening (1117) is a well-shaped opening with an end surface (1121) limiting the distal movement of the first cassette sensor pin (557) and thereby the cassette skin sensor (550) inside the auto injector (100).

64. The auto injector according to any of the clauses 61-63, wherein drive module (1150) is further configured for moving the first skin sensor release pin (1156), the skin sensor forward pin (1158), the second skin sensor release pin (1159), and the cassette detection pin (1160) proximally.

65. The auto injector according to clause 64, wherein when the drive module (1150) moves the first skin sensor release pin (1156) proximally, the cassette skin sensor (550) is distally unlocked from the syringe holder (510) allowing for distal movement of the cassette skin sensor (550), wherein the unlocking of the cassette skin sensor (550) locks the cassette (500) in the auto injector (1000.

66. The auto injector according to clause 64 or 65, wherein when the drive module (1150) moves the piston (1168) proximally for delivery of medicament, the second skin sensor release pin (1156) is also unlocked for movement of the cassette skin sensor (550) proximally after delivery of medicament and/or removal of the auto injector (100*f* from the patients skin.

67. The auto injector according to any of the clauses 61-66 further comprising a skin sensor spring system (1140) pushing the skin sensor forward pin (1158) of the auto injector (1000 against the second cassette skin sensor pin (558) at least after release of the cassette skin sensor (550) from the syringe holder (510) by proximal movement of the first skin sensor release pin (1156) and the a second skin sensor release pin (1159).

68. The auto injector according to clause 66, wherein the skin sensor spring system (1140) pushes the cassette skin sensor (550) proximally in a locked position preventing distal movement of the cassette skin sensor (550).

69. The auto injector according to any of the clauses 60-68, wherein the housing (1102) is in one piece with a proximal opening for receiving the cassette (500).

70. The auto injector according to clause 60, wherein the drive module is adapted to move the cassette receiver, wherein the piston and the cassette receiver can be moved together or separately.

71. The auto injector according to any of the clauses 60 and 70 further comprising a first spring (140) adapted for moving the syringe holder with the syringe compartment connected to the needle proximally for insertion of the needle.

72. The auto injector according to any of the clauses 60 and 70-71, wherein the drive module is further configured for moving the syringe compartment, the syringe holder and the cassette skin sensor in the distal direction relative to the rigid needle shield holder and the rigid needle shield thereby allowing for removal of the rigid needle shield.

73. The auto injector according to any of the clauses 60 and 70-72 further comprising an actuation button, wherein upon activation of the actuation button (142), the drive module moves the piston from a distal position in the proximal direction, and wherein the first spring is released during the movement of the piston in the proximal direction.

74. The auto injector according to clause 73, wherein:
the first spring is adapted for moving the syringe holder for insertion of the needle at a needle insertion speed, and
the drive module is adapted for moving the piston at a medicament delivery speed, wherein the needle insertion speed is larger than the medicament delivery speed,
whereby the piston and the stopper is separated in the longitudinal direction during and for a time period after insertion of the needle before the piston catches up with the syringe compartment.

75. The auto injector according to clause 74, wherein further movement of the piston in the proximal direction after the piston catches up with the syringe compartment, moves the stopper in the proximal direction thereby delivering the medicament.

76. The auto injector according to any of the clauses 60 and 70-75, wherein the auto injector further comprises a syringe sensor adapted for detecting when a syringe is positioned in the syringe holder.

77. The auto injector according to any of the clauses 60 and 70-76, further comprising a second spring exerting a pressure on the cassette skin sensor in the proximal direction.

REFERENCES

100*a* auto injector
100*b* auto injector
100*c* auto injector
100*d* auto injector
100*e* auto injector
100*f* auto injector
100*g* auto injector
102 housing
103 end of the housing
104 end of the housing
106 first part of the housing
108 second part of the housing
110 syringe holder
112 distal surface of syringe holder
114 distal surface of the syringe holder
120 drive module
122 motor in the drive module
124 gear box in the drive module
126 screw or rod in the drive module
128 second drive module
130 rigid needle shield remover
132 first part of the rigid needle shield remover
133 rigid needle shield remover arms
134 distal end of the rigid needle shield remover
135 proximal end of the rigid needle shield remover
136 rigid needle shield remover holder
138 second part of the rigid needle shield remover for holding the rigid needle shield
140 first spring
141 release arm
142 activation button
144 syringe sensor
146 rigid needle shield sensor
147 distal end of the rigid needle shield sensor
148 proximal end of the rigid needle shield sensor 150 skin sensor
152 first rack spring
154 second rack spring
162 first gear rack part
163 connecting finger on the first gear rack part
164 second gear rack part
166 third gear rack part
167 release finder
168 piston
169 constricted portion of the piston
170 cover
172 cassette receiver
174 locking arms on the cassette receiver
175 actuator component
176 light system
177 sensor system
178 skin sensor switch
179 cassette sensor switch
180 chassis
182 locking surface of the chassis
190 slider
192 locking arm on the slider
200 syringe
201 proximal end of the syringe/syringe compartment
202 syringe compartment
203 distal end of the syringe/syringe compartment
204 hollow needle
205 distal end surface of the syringe
206 rigid needle shield
207 inner part of the rigid needle shield
208 stopper
210 plunger rod
400 cassette
410 syringe holder
411 first support surface of the syringe holder
412 first distal surface of the syringe holder
418 first proximal surface of the syringe holder
420 distal end of the syringe holder
421 proximal end of the syringe holder
422 inner recess of the syringe holder
424 distal protrusion of the syringe holder
430 rigid needle shield holder
431 separation part
432 first distal surface of the rigid needle shield holder
434 first proximal surface of the rigid needle shield holder
436 second distal surface of the rigid needle shield holder
438 second proximal surface of the rigid needle shield holder
440 inclining surface of the rigid needle shield holder
442 tab arm of the rigid needle shield holder
444 protruding tab of the rigid needle shield holder
446 rigid needle shield sensor
447 distal end of the rigid needle shield sensor
448 proximal end of the rigid needle shield sensor
450 cassette skin sensor
451 arm of the cassette skin sensor
452 first proximal surface of the cassette skin sensor
453 inwardly protruding part of the cassette skin sensor
454 first distal surface of the cassette skin sensor
456 second proximal surface of the cassette skin sensor
458 second distal surface of the cassette skin sensor
460 opening at the proximal end of the cassette skin sensor
500 cassette
507 syringe holder ring
508 proximal end of the syringe holder
509 distal end of the syringe holder
510 syringe holder
511 syringe holder support tube
512 first syringe holder arm
513 proximal end of the first syringe holder arm
514 proximal surface at the proximal end of the first syringe holder arm
516 second syringe holder arm
517 proximal end of the second syringe holder arm
518 distal surface at the proximal end of the second syringe holder arm
519 ring-shaped syringe holder part
520 proximal support surface of the ring-shaped syringe holder part
521 distal support surface of the ring-shaped syringe holder part
522 first syringe holder locking arm
523 second syringe holder locking arm
524 syringe holder locking protrusions housing
525 piston opening in the ring-shaped syringe holder part
526 first pin opening in the ring-shaped syringe holder part
527 second pin opening in the ring-shaped syringe holder part
528 third pin opening in the ring-shaped syringe holder part
529 fourth pin opening in the ring-shaped syringe holder part
530 rigid needle shield holder/cap
531 first part positioned between the rigid needle shield and the proximal end of the
syringe compartment
535 inner rigid needle shield tube
536 outer rigid needle shield tube
537 distal end of the rigid needle shield holder
538 proximal end of the rigid needle shield holder
539 cassette locking protrusion locking the syringe holder to the auto injector
540 cassette housing
541 proximal end of the cassette housing
542 distal end of the cassette housing
543 distal end surface of the cassette housing
544 locking opening in the cassette housing
545 skin sensor housing opening
546 housing shoulder
547 opening in the housing for inspection of medicament
548 protruding rail on the inside of the cassette housing
550 cassette skin sensor
552 distal end of the cassette skin sensor
553 first locking protrusion
554 second locking protrusion
556 opening for inspection of the syringe
557 first cassette skin sensor pin
558 second cassette skin sensor pin
560 proximal end of the cassette skin sensor
562 skin touching surface of the cassette skin sensor
566 cassette skin sensor arm
567 locking surface of the cassette skin sensor arm
568 cassette skin sensor rail to fit into the rails inside the cassette housing
600 cassette
630 rigid needle shield holder
631 first part positioned between the rigid needle shield and the proximal end of the
syringe compartment
632 rigid needle shield holder pin
650 cassette skin sensor
1102 outer housing 1105 protruding tab on the inside of the housing
1110 cassette receiver/cassette receiving chassis
1111 proximal end of the chassis
1112 distal end of the chassis
1113 distally extending chassis arm
1114 ring-shaped chassis part
1115 piston opening in the proximal ring-shaped chassis part
1116 first pin opening in the proximal ring-shaped chassis part
1117 second pin opening in the proximal ring-shaped chassis part
1118 third pin opening in the proximal ring-shaped chassis part
1119 fourth pin opening in the proximal ring-shaped chassis part
1120 fifth opening in the proximal ring-shaped chassis part
1121 end surface of the second pin opening
1140 spring system acting on the skin sensor
1141 spring guidance pin
1142 supporting chassis for guiding the skin sensor forward pin
1143 spring in the spring system acting on the skin sensor
1150 drive module
1151 motor
1152 gear cover
1153 gear assembly
1154 chassis cover
1155 O-ring
1156 first skin sensor release pin
1158 skin sensor forward pin
1159 second skin sensor release pin
1160 cassette detection pin
1161 guide pin for the skin sensor forward pin
1168 piston internally threaded to match the led screw
1169 led screw
1170 bridge
1171 switch
1180 cassette receiving chassis
1181 release pin
1182 rigid needle shield release pin system
L1 primary position of the syringe holder
L2 secondary position of the syringe holder
L3 tertiary position of the syringe holder
L4 quaternary position of the syringe holder
L5 quinary position of the syringe holder

The invention claimed is:

1. An auto injector for delivery of administering a medicament from a syringe, the syringe including a syringe compartment containing the medicament and extending from a proximal end to a distal end, a hollow needle in fluid connection with the proximal end of the syringe compartment, and a stopper positioned inside the syringe compartment, the auto injector comprising:
a housing extending from a proximal end to a distal end;
a piston positioned within the housing and configured for movement relative thereto, the piston having a release finger thereon;
an electrical motor adapted to move the piston between a proximal position and a distal position in a longitudinal direction of the housing;
a syringe holder positioned within the housing, the syringe holder extending from a proximal end to a distal end and configured to receive the syringe, wherein the piston is configured to move the stopper proximally thereby emptying the syringe compartment; and
a first spring positioned within the housing and adapted for moving the syringe holder with the syringe proximally for insertion of the hollow needle; and
an activation button adapted for activating the electrical motor for moving the piston proximally, wherein movement of the piston proximally releases the first spring; and
a release arm within the housing, wherein the release finger on the piston releases the first spring when the piston passes the release arm, and
wherein the electrical motor is the only motor in the auto injector.

2. The auto injector according to claim 1, wherein the electrical motor is adapted for moving the piston proximally for injection of medicament concurrently with the release of the first spring.

3. The auto injector according to claim 1, wherein further movement of the piston proximally after the piston catches up with the syringe compartment, moves the stopper proximally thereby delivering the medicament.

4. The auto injector according to claim 1, further comprising a syringe sensor adapted for detecting when the syringe is positioned in the syringe holder.

5. The auto injector according to claim 1, wherein:
the first spring is adapted for moving the syringe holder for insertion of the hollow needle at a needle insertion speed, and
the electrical motor is adapted for moving the piston at a medicament delivery speed, wherein the needle insertion speed is greater than the medicament delivery speed,
whereby the piston and the stopper is separated in the longitudinal direction during and for a time period after insertion of the hollow needle before the piston catches up with the syringe compartment.

6. The auto injector according to claim 5, wherein further movement of the piston in proximally after the piston catches up with the syringe compartment, moves the stopper proximally thereby delivering the medicament.

7. The auto injector according to claim 1, further comprising a rigid needle shield remover adapted for separating the proximal end of the syringe compartment and a rigid needle shield of the syringe, wherein the electrical motor is further adapted for moving the syringe holder in a distal direction for separating the proximal end of the syringe compartment and the rigid needle shield.

8. An auto injector for delivery of administering a medicament from a syringe, the syringe including a syringe compartment containing the medicament and extending from a proximal end to a distal end, a hollow needle in fluid connection with the proximal end of the syringe compartment, and a stopper positioned inside the syringe compartment, the auto injector comprising:
a housing extending from a proximal end to a distal end;
a piston positioned within the housing and configured for movement relative thereto;
an electrical motor adapted to move the piston between a proximal position and a distal position in a longitudinal direction of the housing at a medicament delivery speed;
a syringe holder positioned within the housing, the syringe holder extending from a proximal end to a distal end and configured to receive the syringe, wherein the piston is configured to move the stopper proximally thereby emptying the syringe compartment; and a first spring positioned within the housing and adapted for moving the syringe holder proximally for insertion of the hollow needle at a needle insertion speed, and wherein the needle insertion speed is greater than the medicament delivery speed; and an activation button adapted for activating the electrical motor for moving the piston proximally, wherein movement of the piston proximally releases the first spring; and whereby the piston and the stopper are separated in the longitudinal direction during and for a time period after insertion of the hollow needle before the piston catches up with the syringe compartment.

9. The auto injector according to claim 8, wherein the electrical motor is adapted for moving the piston proximally for injection of medicament concurrently with the release of the first spring.

10. The auto injector according to claim 8, wherein further movement of the piston proximally after the piston catches up with the syringe compartment, moves the stopper proximally thereby delivering the medicament.

11. The auto injector according to claim 8, further comprising a syringe sensor adapted for detecting when the syringe is positioned in the syringe holder.

12. The auto injector according to claim 8, further comprising a rigid needle shield remover adapted for separating the proximal end of the syringe compartment and a rigid needle shield of the syringe, wherein the electrical motor is further-adapted for moving the syringe holder in a distal direction for separating the proximal end of the-syringe compartment and the rigid needle shield.

13. The auto injector according to claim 8, further comprising a release arm within the housing, and a release finger on the piston, wherein the release finger on the piston releases the first spring when the piston passes the release arm.

14. An auto injector for delivery of administering a medicament from a syringe, the syringe including a syringe compartment containing the medicament and extending from a proximal end to a distal end, a hollow needle in fluid connection with the proximal end of the syringe compartment, a stopper positioned inside the syringe compartment, and a rigid needle shield connected to the proximal end of the syringe compartment and covering the hollow needle, the auto injector comprising:

a housing extending from a proximal end to a distal end;
a piston positioned within the housing and configured for movement relative thereto;
a syringe holder positioned within the housing, the syringe holder extending from a proximal end to a distal end and configured to receive the syringe, wherein the piston is configured to move the stopper proximally thereby emptying the syringe compartment;
an electrical motor adapted to move the piston between a proximal position and a distal position in a longitudinal direction of the housing, and the electrical motor is further adapted for moving the syringe holder in a distal direction for separating the proximal end of the syringe compartment and the rigid needle shield;
a first spring positioned within the housing and adapted for moving the syringe holder with the syringe proximally for insertion of the hollow needle; and
an activation button adapted for activating the electrical motor for moving the piston proximally, wherein movement of the piston proximally releases the first spring, and
wherein the electrical motor is the only motor in the auto injector.

15. The auto injector according to claim 14, wherein the electrical motor is adapted for moving the piston proximally for injection of medicament concurrently with the release of the first spring.

16. The auto injector according to claim 14, wherein further movement of the piston proximally after the piston catches up with the syringe compartment, moves the stopper proximally thereby delivering the medicament.

17. The auto injector according to claim 14, further comprising a syringe sensor adapted for detecting when the syringe is positioned in the syringe holder.

18. The auto injector according to claim 14, wherein:
the first spring is adapted for moving the syringe holder for insertion of the hollow needle at a needle insertion speed, and
the electrical motor is adapted for moving the piston at a medicament delivery speed, wherein the needle insertion speed is greater than the medicament delivery speed,
whereby the piston and the stopper is separated in the longitudinal direction during and for a time period after insertion of the hollow needle before the piston catches up with the syringe compartment.

19. The auto injector according to claim 18, wherein further movement of the piston proximally after the piston catches up with the syringe compartment, moves the stopper proximally thereby delivering the medicament.

20. The auto injector according to claim 14, further comprising a release arm within the housing, and a release finger on the piston, wherein the release finger on the piston releases the first spring when the piston passes the release arm.

* * * * *